US012605486B2

(12) United States Patent
Heidebrecht et al.

(10) Patent No.: US 12,605,486 B2
(45) Date of Patent: Apr. 21, 2026

(54) AFIBROTIC COMPOUNDS, DEVICES, AND USES THEREOF

(71) Applicant: SIGILON THERAPEUTICS, INC., Cambridge, MA (US)

(72) Inventors: Richard Heidebrecht, Somerville, MA (US); Robert James Miller, East Bridgewater, MA (US); Omid Veiseh, Bellaire, TX (US)

(73) Assignee: SIGILON THERAPEUTICS, INC., Cambridge, MA (US)

( * ) Notice: Subject to any disclaimer, the term of this patent is extended or adjusted under 35 U.S.C. 154(b) by 1271 days.

(21) Appl. No.: 16/977,724

(22) PCT Filed: Mar. 1, 2019

(86) PCT No.: PCT/US2019/020405
§ 371 (c)(1),
(2) Date: Sep. 2, 2020

(87) PCT Pub. No.: WO2019/169333
PCT Pub. Date: Sep. 6, 2019

(65) Prior Publication Data
US 2021/0060205 A1 Mar. 4, 2021

Related U.S. Application Data

(60) Provisional application No. 62/652,883, filed on Apr. 4, 2018, provisional application No. 62/637,803, filed on Mar. 2, 2018.

(51) Int. Cl.

| | |
|---|---|
| ***A61L 27/20*** | (2006.01) |
| ***A61K 9/00*** | (2006.01) |
| ***A61K 9/50*** | (2006.01) |
| ***A61L 27/52*** | (2006.01) |
| ***A61L 27/54*** | (2006.01) |
| ***C07D 235/00*** | (2006.01) |
| ***C07D 249/04*** | (2006.01) |
| ***C07D 249/06*** | (2006.01) |
| ***C07D 279/12*** | (2006.01) |
| ***C07D 309/12*** | (2006.01) |
| ***C07D 405/12*** | (2006.01) |
| ***C07D 417/06*** | (2006.01) |
| ***C07D 491/107*** | (2006.01) |
| ***C08B 37/00*** | (2006.01) |

(52) U.S. Cl.
CPC ............ *A61L 27/20* (2013.01); *A61K 9/0024* (2013.01); *A61K 9/5036* (2013.01); *A61L 27/52* (2013.01); *A61L 27/54* (2013.01); *C07D 235/00* (2013.01); *C07D 249/04* (2013.01); *C07D 249/06* (2013.01); *C07D 279/12* (2013.01); *C07D 309/12* (2013.01); *C07D 405/12* (2013.01); *C07D 417/06* (2013.01); *C07D 491/107* (2013.01); *C08B 37/0084* (2013.01); *A61L 2400/18* (2013.01)

(58) Field of Classification Search
None
See application file for complete search history.

(56) References Cited

U.S. PATENT DOCUMENTS

| | | | |
|---|---|---|---|
| 4,784,950 | A | 11/1988 | Hagen et al. |
| 6,361,771 | B1 | 3/2002 | Tao et al. |
| 6,533,819 | B1 | 3/2003 | Urry et al. |
| 8,741,340 | B2 | 6/2014 | Kusk et al. |
| 9,121,037 | B2 | 9/2015 | Kusk et al. |
| 9,422,373 | B2 | 8/2016 | Vegas et al. |
| 9,555,007 | B2 | 1/2017 | Ma et al. |
| 9,867,781 | B2 | 1/2018 | Anderson et al. |
| 9,925,219 | B2 | 3/2018 | Kauper et al. |
| 10,172,791 | B2 | 1/2019 | Ma et al. |
| 10,278,922 | B2 | 5/2019 | Anderson et al. |
| 10,285,949 | B2 | 5/2019 | Vegas et al. |

(Continued)

FOREIGN PATENT DOCUMENTS

| | | |
|---|---|---|
| CN | 104072478 A | 10/2014 |
| CN | 106795225 A | 5/2017 |

(Continued)

OTHER PUBLICATIONS

Bremond et al., "Formation of liquid-core capsules having a thin hydrogel membrane: liquid pearls" Soft Matter, 2010, vol. 6, No. 11, pp. 2484-2488.

(Continued)

*Primary Examiner* — Celeste A Roney
(74) *Attorney, Agent, or Firm* — Quarles & Brady, LLP

(57) ABSTRACT

Described herein are compounds of Formula (I), modified polymers and implantable elements comprising compounds of Formula (II), as well as compositions and methods of use thereof. In particular, the compounds, modified polymers, implantable elements and related compositions may be used in methods for the prevention and treatment of a disease, disorder or condition in a subject.

(I)

$$A—L^1—M—L^2—P—L^3—Z$$

(II)

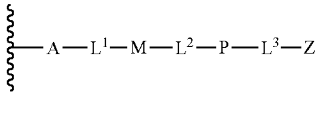

8 Claims, No Drawings

(56) References Cited

U.S. PATENT DOCUMENTS

| | | | |
|---|---|---|---|
| 10,292,936 B2 | 5/2019 | Vegas et al. | |
| 10,426,735 B2 | 10/2019 | Vegas et al. | |
| 2008/0076174 A1 | 3/2008 | Selden et al. | |
| 2013/0259924 A1 | 10/2013 | Bancel et al. | |
| 2014/0010861 A1 | 1/2014 | Bancel et al. | |
| 2014/0271843 A1 | 9/2014 | Ma et al. | |
| 2016/0030359 A1 | 2/2016 | Ma et al. | |
| 2016/0030360 A1 | 2/2016 | Vegas et al. | |
| 2016/0207978 A1 | 7/2016 | Kelly | |
| 2017/0226232 A1* | 8/2017 | Vegas .................. | C12N 5/0677 |
| 2017/0260516 A1 | 9/2017 | Tan et al. | |
| 2018/0318612 A1 | 11/2018 | Tzahor et al. | |
| 2019/0000932 A1 | 1/2019 | Martini et al. | |

FOREIGN PATENT DOCUMENTS

| | | |
|---|---|---|
| JP | 2004-532234 A | 10/2004 |
| JP | 5725475 B2 | 5/2015 |
| JP | 2016-516020 A | 6/2016 |
| JP | 2016-517879 A | 6/2016 |
| JP | 2017-524768 A | 8/2017 |
| WO | 2004/064971 A2 | 8/2004 |
| WO | 2008/021388 A1 | 2/2008 |
| WO | 2008/036308 A2 | 3/2008 |
| WO | 2010/005533 A2 | 1/2010 |
| WO | 2012/112982 A2 | 8/2012 |
| WO | 2012/167223 A1 | 12/2012 |
| WO | 2014/147386 A1 | 9/2014 |
| WO | 2014/153126 A1 | 9/2014 |
| WO | 2015/143418 A2 | 9/2015 |
| WO | 2016/019391 A1 | 2/2016 |
| WO | 2016/187225 A1 | 11/2016 |
| WO | 2017/018086 A1 | 2/2017 |
| WO | 2017/075630 A1 | 5/2017 |
| WO | 2017/075631 A1 | 5/2017 |
| WO | 2017/136358 A1 | 8/2017 |
| WO | 2018/067615 A1 | 4/2018 |
| WO | 2018/206168 A1 | 11/2018 |
| WO | 2019/067766 A1 | 4/2019 |
| WO | 2019/195056 A1 | 10/2019 |

OTHER PUBLICATIONS

Veiseh et al., "Size- and shape-dependent foreign body immune response to materials implanted in rodents and non-human primates" Nature Materials, 2015, vol. 14, pp. 643-652.
Lee et al., "Size and shape of calcium alginate beads produced by extrusion dripping" Chemical Engineering and Technology, 2013, vol. 36, No. 10, pp. 1627-1642.
Vegas et al., "Combinatorial hydrogel library enables identification of materials that mitigate the foreign body response in primates" Nature Biotechnology, 2016, vol. 34, No. 3, pp. 345-352.
International Search Report and Written Opinion for Application No. PCT/US2019/020248 mailed Jun. 26, 2019.
International Search Report and Written Opinion for Application No. PCT/US2019/020405 mailed Jul. 15, 2019.
International Search Report and Written Opinion for Application No. PCT/US2018/053191 mailed Mar. 5, 2019.
Sieving et al., "Ciliary neurotrophic factor (CNTF) for human retinal degeneration: Phase I trial of CNTF delivered by encapsulated cell intraocular implants" Proceedings of the National Academy of Sciences, 2006, vol. 103, No. 10, pp. 3896-3901.
Shintani et al., "Review and update: Current treatment trends for patients with retinitis pigmentosa" Optometry, 2009, vol. 80, No. 7, pp. 384-401.
Wikstrom et al., "Alginate-based microencapsulation of retinal pigment epithelial cell line for cell therapy" Biomaterials, 2008, vol. 29, pp. 869-876.
Carvalho et al., "'Click Chemistry' synthesis of a library of 1,2,3-triazole-substituted galactose derivatives and their evaluation against Trypanosoma cruzi and its cell surface trans-sialidase," Bioorganic & Medicinal Chemistry, vol. 18, No. 7, pp. 2412-2427, (2010).
Corbel et al., "Identification of potential cellular targets of aloisine A by affinity chromatography," Bioorganic & Medicinal Chemistry, vol. 17, No. 15, pp. 5572-5582, (2009).
Struthers et al., "'Click-to-Chelate': Design and Incorporation of Triazole-containing Metal-chelating Systems into Biomolecules of Diagnostic and Therapeutic Interest," Chemistry—A European Journal, vol. 14, No. 20, pp. 6173-6183, (2008).
International Search Report and Written Opinion for PCT/US2017/055001 mailed Nov. 27, 2017.
Arunrungvichian et al., "Selectivity optimization of substituted 1,2,3-Triazoles as a7 nicotinic acetylcholine receptor agonists" ACS Chemical Neuroscience, vol. 6, No. 8, 2015, pp. 1317-1330.
RN:1545351-08-3, Database Registry [Online], Retrieved from STN, Feb. 16, 2014.
Panda et al., "A nucleus-imaging probe that selectively stabilizes a minor conformation of c-MYC G-quadruplex and Down-regulates c-MYC Transcription in Human Cancer Cells" Scienctific Reports, 2015, vol. 5, pp. 1-16.
Bochenek et al., "Alginate encapsulation as long-term immune protection of allogeneic pancreatic islet cells transplanted into the omental bursa of macaques" Nature Biomedical Engineering, 2018, vol. 2, No. 11, pp. 810-821.
Vegas et al., "Long-term glycemic control using polymer-encapsulated human stem cell-derived beta cells in immune-competent mice" Nature Medicine, 2016, vol. 22, No. 3, pp. 306-311.
International Search Report and Written Opinion for Application No. PCT/US2019/024385 mailed Aug. 7, 2019.
International Search Report and Written Opinion for Application No. PCT/US2019/024371 mailed Aug. 14, 2019.
Llacua et al., "Extracellular matrix molecules and their potential contribution to the function of transplanted pancreatic islets" Diabetologia, 2018, vol. 61, pp. 1261-1272.
Llacua et al., "Laminin and collagen IV inclusion in immunoisolating microcapsules reduces cytokine-mediated cell death in human pancreatic islets" Journal of Tissue Engineering and Regenerative Medicine, 2017, 25 pages.
Orive et al., "Engineering a clinically translatable bioartificial pancreas to treat type I diabetes" Trends in Biotechnology, 2018, 12 pages.
Llacua et al., "Extracellular matrix components supporting human islet function in alginate-based immunoprotective microcapsules for treatment of diabetes" Journal of Biomedical Materials Research Part A, 2018, 10 pages.
Bochenek et al., "Alginate encapsulation as long-term immune protection of allogeneic pancreatic islet cells transplanted into the omental bursa of macaques" Nature Biomedical Engineering, vol. 2, No. 11, pp. 810-821, 2018.
Belhaj, "Enhancements in alginate microencapsulation technology & impacts on cell therapy development", Disseration, Jan. 2018 (109 pages).
Weber et al., "Multifunctional pancreatic islet encapsulation barriers achieved via multilayer PEG hydrogels", Cell Transplantation, vol. 16, No. 10, pp. 1049-1057, 2007.
Jeon et al., "Biodegradable, photocrosslinked alginate hydrogels with independently tailorable physical properties and cell adhesivity", Tissue Engineering, vol. 16, No. 9, pp. 2915-2925, 2010.
International Search Report and Written Opinion for Application No. PCT/US2019/053637 mailed Feb. 14, 2020.
International Search Report and Written Opinion for Application No. PCT/2020/02585 mailed Aug. 28, 2020.
International Search Report and Written Opinion for Application No. PCT/2020/025511 mailed Aug. 28, 2020.
Mettler et al., "Poloxamer 188 as a supplement to barium cross-linked ultra-high viscosity alginate for immunoisolation of transplanted islet cells" Metabolomics, 2015, vol. 5, Issue 4, 5 pages.

* cited by examiner

AFIBROTIC COMPOUNDS, DEVICES, AND USES THEREOF

CLAIM OF PRIORITY

This application is a U.S. national phase application and claims the benefit of priority under 35 U.S.C § 371 of International Application No. PCT/US2019/020405, filed on Mar. 1, 2019, which claims priority to U.S. Provisional Application No. 62/637,803, filed Mar. 2, 2018 and U.S. Application No. 62/652,883, filed Apr. 4, 2018. The disclosure of each of the foregoing applications is incorporated herein by reference in its entirety.

BACKGROUND

The function of implanted devices depends in large part on the biological immune response pathway of the recipient (Anderson et al., *Semin. Immunol.* 20:86-100 (2008); Langer, *Adv. Mater.* 21:3235-3236 (2009)). Modulation of the immune response may impart a beneficial effect on the fidelity and function of these devices. As such, there is a need in the art for new compounds, compositions, and devices that achieve this goal.

SUMMARY

Described herein are compounds of Formula (I), modified polymers and implantable elements comprising compounds of Formula (II), as well as compositions and methods of use thereof. In particular, the compounds, modified polymers, implantable elements and related compositions may be used in methods for the prevention and treatment of a disease, disorder or condition in a subject. In some embodiments, the compounds, modified polymers, implantable elements, and related compositions are capable of modulating the immune response in a subject, e.g., upregulating or downregulating the immune response in a subject.

In one aspect, the disclosure features a compound of Formula (I):

$$A\text{-}L^1\text{-}M\text{-}L^2\text{-}P\text{-}L^3\text{-}Z \qquad (I)$$

or a pharmaceutically acceptable salt thereof, wherein the variables A, $L^1$, M, $L^2$, P, $L^3$, Z, and subvariables thereof are defined herein. In some embodiments, the compound of Formula (I) or a pharmaceutically acceptable salt thereof (e.g., a compound of Formulas (I-a), (I-b), (I-b-i), (I-b-ii), (I-b-iii), (I-c), (I-d), (I-e), (I-e-i), (I-e-ii), (I-f), (I-g), (I-g-i), or (I-g-ii)) is one of the compounds shown in Table 1 herein.

In another aspect, the disclosure features a polymer modified with a compound of Formula (II):

(II)

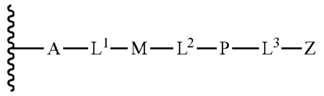

or a pharmaceutically acceptable salt thereof, wherein the variables A, $L^1$, M, $L^2$, P, $L^3$, Z, and subvariables thereof are defined herein. In some embodiments, the polymer is a polysaccharide, e.g., alginate, hyaluronate, or chitosan. In some embodiment, the polymer is alginate. In some embodiments, the compound of Formula (II) or a pharmaceutically acceptable salt thereof (e.g., a compound of Formulas (II-a), (II-b), (II-b-i), (II-b-ii), (II-b-iii), (II-c), (II-d), (II-e), (II-e-i), (II-f), (II-g), (II-g-i), or (II-g-ii)) is one of the compounds shown in Table 2 herein.

In another aspect, the disclosure features an implantable element (e.g., a device or material) comprising a compound of Formula (II), or a pharmaceutically acceptable salt thereof, as described herein. In some embodiments, the compound is associated with (e.g., covalently bound to) the implantable element. In other embodiments, the implantable element comprises a modified polymer comprising a compound of Formula (II). In some embodiments, the compound of Formula (II) or a pharmaceutically acceptable salt thereof (e.g., a compound of Formulas (II-a), (II-b), (II-b-i), (II-b-ii), (II-b-iii), (II-c), (II-d), (II-e), (II-e-i), (II-f), (II-g), (II-g-i), or (II-g-ii)) is one of the compounds shown in Table 2 herein.

In some embodiments, the implantable element comprises a cell. Exemplary cell types include an epithelial cell, endothelial cell, fibroblast cell, mesenchymal stem cell, or keratinocyte cell. In some embodiments, the implantable element comprises a retinal pigment epithelial cell (RPE cell) or a mesenchymal stem cell (MSC). In some embodiments, the implantable element comprises an engineered cell (e.g., an engineered RPE cell or an engineered MSC).

In some embodiments, the cell (e.g., an engineered cell) produces a substance, e.g., a therapeutic agent. Exemplary therapeutic agents include a nucleic acid (e.g., an RNA or DNA), protein (e.g., a hormone, enzyme, antibody, antibody fragment, antigen, or epitope), small molecule, lipid, drug, vaccine, or any derivative thereof. For example, an implantable element may comprise an engineered cell capable of producing a protein (e.g., a blood clotting factor, e.g., a Factor VIII protein or a Factor IX protein).

In another aspect, the disclosure features a method of providing a substance (e.g., a therapeutic agent) to a subject, comprising administering to the subject an implantable element comprising a compound of Formula (II) as described herein. In some embodiments, the substance is a therapeutic agent, e.g., a protein (e.g., a blood clotting factor, e.g., a Factor VIII protein or a Factor IX protein).

In another aspect, the disclosure features a method of treating a disease, disorder, or condition to a subject comprising administering to the subject an implantable element comprising a compound of Formula (II), as described herein. In some embodiments, the disorder is a blood clotting disorder (e.g., hemophilia). In some embodiments, the disorder is a lysosomal storage disorder (e.g., Fabry Disease, Gaucher Disease, Pompe Disease, or MPS I). In some embodiments, the disorder is a neurodegenerative disease. In some embodiments, the method comprises modulating an immune response in the subject.

In any and all aspects of the disclosure, in some embodiments, the compound of Formula (I), a polymer modified with a compound of Formula (II), or an implantable element (e.g., device or material) comprising a compound of Formula (II) is a compound, polymer, or implantable element other than a compound, polymer, or implantable element described in any one of WO2012/112982, WO2012/167223, WO2014/153126, WO2016/187225, WO2016/019391, WO2017/075630, WO 2017/075631, and US 2016-0030359. In some embodiments, the compound of Formula (I) or a polymer modified with a compound of Formula (II) is other than a compound or polymer described in any one of WO2012/112982, WO2012/167223, WO2014/153126, WO2016/187225, WO2016/019391, WO2017/075630, WO 2017/075631, and US 2016-0030359. In some embodiments, the implantable element (e.g., device or material) comprising a compound of Formula (II) is other than an implantable element described in any one of WO2012/112982, WO2012/167223, WO2014/153126, WO2016/187225, WO2016/019391, WO2017/075630, WO 2017/075631, and US 2016-0030359. In some embodiments, the compound of Formula (II) is attached to a polymer or implantable element (e.g., device or material) through an attachment group other than an attachment group described in any one of WO2012/112982, WO2012/167223, WO2014/153126, WO2016/187225, WO2016/019391, WO2017/075630, WO 2017/075631, and US 2016-0030359.

The details of one or more embodiments of the invention are set forth herein. Other features, objects, and advantages of the invention will be apparent from the Detailed Description, the Figures, the Examples, and the Claims.

DETAILED DESCRIPTION

The disclosure provides a compound, e.g., a compound of Formula (I), polymers modified with a compound of Formula (II), and implantable elements (e.g., devices and materials) comprising a compound of Formula (II), as well as related compositions and methods of use thereof. In particular, the compounds of Formula (I) and polymers and implantable elements comprising a compound of Formula (II) may be used in methods for the prevention and treatment of a disease, disorder or condition in a subject. In some embodiments, the compounds of Formula (I) and polymers and implantable elements comprising a compound of Formula (II), as well as pharmaceutically acceptable salts, solvates, hydrates, tautomers, stereoisomers, isotopically labeled derivatives thereof, are capable of modulating the immune response in a subject, e.g., upregulating or downregulating the immune response in a subject.

Definitions

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"About", when used herein to modify a numerically defined parameter (e.g., a physical description of a polymer or implantable element as described herein, such as diameter, sphericity, number of cells in a particle, the number of particles in a preparation), means that the parameter may vary by as much as 15% above or below the stated numerical value for that parameter. For example, an implantable element defined as having a diameter of about 1.5 millimeters (mm) and encapsulating about 5 million (M) cells may have a diameter of 1.275 to 1.725 mm and may encapsulate about 4.25 M to 5.75 M cells. In some embodiments, about means that the parameter may vary by as much as 10% above or below the stated numerical value for that parameter.

"Acquire" or "acquiring", as used herein, refer to obtaining possession of a value, e.g., a numerical value, or image, or a physical entity (e.g., a sample), by "directly acquiring" or "indirectly acquiring" the value or physical entity. "Directly acquiring" means performing a process (e.g., performing an analytical method or protocol) to obtain the value or physical entity. "Indirectly acquiring" refers to receiving the value or physical entity from another party or source (e.g., a third-party laboratory that directly acquired the physical entity or value). Directly acquiring a value or physical entity includes performing a process that includes a physical change in a physical substance or the use of a machine or device. Examples of directly acquiring a value include obtaining a sample from a human subject. Directly acquiring a value includes performing a process that uses a machine or device, e.g., fluorescence microscope to acquire fluorescence microscopy data.

"Administer", "administering", or "administration", as used herein, refer to implanting, absorbing, ingesting, injecting, or otherwise introducing an entity described herein (e.g., a particle comprising a first compartment, a second compartment, and a compound of Formula (I) (including particles encapsulating cells, e.g., engineered RPE cells), or a composition comprising said particles), or providing the same to a subject.

"Cell," as used herein, refers to an engineered cell or a cell that is not engineered.

"Effective amount" as used herein refers to an amount of a compound, modified polymer, or implantable element comprising a compound described herein, e.g, further comprising a cell, e.g., an engineered cell, or an agent, e.g., a therapeutic agent, produced by a cell, e.g., an engineered cell, sufficient to elicit a biological response, e.g., to treat a disease, disorder, or condition. As will be appreciated by those of ordinary skill in this art, the effective amount may vary depending on such factors as the desired biological endpoint, the pharmacokinetics of the therapeutic agent, composition or implantable element, the condition being treated, the mode of administration, and the age and health of the subject. An effective amount encompasses therapeutic and prophylactic treatment. For example, to treat a fibrotic condition, an effective amount of a compound may reduce the fibrosis or stop the growth or spread of fibrotic tissue.

An "endogenous nucleic acid" as used herein, is a nucleic acid that occurs naturally in a subject cell.

An "endogenous polypeptide," as used herein, is a polypeptide that occurs naturally in a subject cell.

"Engineered cell," as used herein, is a cell having a non-naturally occurring alteration, and typically comprises a nucleic acid sequence (e.g., DNA or RNA) or a polypeptide not present (or present at a different level than) in an otherwise similar cell under similar conditions that is not engineered (an exogenous nucleic acid sequence). In an embodiment, an engineered cell comprises an exogenous nucleic acid (e.g., a vector or an altered chromosomal sequence). In an embodiment, an engineered cell comprises an exogenous polypeptide. In an embodiment, an engineered cell comprises an exogenous nucleic acid sequence, e.g., a sequence, e.g., DNA or RNA, not present in a similar cell that is not engineered. In an embodiment, the exogenous nucleic acid sequence is chromosomal, e.g., the exogenous nucleic acid sequence is an exogenous sequence disposed in endogenous chromosomal sequence. In an embodiment, the exogenous nucleic acid sequence is chromosomal or extra chromosomal, e.g., a non-integrated vector. In an embodiment, the exogenous nucleic acid sequence comprises an RNA sequence, e.g., an mRNA. In an embodiment, the exogenous nucleic acid sequence comprises a chromosomal or extra-chromosomal exogenous nucleic acid sequence that comprises a sequence which is expressed as RNA, e.g., mRNA or a regulatory RNA. In an embodiment, the exogenous nucleic acid sequence comprises a chromosomal or extra-chromosomal nucleic acid sequence, which comprises a sequence that encodes a polypeptide, or which is expressed as a polypeptide. In an embodiment, the exogenous nucleic acid sequence comprises a first chromosomal or extra-chromosomal exogenous nucleic acid sequence that modulates the conformation or expression of a second nucleic acid sequence, wherein the second amino acid sequence can be exogenous or endogenous. For example, an engineered cell can comprise an exogenous nucleic acid that controls the expression of an endogenous sequence. In an embodiment, an engineered cell comprises a polypeptide present at a level or distribution which differs from the level found in a similar cell that has not been engineered. In an embodiment, an engineered cell comprises an cell engineered to provide an RNA or a polypeptide. For example, an engineered cell may comprise an exogenous nucleic acid sequence comprising a chromosomal or extra-chromosomal exogenous nucleic acid sequence that comprises a sequence which is expressed as RNA, e.g., mRNA or a regulatory RNA. In an embodiment, an engineered cell comprises an exogenous nucleic acid sequence that comprises a chromosomal or extra-chromosomal nucleic acid sequence comprising a sequence that encodes a polypeptide, or which is expressed as a polypeptide. In an embodiment, an engineered cell comprises an exogenous nucleic acid sequence that modulates the conformation or expression of an endogenous sequence.

An "exogenous nucleic acid," as used herein, is a nucleic acid that does not occur naturally in a subject cell.

An "exogenous polypeptide," as used herein, is polypeptide that does not occur naturally in a subject cell.

An "implantable element" as used herein, comprises a cell, e.g., a plurality of cells, e.g., a cluster of cells, wherein the cell or cells are entirely or partially disposed within an enclosing component (which enclosing component is other than a cell), e.g., the enclosing component comprises a non-cellular component. The term "implantable element" comprises a device or material described herein. In an embodiment, the implantable element inhibits an immune attack, or the effect of the immune attack, on the enclosed cell or cells. In an embodiment, the implantable element comprises a semipermeable membrane or a semipermeable polymer matrix or coating. Typically, the implantable element allows passage of small molecules, e.g., nutrients and waste products. Typically, the implantable element allows passage of a product (e.g., a therapeutic polypeptide) released by a cell disposed within the enclosing component. In an embodiment, placement within an implantable element minimizes an effect of a host response (e.g., an immune response, e.g., a fibrotic response) directed at the implantable element, e.g., against a cell within an implantable element, e.g., as compared with a similar cell that is not disposed in an implantable element. The implantable element described herein comprises a compound of Formula (II) or a pharmaceutically acceptable salt thereof, that minimizes an effect of an immune response, e.g., a fibrotic response, of the subject directed at the implantable element, e.g., against the enclosing component or a cell within the implantable element, e.g., as compared with a similar or otherwise identical implantable element lacking the compound. In some embodiments, the implantable element (e.g., a device or material) is associated (e.g., directly associated) with a compound described herein, e.g., a compound of Formula (II). In some embodiments, the compound of Formula (II) is directly bound to the implantable element (e.g., a device or material). In some embodiments, the implantable element (e.g., a device or material) comprises a polymer modified with a compound of Formula (II).

"Polypeptide", as used herein, refers to a polymer comprising amino acid residues linked through peptide bonds and having at least two, and in embodiments, at least 10, 100, or 200 amino acid residues.

"Prevention," "prevent," and "preventing" as used herein refers to a treatment that comprises administering or applying a therapy, e.g., administering a composition of implantable elements encapsulating cells (e.g., as described herein), prior to the onset of a disease, disorder, or condition to preclude the physical manifestation of said disease, disorder, or condition. In some embodiments, "prevention," "prevent," and "preventing" require that signs or symptoms of the disease, disorder, or condition have not yet developed or have not yet been observed. In some embodiments, treatment comprises prevention and in other embodiments it does not.

A "replacement therapy" or "replacement protein" is a therapeutic protein or functional fragment thereof that replaces or augments a protein that is diminished, present in insufficient quantity, altered (e.g., mutated) or lacking in a subject having a disease or condition related to the diminished, altered or lacking protein. Examples are certain blood clotting factors in certain blood clotting disorders or certain lysosomal enzymes in certain lysosomal storage diseases. In an embodiment, a replacement therapy or replacement protein provides the function of an endogenous protein. In an embodiment, a replacement therapy or replacement protein has the same amino acid sequence of a naturally occurring variant, e.g., a wild type allele or an allele not associated with a disorder, of the replaced protein. In an embodiment, or replacement therapy or a replacement protein differs in amino acid sequence from a naturally occurring variant, e.g., a wild type allele or an allele not associated with a disorder, e.g., the allele carried by a subject, at no more than about 1, 2, 3, 4, 5, 10, 15 or 20% of the amino acid residues.

"Subject" as used herein refers to a human or non-human animal. In an embodiment, the subject is a human (i.e., a male or female, e.g., of any age group, a pediatric subject (e.g., infant, child, adolescent) or adult subject (e.g., young adult, middle-aged adult, or senior adult)). In an embodiment, the subject is a non-human animal, for example, a mammal (e.g., a primate (e.g., a cynomolgus monkey or a rhesus monkey)). In an embodiment, the subject is a commercially relevant mammal (e.g., a cattle, pig, horse, sheep, goat, cat, or dog) or a bird (e.g., a commercially relevant bird such as a chicken, duck, goose, or turkey). In certain embodiments, the animal is a mammal. The animal may be a male or female and at any stage of development. A non-human animal may be a transgenic animal.

"Treatment," "treat," and "treating" as used herein refers to one or more of reducing, reversing, alleviating, delaying the onset of, or inhibiting the progress of one or more of a symptom, manifestation, or underlying cause, of a disease, disorder, or condition. In an embodiment, treating comprises reducing, reversing, alleviating, delaying the onset of, or inhibiting the progress of a symptom of a disease, disorder, or condition. In an embodiment, treating comprises reducing, reversing, alleviating, delaying the onset of, or inhibiting the progress of a manifestation of a disease, disorder, or condition. In an embodiment, treating comprises reducing, reversing, alleviating, reducing, or delaying the onset of an underlying cause of a disease, disorder, or condition. In some embodiments, "treatment," "treat," and "treating" require that signs or symptoms of the disease, disorder, or condition have developed or have been observed. In other embodiments, treatment may be administered in the absence of signs or symptoms of the disease or condition, e.g., in preventive treatment. For example, treatment may be administered to a susceptible individual prior to the onset of symptoms (e.g., considering a history of symptoms and/or in light of genetic or other susceptibility factors). Treatment may also be continued after symptoms have resolved, for example, to delay or prevent recurrence. In some embodiments, treatment comprises prevention and in other embodiments it does not.

Selected Chemical Definitions

Definitions of specific functional groups and chemical terms are described in more detail below. The chemical elements are identified in accordance with the Periodic Table of the Elements, CAS version, *Handbook of Chemistry and Physics,* $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry,* $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* $3^{rd}$ Edition, Cambridge University Press, Cambridge, 1987.

The abbreviations used herein have their conventional meaning within the chemical and biological arts. The chemical structures and formulae set forth herein are constructed according to the standard rules of chemical valency known in the chemical arts.

When a range of values is listed, it is intended to encompass each value and sub-range within the range. For example, "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

As used herein, "alkyl" refers to a radical of a straight-chain or branched saturated hydrocarbon group having from 1 to 24 carbon atoms ("$C_1$-$C_{24}$ alkyl"). In some embodiments, an alkyl group has 1 to 12 carbon atoms ("$C_1$-$C_{12}$ alkyl"), 1 to 8 carbon atoms ("$C_1$-$C_8$ alkyl"), 1 to 6 carbon atoms ("$C_1$-$C_6$ alkyl"), 1 to 5 carbon atoms ("$C_1$-$C_5$ alkyl"), 1 to 4 carbon atoms ("$C_1$-$C_4$ alkyl"), 1 to 3 carbon atoms ("$C_1$-$C_3$ alkyl"), 1 to 2 carbon atoms ("$C_1$-$C_2$ alkyl"), or 1 carbon atom ("$C_1$ alkyl"). In some embodiments, an alkyl group has 2 to 6 carbon atoms ("$C_2$-$C_6$ alkyl"). Examples of $C_1$-$C_6$ alkyl groups include methyl ($C_1$, ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Each instance of an alkyl group may be independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent.

As used herein, "alkenyl" refers to a radical of a straight-chain or branched hydrocarbon group having from 2 to 24 carbon atoms, one or more carbon-carbon double bonds, and no triple bonds ("$C_2$-$C_{24}$ alkenyl"). In some embodiments, an alkenyl group has 2 to 10 carbon atoms ("$C_2$-$C_{10}$ alkenyl"), 2 to 8 carbon atoms ("$C_2$-$C_8$ alkenyl"), 2 to 6 carbon atoms ("$C_2$-$C_6$ alkenyl"), 2 to 5 carbon atoms ("$C_2$-$C_5$ alkenyl"), 2 to 4 carbon atoms ("$C_2$-$C_4$ alkenyl"), 2 to 3 carbon atoms ("$C_2$-$C_3$ alkenyl"), or 2 carbon atoms ("$C_2$ alkenyl"). The one or more carbon-carbon double bonds can be internal (such as in 2-butenyl) or terminal (such as in 1-butenyl). Examples of $C_2$-$C_4$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$-$C_6$ alkenyl groups include the aforementioned $C_2$-$C_4$ alkenyl groups as well as pentenyl ($C_5$), pentadienyl ($C_5$), hexenyl ($C_6$), and the like. Each instance of an alkenyl group may be independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent.

As used herein, the term "alkynyl" refers to a radical of a straight-chain or branched hydrocarbon group having from 2 to 24 carbon atoms, one or more carbon-carbon triple bonds ("$C_2$-$C_{24}$ alkenyl"). In some embodiments, an alkynyl group has 2 to 10 carbon atoms ("$C_2$-$C_{10}$ alkynyl"), 2 to 8 carbon atoms ("$C_2$-$C_8$ alkynyl"), 2 to 6 carbon atoms ("$C_2$-$C_6$ alkynyl"), 2 to 5 carbon atoms ("$C_2$-$C_5$ alkynyl"), 2 to 4 carbon atoms ("$C_2$-$C_4$ alkynyl"), 2 to 3 carbon atoms ("$C_2$-$C_3$ alkynyl"), or 2 carbon atoms ("$C_2$ alkynyl"). The one or more carbon-carbon triple bonds can be internal (such as in 2-butynyl) or terminal (such as in 1-butynyl). Examples of $C_2$-$C_4$ alkynyl groups include ethynyl ($C_2$), 1-propynyl ($C_3$), 2-propynyl ($C_3$), 1-butynyl ($C_4$), 2-butynyl ($C_4$), and the like. Each instance of an alkynyl group may be independently optionally substituted, i.e., unsubstituted (an "unsubstituted alkynyl") or substituted (a "substituted alkynyl") with one or more substituents e.g., for instance from 1 to 5 substituents, 1 to 3 substituents, or 1 substituent.

As used herein, the term "heteroalkyl," refers to a non-cyclic stable straight or branched chain, or combinations thereof, including at least one carbon atom and at least one heteroatom selected from the group consisting of 0, N, P, Si, and S, and wherein the nitrogen and sulfur atoms may optionally be oxidized, and the nitrogen heteroatom may optionally be quaternized. The heteroatom(s) 0, N, P, S, and Si may be placed at any position of the heteroalkyl group. Exemplary heteroalkyl groups include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2$, $—S(O)—CH_3$, $—CH_2—CH_2—S(O)_2—CH_3$, $—CH{=}CH—O—CH_3$, $—Si(CH_3)_3$, $—CH_2—CH{=}N—OCH_3$, $—CH{=}CH—N(CH_3)—CH_3$, $—O—CH_3$, and $—O—CH_2—CH_3$. Up to two or three heteroatoms may be consecutive, such as, for example, $—CH_2—NH—OCH_3$ and $—CH_2—O—Si(CH_3)_3$. Where "heteroalkyl" is recited, followed by recitations of specific heteroalkyl groups, such as $—CH_2O$, $—NR^CR^D$, or the like, it will be understood that the terms heteroalkyl and $—CH_2O$ or $—NR^CR^D$ are not redundant or mutually exclusive. Rather, the specific heteroalkyl groups are recited to add clarity. Thus, the term "heteroalkyl" should not be interpreted herein as excluding specific heteroalkyl groups, such as $—CH_2O$, $—NR^CR^D$, or the like.

The terms "alkylene," "alkenylene," "alkynylene," or "heteroalkylene," alone or as part of another substituent, mean, unless otherwise stated, a divalent radical derived from an alkyl, alkenyl, alkynyl, or heteroalkyl, respectively. An alkylene, alkenylene, alkynylene, or heteroalkylene group may be described as, e.g., a $C_1$-$C_6$-membered alkylene, $C_2$-$C_6$-membered alkenylene, $C_2$-$C_6$-membered alkynylene, or $C_1$-$C_6$-membered heteroalkylene, wherein the term "membered" refers to the non-hydrogen atoms within the moiety. In the case of heteroalkylene groups, heteroatoms can also occupy either or both chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2R'$— may represent both —$C(O)_2R'$— and —$R'C(O)_2$—.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_6$-$C_{14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). An aryl group may be described as, e.g., a $C_6$-$C_{10}$-membered aryl, wherein the term "membered" refers to the non-hydrogen ring atoms within the moiety. Aryl groups include phenyl, naphthyl, indenyl, and tetrahydronaphthyl. Each instance of an aryl group may be independently optionally substituted, i.e., unsubstituted (an "unsubstituted aryl") or substituted (a "substituted aryl") with one or more substituents.

As used herein, "heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group may be described as, e.g., a 6-10-membered heteroaryl, wherein the term "membered" refers to the non-hydrogen ring atoms within the moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Each instance of a heteroaryl group may be independently optionally substituted, i.e., unsubstituted (an "unsubstituted heteroaryl") or substituted (a "substituted heteroaryl") with one or more substituents.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Other exemplary heteroaryl groups include heme and heme derivatives.

As used herein, the terms "arylene" and "heteroarylene," alone or as part of another substituent, mean a divalent radical derived from an aryl and heteroaryl, respectively.

As used herein, "cycloalkyl" refers to a radical of a non-aromatic cyclic hydrocarbon group having from 3 to 10 ring carbon atoms ("$C_3$-$C_{10}$ cycloalkyl") and zero heteroatoms in the non-aromatic ring system. In some embodiments, a cycloalkyl group has 3 to 8 ring carbon atoms ("$C_3$-$C_8$ cycloalkyl"), 3 to 6 ring carbon atoms ("$C_3$-$C_6$ cycloalkyl"), or 5 to 10 ring carbon atoms ("$C_5$-$C_{10}$ cycloalkyl"). A cycloalkyl group may be described as, e.g., a $C_4$-$C_7$-membered cycloalkyl, wherein the term "membered" refers to the non-hydrogen ring atoms within the moiety. Exemplary $C_3$-$C_6$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_3$-$C_8$ cycloalkyl groups include, without limitation, the aforementioned $C_3$-$C_6$ cycloalkyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), cubanyl ($C_8$), bicyclo[1.1.1]pentanyl ($C_5$), bicyclo[2.2.2]octanyl ($C_8$), bicyclo[2.1.1]hexanyl ($C_6$), bicyclo[3.1.1]heptanyl ($C_7$), and the like. Exemplary $C_3$-$C_{10}$ cycloalkyl groups include, without limitation, the aforementioned $C_3$-$C_8$ cycloalkyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro [4.5] decanyl ($C_{10}$), and the like. As the foregoing examples illustrate, in certain embodiments, the cycloalkyl group is either monocyclic ("monocyclic cycloalkyl") or contain a fused, bridged or spiro ring system such as a bicyclic system ("bicyclic cycloalkyl") and can be saturated or can be partially unsaturated. "Cycloalkyl" also includes ring systems wherein the cycloalkyl ring, as defined above, is fused with one or more aryl groups wherein the point of attachment is on the cycloalkyl ring, and in such instances, the number of carbons continue to designate the number of carbons in the cycloalkyl ring system. Each instance of a cycloalkyl group may be independently optionally substituted, i.e., unsubstituted (an "unsubstituted cycloalkyl") or substituted (a "substituted cycloalkyl") with one or more substituents.

"Heterocyclyl" as used herein refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more cycloalkyl groups wherein the point of attachment is either on the cycloalkyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. A heterocyclyl group may be described as, e.g., a 3-7-membered heterocyclyl, wherein the term "membered" refers to the non-hydrogen ring atoms, i.e., carbon, nitrogen, oxygen, sulfur, boron, phosphorus, and silicon, within the moiety. Each instance of heterocyclyl may be independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, piperazinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl or thiomorpholinyl-1,1-dioxide. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Amino" as used herein refers to the radical —$NR^CR^D$, wherein $R^C$ and $R^D$ are each independently hydrogen, $C_1$-$C_{12}$ alkyl, $C_3$-$C_{10}$ cycloalkyl, $C_3$-$C_{10}$ heterocyclyl, $C_6$-$C_{10}$ aryl, and $C_5$-$C_{10}$ heteroaryl. In some embodiments, amino refers to $NH_2$.

As used herein, "cyano" refers to the radical —CN.

As used herein, "halo" or "halogen," independently or as part of another substituent, mean, unless otherwise stated, a fluorine (F), chlorine (Cl), bromine (Br), or iodine (I) atom.

As used herein, "hydroxy" refers to the radical —OH.

Alkyl, alkenyl, alkynyl, heteroalkyl, cycloalkyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" cycloalkyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, such as any of the substituents described herein that result in the formation of a stable compound. The present invention contemplates any and all such combinations to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Two or more substituents may optionally be joined to form aryl, heteroaryl, cycloalkyl, or heterocyclyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Compounds of Formula (I) or Formula (II) described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high-pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E.L. Eliel, Ed., Univ. of Notre Dame Press, Notre Dame, IN 1972). The invention additionally encompasses compounds described herein as individual isomers substantially free of other isomers, and alternatively, as mixtures of various isomers.

As used herein, a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 99% by weight, more than 99.5% by weight, or more than 99.9% by weight, of the enantiomer. In certain embodiments, the weights are based upon total weight of all enantiomers or stereoisomers of the compound.

Compounds of Formula (I) or Formula (II) described herein may also comprise one or more isotopic substitutions. For example, H may be in any isotopic form, including $^{1}H$, $^{2}H$ (D or deuterium), and $^{3}H$ (T or tritium); C may be in any isotopic form, including $^{12}C$, $^{13}C$, and $^{14}C$; O may be in any isotopic form, including $^{16}O$ and $^{18}O$; and the like.

The term "pharmaceutically acceptable salt" is meant to include salts of the active compounds that are prepared with relatively nontoxic acids or bases, depending on the particular substituents found on the compounds described herein. When compounds used in the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds used in the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, e.g., Berge et al, *Journal of Pharmaceutical Science* 66: 1-19 (1977)). Certain specific compounds used in the present disclosure contain both basic and acidic functionalities that allow the compounds to be converted into either base or acid addition salts. These salts may be prepared by methods known to those skilled in the art. Other pharmaceutically acceptable carriers known to those of skill in the art are suitable for use in the present disclosure.

In addition to salt forms, the disclosure may employ compounds of Formula (I) in a prodrug form. Prodrugs are those compounds that readily undergo chemical changes under physiological conditions to provide the compounds useful in the present invention. Additionally, prodrugs can be converted to useful compounds of Formula (I) or Formula (II) by chemical or biochemical methods in an ex vivo environment.

Certain compounds of Formula (I) or Formula (II) described herein can exist in unsolvated forms as well as solvated forms, including hydrated forms. In general, the solvated forms are equivalent to unsolvated forms and are encompassed within the scope of the present invention. Certain compounds of Formula (I) or Formula (II) described herein may exist in multiple crystalline or amorphous forms. In general, all physical forms are equivalent for the uses contemplated by the present disclosure and are intended to be within the scope of the present disclosure.

The term "solvate" refers to forms of the compound that are associated with a solvent, usually by a solvolysis reaction. This physical association may include hydrogen bonding. Conventional solvents include water, methanol, ethanol, acetic acid, dimethylsulfoxide (DMSO), tetrahydrofuran (THF), diethyl ether, and the like. The compounds described herein may be prepared, e.g., in crystalline form, and may be solvated. Suitable solvates include pharmaceutically acceptable solvates and further include both stoichiometric solvates and non-stoichiometric solvates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R·x $H_2O$, wherein R is the compound and wherein x is a number greater than 0.

The term "tautomer" as used herein refers to compounds that are interchangeable forms of a compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Tautomeric forms may be relevant to the attainment of the optimal chemical reactivity and biological activity of a compound of interest.

The symbol "∿∿" as used herein refers to a connection to an entity, e.g., a polymer (e.g., hydrogel-forming polymer such as alginate) or an implantable element (e.g., a device or material). The connection represented by "∿∿" may refer to direct attachment to the entity, e.g., a polymer or an implantable element, may refer to linkage to the entity through an attachment group. An "attachment group," as described herein, refers to a moiety for linkage of a compound of Formula (II) to an entity (e.g., a polymer or an implantable element as described herein), and may comprise any attachment chemistry known in the art. A listing of exemplary attachment groups is outlined in *Bioconjugate Techniques* ($3^{rd}$ ed, Greg T. Hermanson, Waltham, MA: Elsevier, Inc, 2013), which is incorporated herein by reference in its entirety. In some embodiments, an attachment group comprises alkyl, alkenyl, alkynyl, heteroalkyl, cycloalkyl, heterocyclyl, aryl, heteroaryl, —C(O)—, —OC(O)—, —N($R^C$)—, —N($R^C$)C(O)—, —C(O)N($R^C$)—, —N($R^C$)N($R^D$)—, —NCN—, —C(=N($R^C$)($R^D$))O—, —S—, —$S(O)_x$—, —$OS(O)_x$—, —N($R^C$)$S(O)_x$—, —$S(O)_x$N($R^C$)—, —P($R^F$)—, —$Si(OR^A)_2$—, —Si($R^G$)($OR^A$)—, —B($OR^A$)—, or a metal, wherein each of $R^A$, $R^C$, $R^D$, $R^F$, $R^G$, x and y is independently as described herein. In some embodiments, an attachment group comprises an amine, ketone, ester, amide, alkyl, alkenyl, alkynyl, or thiol. In some embodiments, an attachment group is a cross-linker. In some embodiments, the attachment group is —C(O)($C_1$-$C_6$-alkylene)-, wherein alkylene is substituted with $R^1$, and $R^1$ is as described herein. In some embodiments, the attachment group is —C(O)($C_1$-$C_6$-alkylene)-, wherein alkylene is substituted with 1-2 alkyl groups (e.g., 1-2 methyl groups). In some embodiments, the attachment group is —C(O)$C(CH_3)_2$—. In some embodiments, the attachment group is —C(O)(methylene)-, wherein alkylene is substituted with 1-2 alkyl groups (e.g., 1-2 methyl groups). In some embodiments, the attachment group is —C(O)CH($CH_3$)—. In some embodiments, the attachment group is —C(O)C($CH_3$)—.

Compounds

The present invention features a compound of Formula (I):

$$A\text{-}L^1\text{-}M\text{-}L^2\text{-}P\text{-}L^3\text{-}Z \quad (I)$$

or a pharmaceutically acceptable salt thereof, wherein:

A is hydrogen, alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)C(O)($C_1$-$C_6$-alkylene)-, —N($R^C$)C(O)($C_1$-$C_6$-alkenylene)-, —N($R^C$)N($R^D$)—, —NCN—, —C(=N($R^C$)($R^D$))O—, —S—, —$S(O)_x$—, —$OS(O)_x$—, —N($R^C$)$S(O)_x$—, —$S(O)_x$N($R^C$)—, —$P(R^F)_y$—, —$Si(OR^A)_2$—, —Si($R^G$)($OR^A$)—, —B($OR^A$)—, or a metal, wherein each alkyl, alkenyl, alkynyl, alkylene, alkenylene, heteroalkyl, cycloalkyl, heterocyclyl, aryl, and heteroaryl is linked to an attachment group (e.g., an attachment group defined herein) and is optionally substituted by one or more $R^1$;

each of $L^1$ and $L^3$ is independently a bond, alkyl, or heteroalkyl, wherein each alkyl and heteroalkyl is optionally substituted by one or more $R^2$;

$L^2$ is a bond;

M is absent, alkyl, heteroalkyl, cycloalkyl, heterocyclyl, aryl, or heteroaryl, each of which is optionally substituted by one or more $R^3$;

P is absent, cycloalkyl, heterocycyl, or heteroaryl, each of which is optionally substituted by one or more $R^4$;

Z is hydrogen, alkyl, alkenyl, alkynyl, heteroalkyl, —$OR^A$, —C(O)$R^A$, —C(O)$OR^A$, —C(O)N($R^C$)($R^D$), —N($R^C$)C(O)$R^A$, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$;

or $R^C$ and $R^D$, taken together with the nitrogen atom to which they are attached, form a ring (e.g., a 5-7 membered ring), optionally substituted with one or more $R^6$;

each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —C(O)$OR^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), $SR^{E1}$, $S(O)_xR^{E1}$, —$OS(O)_xR^{E1}$, —N($R^{C1}$)$S(O)_xR^{E1}$, —$S(O)_x$N($R^{C1}$)($R^{D1}$), —$P(R^{F1})_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

In some embodiments, the compound of Formula (I) is a compound of Formula (I-a):

(I-a)

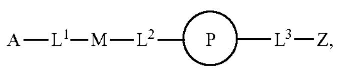

or a pharmaceutically acceptable salt thereof, wherein:

A is hydrogen, alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)C(O)($C_1$-$C_6$-alkylene)-, —N($R^C$)C(O)($C_1$-$C_6$-alkenylene)-, —N($R^C$)N($R^D$)—, —NCN—, —C(=N($R^C$)($R^D$))O—, —S—, —$S(O)_x$—, —$OS(O)_x$—, —N($R^C$)$S(O)_x$—, —$S(O)_x$N($R^C$)—, —$P(R^F)_y$—, —$Si(OR^A)_2$—, —Si ($R^G$)($OR^A$)—, —B($OR^A$)—, or a metal, wherein each alkyl, alkenyl, alkynyl, alkylene, alkenylene, heteroalkyl, cycloalkyl, heterocyclyl, aryl, and heteroaryl is linked to an attachment group (e.g., an attachment group defined herein) and is optionally substituted by one or more $R^1$;

each of $L^1$ and $L^3$ is independently a bond, alkyl, or heteroalkyl, wherein each alkyl and heteroalkyl is optionally substituted by one or more $R^2$;

$L^2$ is a bond;

M is absent, alkyl, heteroalkyl, cycloalkyl, heterocyclyl, aryl, or heteroaryl, each of which is optionally substituted by one or more $R^3$;

P is heteroaryl optionally substituted by one or more $R^4$;

Z is alkyl, alkenyl, alkynyl, heteroalkyl, cycloalkyl, heterocyclyl, aryl, or heteroaryl, each of which is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$;

or $R^C$ and $R^D$, taken together with the nitrogen atom to which they are attached, form a ring (e.g., a 5-7 membered ring), optionally substituted with one or more $R^6$;

each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —C(O)$OR^{A1}$, —C(O)$R^{B1}$, —OC(O)$R^{B1}$, —N($R^{C1}$)($R^{D1}$), N($R^{C1}$)C(O)$R^{B1}$, —C(O)N($R^{C1}$), $SR^{E1}$, $S(O)_xR^{E1}$, —$OS(O)_xR^{E1}$, —N($R^{C1}$)$S(O)_R{}^{E1}$, —$S(O)_x$N($R^{C1}$)($R^{D1}$), —P($R^{F1}$)$_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

In some embodiments, for Formulas (I) and (I-a), A is hydrogen, alkyl, alkenyl, alkynyl, heteroalkyl, cycloalkyl, heterocyclyl, aryl, heteroaryl, —$OR^A$, —C(O)$OR^A$, —C(O)$R^B$, —OC(O)$R^B$, —N($R^C$)($R^D$), —N($R^C$)C(O)$R^B$, —N($R^C$)C(O)($C_1$-$C_6$-alkyl), or —N($R^C$)C(O)($C_1$-$C_6$-alkenyl). In some embodiments, A is hydrogen, alkyl, alkenyl, alkynyl, heteroalkyl, cycloalkyl, heterocyclyl, aryl, heteroaryl, —$OR^A$, —C(O)$OR^A$, —C(O)$R^B$, —OC(O)$R^B$, or N($R^C$)($R^D$). In some embodiments, A is hydrogen, alkyl, alkenyl, alkynyl, heteroalkyl, —$OR^A$, —C(O)$OR^A$, —C(O)$R^B$, —OC(O)$R^B$, or N($R^C$)($R^D$). In some embodiments, A is hydrogen, alkyl, —$OR^A$, —C(O)$OR^A$, —C(O)$R^B$, —OC(O)$R^B$, or N($R^C$)($R^D$). In some embodiments, A is hydrogen. In some embodiments, A is —N($R^C$)($R^D$), —N($R^C$)C(O)$R^B$, —N($R^C$)C(O)($C_1$-$C_6$-alkyl), or —N($R^C$)C(O)($C_1$-$C_6$-alkenyl). In some embodiments, A is —N($R^C$)—. In some embodiments, A is —N($R^C$)($R^D$), and each $R^C$ and $R^D$ is independently hydrogen or alkyl. In some embodiments, A is —$NH_2$. In some embodiments, A is —N($R^C$)C(O)($C_1$-$C_6$-alkyl), wherein alkyl is substituted with one or more $R^1$. In some embodiments, A is —N($R^C$)C(O)($C_1$-$C_6$-alkenyl), wherein alkenyl is substituted with one or more $R^1$. In some embodiments, $R^1$ is $C_1$-$C_6$ alkyl (e.g., methyl). In some embodiments, A is —NHC(O)C($CH_3$)(=$CH_2$). In some embodiments, A is —$NH_2$ or NHC(O)C($CH_3$)(=$CH_2$).

In some embodiments, for Formulas (I) and (I-a), $L^1$ is a bond, alkyl, or heteroalkyl. In some embodiments, $L^1$ is a bond or alkyl. In some embodiments, $L^1$ is a bond. In some embodiments, $L^1$ is alkyl. In some embodiments, $L^1$ is $C_1$-$C_6$ alkyl. In some embodiments, $L^1$ is —$CH_2$—, —CH($CH_3$)—, —$CH_2CH_2CH_2$, or —$CH_2CH_2$—. In some embodiments, $L^1$ is —$CH_2$— or —$CH_2CH_2$—.

In some embodiments, for Formulas (I) and (I-a), $L^3$ is a bond, alkyl, or heteroalkyl. In some embodiments, $L^3$ is a bond. In some embodiments, $L^3$ is alkyl. In some embodiments, $L^3$ is $C_1$-$C_{12}$ alkyl. In some embodiments, $L^3$ is $C_1$-$C_6$ alkyl. In some embodiments, $L^3$ is —$CH_2$—. In some embodiments, $L^3$ is heteroalkyl. In some embodiments, $L^3$ is $C_1$-$C_{12}$ heteroalkyl, optionally substituted with one or more $R^2$ (e.g., oxo). In some embodiments, $L^3$ is $C_1$-$C_6$ heteroalkyl, optionally substituted with one or more $R^2$ (e.g., oxo). In some embodiments, $L^3$ is —C(O)$OCH_2$—, —$CH_2$($OCH_2CH_2$)$_2$—, —$CH_2$($OCH_2CH_2$)$_3$—, $CH_2CH_2O$—, or —$CH_2O$—. In some embodiments, $L^3$ is —$CH_2O$—.

In some embodiments, for Formulas (I) and (I-a), M is absent, alkyl, heteroalkyl, aryl, or heteroaryl. In some embodiments, M is heteroalkyl, aryl, or heteroaryl. In some embodiments, M is absent. In some embodiments, M is alkyl (e.g., $C_1$-$C_6$ alkyl). In some embodiments, M is —$CH_2$—. In some embodiments, M is heteroalkyl (e.g., $C_1$-$C_6$ heteroalkyl). In some embodiments, M is (—$OCH_2CH_2$—)z, wherein z is an integer selected from 1 to 10. In some embodiments, z is an integer selected from 1 to 5. In some embodiments, M is —$OCH_2CH_2$—, (—$OCH_2CH_2$—)$_2$, (—$OCH_2CH_2$—)$_3$, (—$OCH_2CH_2$—)$_4$, or (—$OCH_2CH_2$—)$_5$. In some embodiments, M is —$OCH_2CH_2$—, (—$OCH_2CH_2$—)$_2$, (—$OCH_2CH_2$—)$_3$, or (—$OCH_2CH_2$—)$_4$. In some embodiments, M is (—$OCH_2CH_2$—)$_3$. In some embodiments, M is aryl. In some embodiments, M is phenyl. In some embodiments, M is unsubstituted phenyl. In some embodiments, M is

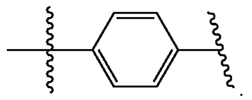

In some embodiments, M is phenyl substituted with $R^7$ (e.g., 1 $R^7$). In some embodiments, M is

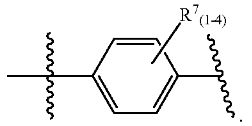

In some embodiments, $R^7$ is $CF_3$.

In some embodiments, for Formulas (I) and (I-a), P is absent, heterocyclyl, or heteroaryl. In some embodiments, P is absent. In some embodiments, for Formulas (I) and (I-a), P is a tricyclic, bicyclic, or monocyclic heteroaryl. In some embodiments, P is a monocyclic heteroaryl. In some embodiments, P is a nitrogen-containing heteroaryl. In some embodiments, P is a monocyclic, nitrogen-containing heteroaryl. In some embodiments, P is a 5-membered heteroaryl. In some embodiments, P is a 5-membered nitrogen-containing heteroaryl. In some embodiments, P is tetrazolyl, imidazolyl, pyrazolyl, or triazolyl, pyrrolyl, oxazolyl, or thiazolyl. In some embodiments, P is tetrazolyl, imidazolyl, pyrazolyl, or triazolyl, or pyrrolyl. In some embodiments, P is imidazolyl. In some embodiments, P is

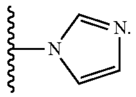 [SMILES: *n1ccnc1]

In some embodiments, P is triazolyl. In some embodiments, P is 1,2,3-triazolyl. In some embodiments, P is

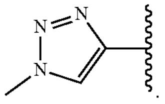 [SMILES: *c1cn(C)nn1]

In some embodiments, P is heterocyclyl. In some embodiments, P is a 5-membered heterocyclyl or a 6-membered heterocyclyl. In some embodiments, P is imidazolidinonyl. In some embodiments, P is

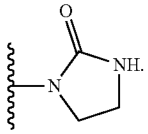 [SMILES: *N1CCNC1=O]

In some embodiments, P is thiomorpholinyl-1,1-dioxidyl. In some embodiments, P is

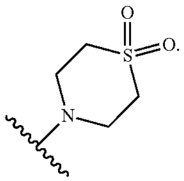 [SMILES: *N1CCS(=O)(=O)CC1]

In some embodiments, for Formulas (I) and (I-a), Z is alkyl, heteroalkyl, cycloalkyl, heterocyclyl, aryl, or heteroaryl. In some embodiments, Z is heterocyclyl. In some embodiments, Z is monocyclic or bicyclic heterocyclyl. In some embodiments, Z is an oxygen-containing heterocyclyl. In some embodiments, Z is a 4-membered heterocyclyl, 5-membered heterocyclyl, or 6-membered heterocyclyl. In some embodiments, Z is a 6-membered heterocyclyl. In some embodiments, Z is a 6-membered oxygen-containing heterocyclyl. In some embodiments, Z is tetrahydropyranyl. In some embodiments, Z is

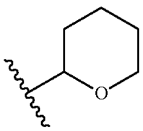 , 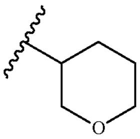 , or 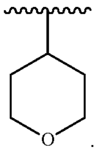 .

In some embodiments, Z is a 4-membered oxygen-containing heterocyclyl. In some embodiments, Z is

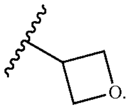

In some embodiments, Z is a bicyclic oxygen-containing heterocyclyl. In some embodiments, Z is phthalic anhydridyl. In some embodiments, Z is a sulfur-containing heterocyclyl. In some embodiments, Z is a 6-membered sulfur-containing heterocyclyl. In some embodiments, Z is a 6-membered heterocyclyl containing a nitrogen atom and a sulfur atom. In some embodiments, Z is thiomorpholinyl-1,1-dioxidyl. In some embodiments, Z is

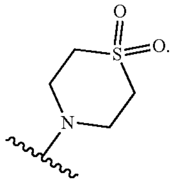 [SMILES: *N1CCS(=O)(=O)CC1]

In some embodiments, Z is a nitrogen-containing heterocyclyl. In some embodiments, Z is a 6-membered nitrogen-containing heterocyclyl. In some embodiments, Z is

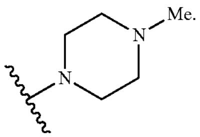 [SMILES: *N1CCN(C)CC1]

In some embodiments, Z is a bicyclic heterocyclyl. In some embodiments, Z is a bicyclic nitrogen-containing heterocyclyl, optionally substituted with one or more $R^5$. In some embodiments, Z is 2-oxa-7-azaspiro[3.5]nonanyl. In some embodiments, Z is

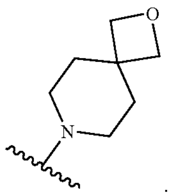 [SMILES: *N1CCC2(CC1)COC2]

In some embodiments, Z is 1-oxa-3,8-diazaspiro[4.5]decan-2-one. In some embodiments, Z is

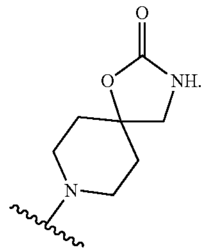 [SMILES: *N1CCC2(CC1)CNC(=O)O2]

In some embodiments, for Formulas (I) and (I-a), Z is aryl. In some embodiments, Z is monocyclic aryl. In some embodiments, Z is phenyl. In some embodiments, Z is monosubstituted phenyl (e.g., with 1 $R^5$). In some embodiments, Z is monosubstituted phenyl, wherein the 1 $R^5$ is a nitrogen-containing group. In some embodiments, Z is monosubstituted phenyl, wherein the 1 $R^5$ is $NH_2$. In some embodiments, Z is monosubstituted phenyl, wherein the 1 $R^5$ is an oxygen-containing group. In some embodiments, Z is monosubstituted phenyl, wherein the 1 $R^5$ is an oxygen-containing heteroalkyl. In some embodiments, Z is monosubstituted phenyl, wherein the 1 $R^5$ is $OCH_3$. In some embodiments, Z is monosubstituted phenyl, wherein the 1 $R^5$ is in the ortho position. In some embodiments, Z is monosubstituted phenyl, wherein the 1 $R^5$ is in the meta position. In some embodiments, Z is monosubstituted phenyl, wherein the 1 $R^5$ is in the para position.

In some embodiments, for Formulas (I) and (I-a), Z is alkyl. In some embodiments, Z is $C_1$-$C_{12}$ alkyl. In some embodiments, Z is $C_1$-$C_{10}$ alkyl. In some embodiments, Z is $C_1$-$C_8$ alkyl. In some embodiments, Z is $C_1$-$C_8$ alkyl substituted with 1-5 $R^5$. In some embodiments, Z is $C_1$-$C_8$ alkyl substituted with 1 $R^5$. In some embodiments, Z is $C_1$-$C_8$ alkyl substituted with 1 $R^5$, wherein $R^5$ is alkyl, heteroalkyl, halogen, oxo, —$OR^{A1}$, —$C(O)OR^{A1}$, —$C(O)R^{B1}$, —$OC(O)R^{B1}$, or —$N(R^{C1})(R^{D1})$. In some embodiments, Z is $C_1$-$C_8$ alkyl substituted with 1 $R^5$, wherein $R^5$ is —$OR^{A1}$ or —$C(O)OR^{A1}$. In some embodiments, Z is $C_1$-$C_8$ alkyl substituted with 1 $R^5$, wherein $R^5$ is —$OR^{A1}$ or —C(O)OH. In some embodiments, Z is —$CH_3$.

In some embodiments, for Formulas (I) and (I-a), Z is heteroalkyl. In some embodiments, Z is $C_1$-$C_{12}$ heteroalkyl. In some embodiments, Z is $C_1$-$C_{10}$ heteroalkyl. In some embodiments, Z is $C_1$-$C_8$ heteroalkyl. In some embodiments, Z is $C_1$-$C_6$ heteroalkyl. In some embodiments, Z is a nitrogen-containing heteroalkyl optionally substituted with one or more $R^5$. In some embodiments, Z is a nitrogen and sulfur-containing heteroalkyl substituted with 1-5 $R^5$. In some embodiments, Z is N-methyl-2-(methylsulfonyl) ethan-1-aminyl.

In some embodiments, Z is —$OR^A$ or —$C(O)OR^A$. In some embodiments, Z is —$OR^A$ (e.g., —OH or —$OCH_3$). In some embodiments, Z is —$OCH_3$. In some embodiments, Z is —$C(O)OR^A$ (e.g., —C(O)OH).

In some embodiments, Z is hydrogen.

In some embodiments, $L^2$ is a bond and P and $L^3$ are independently absent. In some embodiments, $L^2$ is a bond, P is heteroaryl, $L^3$ is a bond, and Z is hydrogen. In some embodiments, P is heteroaryl, $L^3$ is heteroalkyl, and Z is alkyl.

In some embodiments, the compound of Formula (I) is a compound of Formula (I-b):

(I-b)

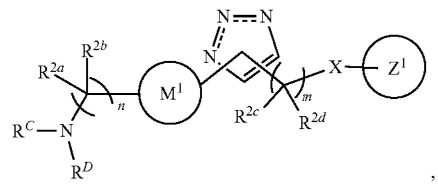

or a pharmaceutically acceptable salt thereof, wherein Ring $M^1$ is cycloalkyl, heterocyclyl, aryl, or heteroaryl, each of which is optionally substituted with 1-5 $R^3$; Ring $Z^1$ is cycloalkyl, heterocyclyl, aryl or heteroaryl, optionally substituted with 1-5 $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl, or each of $R^{2a}$ and $R^{2b}$ or $R^{2c}$ and $R^{2d}$ is taken together to form an oxo group; X is absent, $N(R^{10})(R^{11})$, O, or S; each of $R^C$ and $R^D$ is independently hydrogen, alkyl, alkenyl, alkynyl, or heteroalkyl, wherein each of alkyl, alkenyl, alkynyl, or heteroalkyl is optionally substituted with 1-6 $R^6$; each $R^3$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, $N(R^{C1})C(O)R^{B1}$, —$C(O)N(R^{C1})$, $SR^{E1}$, cycloalkyl, heterocyclyl, aryl, or heteroaryl; each of $R^{10}$ and $R^{11}$ is independently hydrogen, alkyl, alkenyl, alkynyl, heteroalkyl, —$C(O)OR^{A1}$, —$C(O)R^{B1}$, —$OC(O)R^{B1}$, —$C(O)N(R^{C1})$, cycloalkyl, heterocyclyl, aryl, or heteroaryl; each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, cyano, oxo, hydroxyl, cycloalkyl, or heterocyclyl; and each m and n is independently 1, 2, 3, 4, 5, or 6. In some embodiments, for each $R^3$, $R^5$, and $R^6$, each alkyl, alkenyl, alkynyl, heteroalkyl, cycloalkyl, heterocyclyl, aryl, or heteroaryl is optionally and independently substituted with halogen, oxo, cyano, cycloalkyl, or heterocyclyl.

In some embodiments, the compound of Formula (I-b) is a compound of Formula (I-b-i):

(I-b-i)

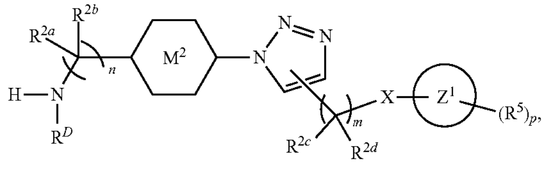

or a pharmaceutically acceptable salt thereof, wherein Ring $M^2$ is aryl or heteroaryl optionally substituted with one or more $R^3$; Ring $Z^2$ is cycloalkyl, heterocyclyl, aryl, or heteroaryl; each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group; X is absent, O, or S; $R^D$ is hydrogen, alkyl, alkenyl, alkynyl, or heteroalkyl, wherein each of alkyl, alkenyl, alkynyl, and heteroalkyl is optionally substituted with 1-6 $R^6$; each $R^3$, $R^5$ and $R^6$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with halogen, or two $R^5$ are taken together to form a 5-6 membered ring fused to Ring $Z^2$; each $R^{A1}$ and $R^{B1}$ is independently hydrogen, alkyl, or heteroalkyl; and m and n are each independently 1, 2, 3, 4, 5, or 6; p is 0, 1, 2, 3, 4, 5, or 6.

In some embodiments, the compound of Formula (I-b-i) is a compound of Formula (I-b-ii):

(I-b-ii)

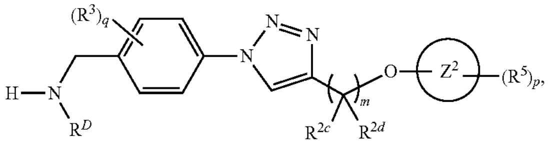

or a pharmaceutically acceptable salt thereof, wherein Ring $Z^2$ is cycloalkyl, heterocyclyl, aryl or heteroaryl; $R^D$ is hydrogen, alkyl, alkenyl, alkynyl, or heteroalkyl, wherein each of alkyl, alkenyl, alkynyl, and heteroalkyl is optionally substituted with 1-6 $R^6$; each of $R^{2c}$ and $R^{2d}$ is independently hydrogen, alkyl, or heteroalkyl, or $R^{2c}$ and $R^{2d}$ and taken together to form an oxo group; each $R^3$, $R^5$ and $R^6$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with halogen; each $R^{A1}$ and $R^{B1}$ is independently hydrogen, alkyl, or heteroalkyl; and each of p and q is independently 0, 1, 2, 3, 4, 5, or 6.

In some embodiments, the compound of Formula (I-b-ii) is a compound of Formula (I-b-iii):

(I-b-iii)

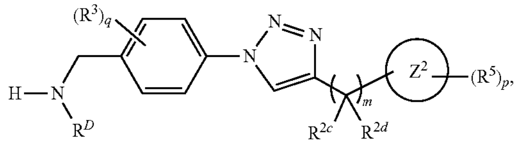

or a pharmaceutically acceptable salt thereof, wherein Ring $Z^2$ is cycloalkyl, heterocyclyl, aryl or heteroaryl; $R^D$ is hydrogen, alkyl, alkenyl, alkynyl, or heteroalkyl, wherein each of alkyl, alkenyl, alkynyl, and heteroalkyl is optionally substituted with 1-6 $R^6$; each of $R^{2c}$ and $R^{2d}$ is independently hydrogen, alkyl, or heteroalkyl, or $R^{2c}$ and $R^{2d}$ are taken together to form an oxo group; each $R^3$, $R^5$ and $R^6$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with halogen; each $R^{A1}$ and $R^{B1}$ is independently hydrogen, alkyl, or heteroalkyl; m is 1, 2, 3, 4, 5, or 6; and each of p and q is independently 0, 1, 2, 3, 4, 5, or 6. In some embodiments, the compound of Formula (I-a) is a compound of Formula (I-c):

(I-c)

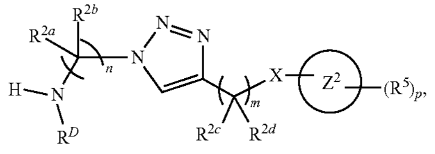

or a pharmaceutically acceptable salt thereof, wherein Ring $Z^2$ is cycloalkyl, heterocyclyl, aryl or heteroaryl; X is absent, O, or S; $R^D$ is hydrogen, alkyl, alkenyl, alkynyl, or heteroalkyl, wherein each of alkyl, alkenyl, alkynyl, and heteroalkyl is optionally substituted with 1-6 $R^6$; each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group; each $R^5$ and $R^6$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; and each of m and n is independently 1, 2, 3, 4, 5, or 6; p is 0, 1, 2, 3, 4, 5, or 6.

In some embodiments, the compound of Formula (I-a) is a compound of Formula (I-d):

(I-d)

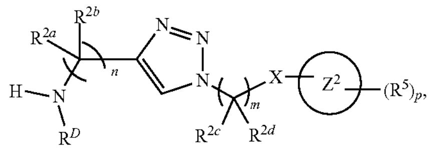

or a pharmaceutically acceptable salt thereof, wherein Ring $Z^2$ is cycloalkyl, heterocyclyl, aryl or heteroaryl; X is absent, O, or S; $R^D$ is hydrogen, alkyl, alkenyl, alkynyl, or heteroalkyl, wherein each of alkyl, alkenyl, alkynyl, and heteroalkyl is optionally substituted with 1-6 $R^6$; each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group; each $R^5$ and $R^6$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; and each of m and n is independently 1, 2, 3, 4, 5, or 6; p is 0, 1, 2, 3, 4, 5, or 6.

In some embodiments, the compound of Formula (I) is a compound of Formula (I-e):

(I-e)

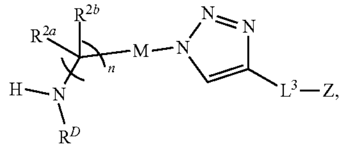

or a pharmaceutically acceptable salt thereof, wherein M is a bond, alkyl or aryl, each of which is optionally substituted with one or more $R^3$; $L^3$ is a bond, alkyl or heteroalkyl optionally substituted with one or more $R^2$; Z is hydrogen, alkyl, heteroalkyl, cycloalkyl, heterocyclyl, aryl, heteroaryl, or —$OR^4$, each of which is optionally substituted with one or more $R^5$; $R^4$ is hydrogen; $R^D$ is hydrogen, alkyl, alkenyl, alkynyl, or heteroalkyl, wherein each of alkyl, alkenyl, alkynyl, and heteroalkyl is optionally substituted with 1-6 $R^6$; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, $R^5$, and $R^6$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; and n is independently 1, 2, 3, 4, 5, or 6.

In some embodiments, the compound of Formula (I-e) is a compound of Formula (I-e-i):

(I-e-i)

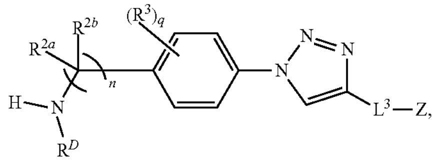

or a pharmaceutically acceptable salt thereof, wherein $L^3$ is a bond, alkyl or heteroalkyl, each of which is optionally substituted with one or more $R^2$; Z is hydrogen, alkyl, heteroalkyl, or —$OR^A$, each of which is optionally substituted with one or more $R^5$; $R^A$ is hydrogen; $R^D$ is hydrogen, alkyl, alkenyl, alkynyl, or heteroalkyl, wherein each of alkyl, alkenyl, alkynyl, and heteroalkyl is optionally substituted with 1-6 $R^6$; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, $R^6$, and $R^6$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; and n is independently 1, 2, 3, 4, 5, or 6.

In some embodiments, the compound of Formula (I-a) is a compound of Formula (I-f):

(I-f)

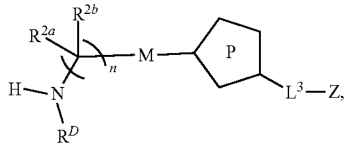

or a pharmaceutically acceptable salt thereof, wherein M is alkyl optionally substituted with one or more $R^3$; Ring P is heteroaryl optionally substituted with one or more $R^4$; $L^3$ is alkyl or heteroalkyl optionally substituted with one or more $R^2$; Z is alkyl, heteroalkyl, cycloalkyl, heterocyclyl, aryl, or heteroaryl, each of which is optionally substituted with one or more $R^5$; $R^D$ is hydrogen, alkyl, alkenyl, alkynyl, or heteroalkyl, wherein each of alkyl, alkenyl, alkynyl, and heteroalkyl is optionally substituted with 1-6 $R^6$; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, $R^4$, $R^5$, and $R^6$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; and n is independently 1, 2, 3, 4, 5, or 6.

In some embodiments, the compound of Formula (I) is a compound of Formula (I-g):

(I-g)

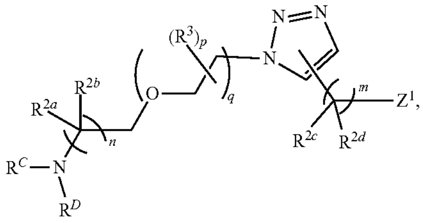

or a pharmaceutically acceptable salt thereof, wherein $Z^1$ is alkyl, alkenyl, alkynyl, heteroalkyl, cycloalkyl, heterocyclyl, aryl, or heteroaryl, each of which is optionally substituted with 1-5 $R^5$; each of $R^C$ and $R^D$ is independently hydrogen, alkyl, alkenyl, alkynyl, or heteroalkyl, wherein each of alkyl, alkenyl, alkynyl, or heteroalkyl is optionally substituted with 1-6 $R^6$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; each of $R^3$, $R^5$, and $R^6$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; and q is an integer from 0 to 25.

In some embodiments, the compound of Formula (I-g) is a compound of Formula (I-g-i):

(I-g-i)

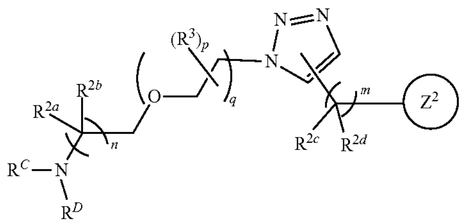

, or a pharmaceutically acceptable salt thereof, wherein Ring $Z^2$ is cycloalkyl, heterocyclyl, aryl, or heteroaryl, each of which is optionally substituted with 1-5 $R^5$; each of $R^C$ and $R^D$ is independently hydrogen, alkyl, alkenyl, alkynyl, or heteroalkyl, wherein each of alkyl, alkenyl, alkynyl, or heteroalkyl is optionally substituted with 1-6 $R^6$; each of $R^{2a}$, $R^{2b}$, $R^{2c}$, and $R^{2d}$ is independently hydrogen, alkyl, heteroalkyl, halo; or $R^{2a}$ and $R^{2b}$ or $R^{2c}$ and $R^{2d}$ are taken together to form an oxo group; each of $R^3$, $R^5$, and $R^6$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; and o and p are each independently 0, 1, 2, 3, 4, or 5; q is an integer from 0 to 25.

In some embodiments, the compound of Formula (I-g-i) is a compound of Formula (I-g-ii):

(I-g-ii)

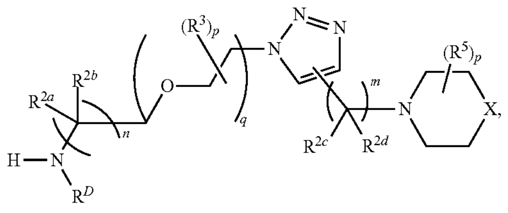

or a pharmaceutically acceptable salt thereof, wherein X is C(R')(R"), N(R'), or $S(O)_x$; each of R' and R" is independently hydrogen, alkyl, halogen, or cycloalkyl; each of $R^{2a}$, $R^{2b}$, $R^{2c}$, and $R^{2d}$ is independently hydrogen, alkyl, heteroalkyl, or halo; or $R^{2a}$ and $R^{2b}$ or $R^{2c}$ and $R^{2d}$ are taken together to form an oxo group; $R^D$ is hydrogen, alkyl, alkenyl, alkynyl, or heteroalkyl, wherein each of alkyl, alkenyl, alkynyl, and heteroalkyl is optionally substituted with 1-6

$R^6$; each of $R^3$ $R^5$, and $R^6$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; p is 0, 1, 2, 3, 4, or 5; and q is an integer from 0 to 25; x is 0, 1, or 2.

In some embodiments, the compound is a compound of Formula (I). In some embodiments of Formula (I), $L^2$ is a bond and P and $L^3$ are independently absent.

In some embodiments, the compound is a compound of Formula (I), P is absent, $L^1$ is —$NHCH_2$, $L^2$ is a bond, M is aryl (e.g., phenyl), $L^3$ is —$CH_2O$, and Z is heterocyclyl (e.g., a nitrogen-containing heterocyclyl, e.g., thiomorpholinyl-1, 1-dioxide). In some embodiments, A is hydrogen or C(O)C(=$CH_2$)$CH_3$. In some embodiments, the compound of Formula (I) is Compound 213 or 232.

In some embodiments of Formula (I), P is absent, $L^1$ is —$NHCH_2$, $L^2$ is a bond, M is absent, $L^3$ is a bond, and Z is heterocyclyl (e.g., an oxygen-containing heterocyclyl, e.g., tetrahydropyranyl, tetrahydrofuranyl, oxetanyl, or oxiranyl). In some embodiments, A is hydrogen or C(O)C(=$CH_2$)$CH_3$. In some embodiments, the compound of Formula (I) is Compound 202 or 221

In some embodiments, the compound is a compound of Formula (I-a). In some embodiments of Formula (I-a), $L^2$ is a bond, P is heteroaryl, $L^3$ is a bond, and Z is hydrogen. In some embodiments, P is heteroaryl, $L^3$ is heteroalkyl, and Z is alkyl. In some embodiments, $L^2$ is a bond, P is heteroaryl, $L^3$ is a bond, and Z is hydrogen. In some embodiments, P is heteroaryl, $L^3$ is heteroalkyl, and Z is alkyl.

In some embodiments, the compound is a compound of Formula (I-b-i). In some embodiments of Formula (I-b-i), each of $R^{2a}$ and $R^{2b}$ is independently hydrogen or $CH_3$, each of $R^{2c}$ and $R^{2d}$ is independently hydrogen, m is 1 or 2, n is 1, X is O, p is 0, $M^2$ is phenyl optionally substituted with one or more $R^3$, $R^3$ is —$CF_3$, and $Z^2$ is heterocyclyl (e.g., an oxygen-containing heterocyclyl, e.g., tetrahydropyranyl, tetrahydrofuranyl, oxetanyl, or oxiranyl). In some embodiments, $R^D$ is hydrogen or C(O)C(=$CH_2$)$CH_3$. In some embodiments, the compound of Formula (I-b-i) is Compound 203, Compound 204, Compound 205, Compound 206, or Compound 208. In some embodiments, the compound of Formula (I-b-i) is Compound 222, Compound 223, Compound 224, Compound 225 or Compound 227.

In some embodiments, the compound is a compound of Formula (I-b-iii). In some embodiments of Formula (I-b-iii), each of $R^{2c}$ and $R^{2d}$ is independently hydrogen, m is 1, p is 1, q is 0, $R^5$ is —$CH_3$, and $Z^2$ is heterocyclyl (e.g., a nitrogen-containing heterocyclyl, e.g., piperazinyl). In some embodiments, $R^D$ is hydrogen or C(O)C(=$CH_2$)$CH_3$. In some embodiments, the compound of Formula (I-b-iii) is Compound 210. In some embodiments, the compound of Formula (I-b-iii) is Compound 229.

In some embodiments, the compound is a compound of Formula (I-c). In some embodiments of Formula (I-c), each of $R^{2a}$, $R^{2b}$, $R^{2c}$, and $R^{2d}$ is independently hydrogen, m is 1, n is 3, X is O, p is 0, and $Z^2$ is heterocyclyl (e.g., an oxygen-containing heterocyclyl, e.g., tetrahydropyranyl, tetrahydrofuranyl, oxetanyl, or oxiranyl). In some embodiments, $R^D$ is hydrogen or C(O)C(=$CH_2$)$CH_3$. In some embodiments, the compound of Formula (I-c) is Compound 207 or Compound 211. In some embodiments, the compound of Formula (I-c) is Compound 226 or Compound 230.

In some embodiments, the compound is a compound of Formula (I-e-i). In some embodiments of Formula (I-e-i), each of $R^{2a}$ and $R^{2b}$ is independently hydrogen, n is 1, q is 0, $L^3$ is —$CH_2(OCH_2CH_2)_2$, and Z is —$OCH_3$. In some embodiments, $R^D$ is hydrogen or C(O)C(=$CH_2$)$CH_3$. In some embodiments, the compound of Formula (I-e-i) is Compound 209. In some embodiments, the compound of Formula (I-e-i) is Compound 228.

In some embodiments of Formula (I-e-i), each of $R^{2a}$ and $R^{2b}$ is independently hydrogen, n is 1, $L^3$ is a bond or —$CH_2$, and Z is hydrogen or —OH. In some embodiments, $R^D$ is hydrogen or C(O)C(=$CH_2$)$CH_3$. In some embodiments, the compound of Formula (I-e-i) is Compound 200 or 201. In some embodiments, the compound of Formula (I-e-i) is Compound 219 or 220.

In some embodiments, the compound is a compound of Formula (I-g). In some embodiments of Formula (I-g), each of $R^{2a}$, $R^{2b}$, $R^{2c}$, and $R^{2d}$ is independently hydrogen, m is 1, n is 2, q is 3, p is 0, $R^C$ is hydrogen, and $Z^1$ is heteroalkyl optionally substituted with $R^5$ (e.g., —$N(CH_3)(CH_2CH_2)S(O)_2CH_3$). In some embodiments, $R^D$ is hydrogen or C(O)C(=$CH_2$)$CH_3$. In some embodiments, the compound of Formula (I-g) is Compound 217. In some embodiments, the compound of Formula (I-g) is Compound 236.

In some embodiments, the compound is a compound of Formula (I-g-i). In some embodiments of Formula (I-g-i), each of $R^{2a}$, $R^{2b}$, $R^{2c}$, and $R^{2d}$ is independently hydrogen, m is 1, n is 2, q is 3, p is 0, $R^C$ is hydrogen, and $Z^2$ is heterocyclyl (e.g., an nitrogen-containing heterocyclyl, e.g., a nitrogen-containing spiro heterocyclyl, e.t., 2-oxa-7-azaspiro[3.5]nonanyl). In some embodiments, $R^D$ is hydrogen or C(O)C(=$CH_2$)$CH_3$. In some embodiments, the compound of Formula (I-g-i) is Compound 218. In some embodiments, the compound of Formula (I-g-i) is Compound 237.

In some embodiments, the compound is a compound of Formula (I-g-ii). In some embodiments of Formula (I-g-ii), each of $R^{2a}$, $R^{2b}$, $R^{2c}$, and $R^{2d}$ is independently hydrogen, m is 1, n is 2, q is 1, 2, 3, or 4, p is 0, and X is $S(O)_2$. In some embodiments of Formula (I-g-ii), each of $R^{2a}$ and $R^{2b}$ is independently hydrogen, m is 1, n is 2, q is 1, 2, or 4, p is 0, and X is $S(O)_2$. In some embodiments, $R^D$ is hydrogen or C(O)C(=$CH_2$)$CH_3$. In some embodiments, the compound of Formula (I-g-ii) is Compound 214, Compound 215, or Compound 216. In some embodiments, the compound of Formula (I-g-ii) is Compound 233, Compound 234, or Compound 235.

In some embodiments, the compound is a compound of Formula (I-b), (I-c), or (I-d). In some embodiments, the compound is a compound of Formula (I-b), (I-c), or (I-e). In some embodiments, the compound is a compound of Formula (I-b), (I-c), or (I-f). In some embodiments, the compound is a compound of Formula (I-b), (I-c), or (I-g).

In some embodiments, the compound of Formula (I) is not a compound disclosed in WO2012/112982, WO2012/167223, WO2014/153126, WO2016/019391, WO 2017/075630, US2012-0213708, US 2016-0030359 or US 2016-0030360.

In some embodiments, the compound of Formula (I) comprises a compound shown in Table 1, or a pharmaceutically acceptable salt thereof.

TABLE 1
| Exemplary compounds of Formula (I) | |
|---|---|
| Compound No. | Structure |
| 200 | 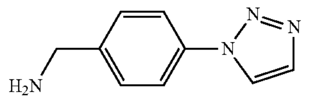 |
| 201 | 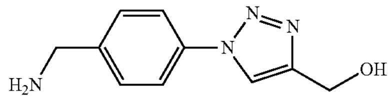 [SMILES: NCc1ccc(-n2cc(CO)nn2)cc1] |
| 202 | 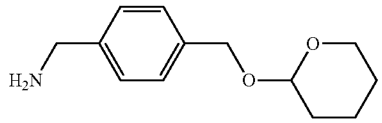 [SMILES: NCc1ccc(COC2CCCCO2)cc1] |
| 203 | 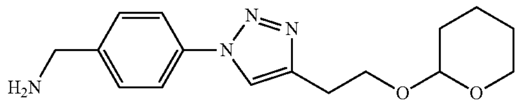 [SMILES: NCc1ccc(-n2cc(CCOC3CCCCO3)nn2)cc1] |
| 204 | 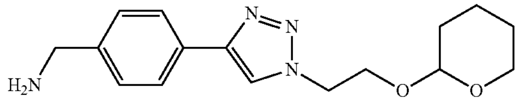 [SMILES: NCc1ccc(-c2cn(CCOC3CCCCO3)nn2)cc1] |
| 205 | 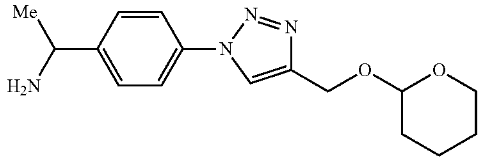 [SMILES: CC(N)c1ccc(-n2cc(COC3CCCCO3)nn2)cc1] |
| 206 | 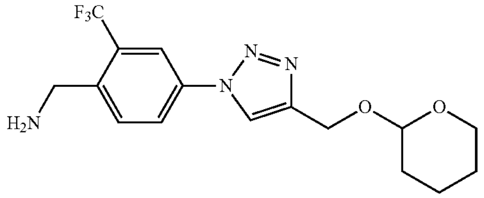 [SMILES: NCc1ccc(-n2cc(COC3CCCCO3)nn2)cc1C(F)(F)F] |
| 207 | 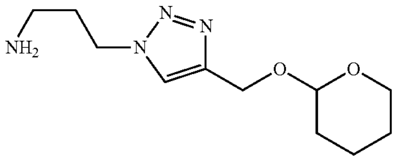 [SMILES: NCCCn1cc(COC2CCCCO2)nn1] |
| 208 | 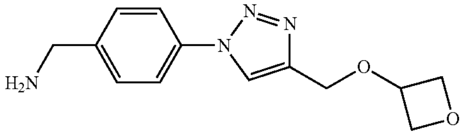 [SMILES: NCc1ccc(-n2cc(COC3COC3)nn2)cc1] |
| 209 | 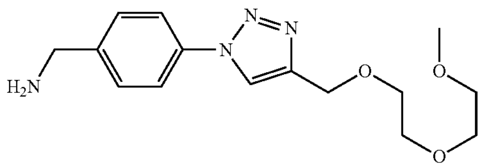 [SMILES: COCCOCCOCc1cn(-c2ccc(CN)cc2)nn1] |

TABLE 1-continued
| Compound No. | Structure |
|---|---|
| Exemplary compounds of Formula (I) | |
| 210 | 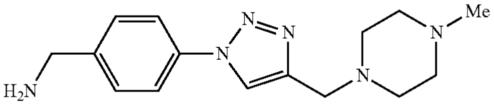 [SMILES: CN1CCN(Cc2cn(-c3ccc(CN)cc3)nn2)CC1] |
| 211 | 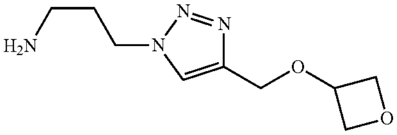 [SMILES: NCCCn1cc(COC2COC2)nn1] |
| 212 | 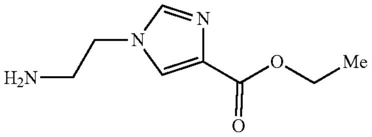 [SMILES: CCOC(=O)c1cn(CCN)cn1] |
| 213 | 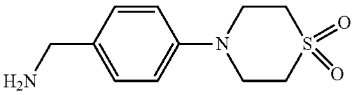 |
| 214 | 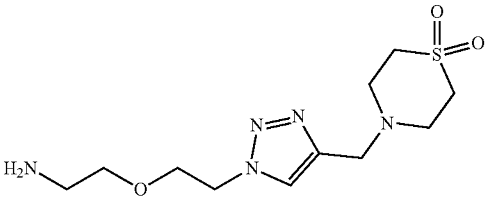 [SMILES: NCCOCCn1cc(CN2CCS(=O)(=O)CC2)nn1] |
| 215 | 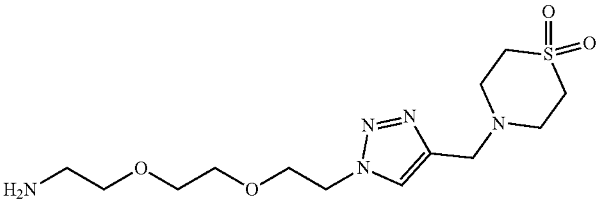 [SMILES: NCCOCCOCCn1cc(CN2CCS(=O)(=O)CC2)nn1] |
| 216 | 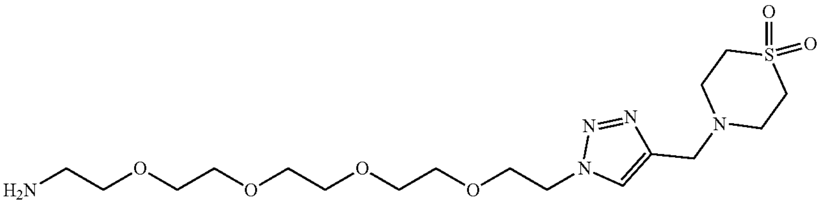 [SMILES: NCCOCCOCCOCCOCCn1cc(CN2CCS(=O)(=O)CC2)nn1] |
| 217 | 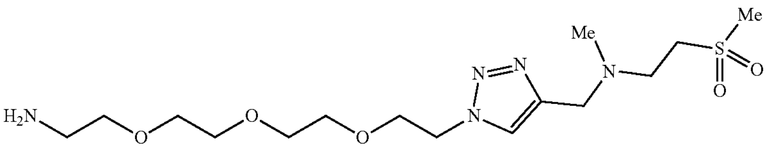 [SMILES: CN(CCS(C)(=O)=O)Cc1cn(CCOCCOCCOCCN)nn1] |
| 218 | 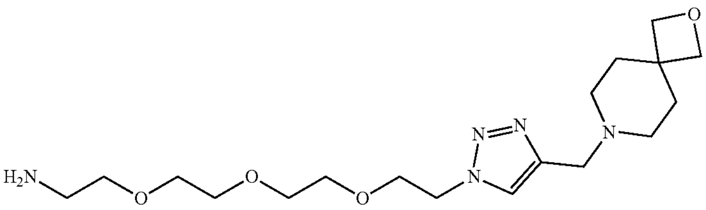 [SMILES: NCCOCCOCCOCCn1cc(CN2CCC3(CC2)COC3)nn1] |

TABLE 1-continued
| Exemplary compounds of Formula (I) | |
|---|---|
| Compound No. | Structure |
| 219 | 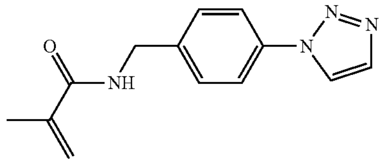 [SMILES: C=C(C)C(=O)NCc1ccc(-n2ccnn2)cc1] |
| 220 | 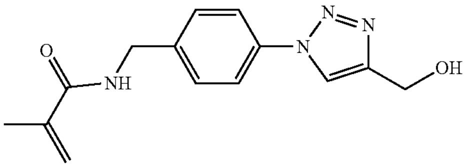 [SMILES: C=C(C)C(=O)NCc1ccc(-n2cc(CO)nn2)cc1] |
| 221 | 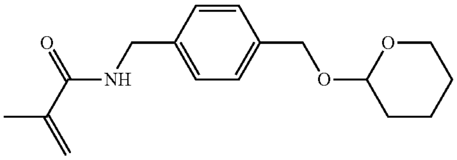 [SMILES: C=C(C)C(=O)NCc1ccc(COC2CCCCO2)cc1] |
| 222 | 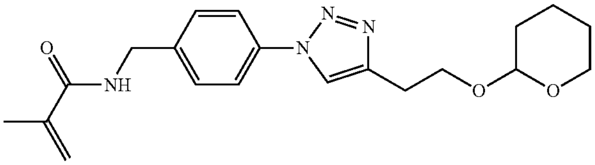 [SMILES: C=C(C)C(=O)NCc1ccc(-n2cc(CCOC3CCCCO3)nn2)cc1] |
| 223 | 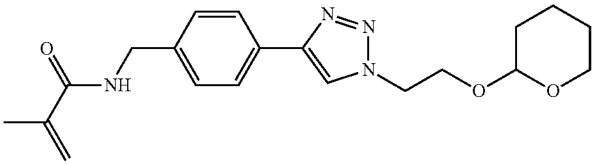 [SMILES: C=C(C)C(=O)NCc1ccc(-c2cn(CCOC3CCCCO3)nn2)cc1] |
| 224 | 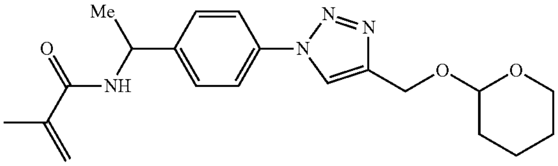 [SMILES: C=C(C)C(=O)NC(C)c1ccc(-n2cc(COC3CCCCO3)nn2)cc1] |
| 225 | 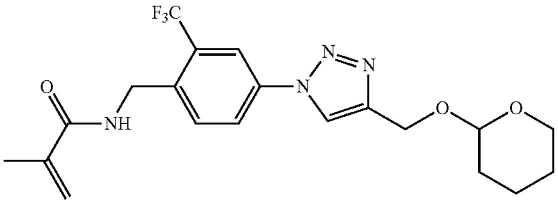 [SMILES: C=C(C)C(=O)NCc1ccc(-n2cc(COC3CCCCO3)nn2)cc1C(F)(F)F] |
| 226 | 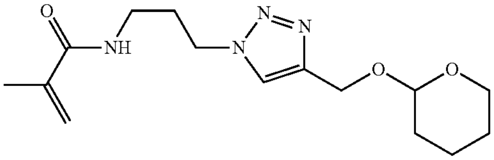 [SMILES: C=C(C)C(=O)NCCCn1cc(COC2CCCCO2)nn1] |

TABLE 1-continued
| Compound No. | Structure |
| --- | --- |
| | Exemplary compounds of Formula (I) |
| 227 | 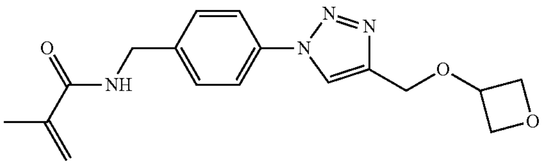 [SMILES: C=C(C)C(=O)NCc1ccc(-n2cc(COC3COC3)nn2)cc1] |
| 228 | 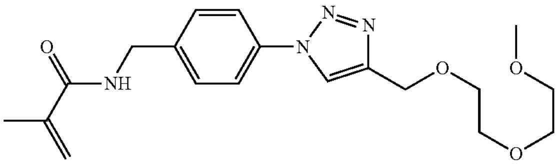 [SMILES: C=C(C)C(=O)NCc1ccc(-n2cc(COCCOCCOC)nn2)cc1] |
| 229 | 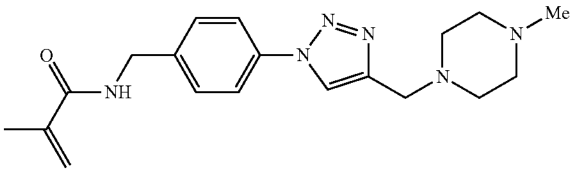 [SMILES: C=C(C)C(=O)NCc1ccc(-n2cc(CN3CCN(C)CC3)nn2)cc1] |
| 230 | 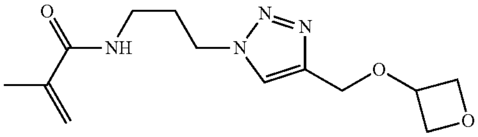 [SMILES: C=C(C)C(=O)NCCCn1cc(COC2COC2)nn1] |
| 231 | 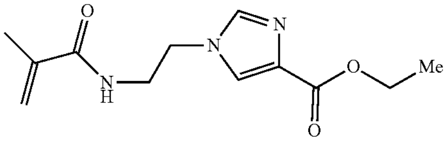 [SMILES: C=C(C)C(=O)NCCn1cnc(C(=O)OCC)c1] |
| 232 | 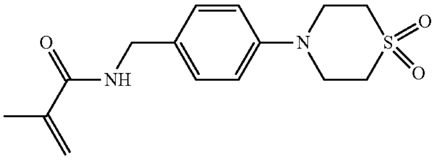 [SMILES: C=C(C)C(=O)NCc1ccc(N2CCS(=O)(=O)CC2)cc1] |
| 233 | 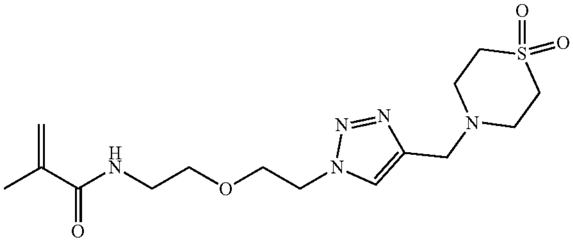 [SMILES: C=C(C)C(=O)NCCOCCn1cc(CN2CCS(=O)(=O)CC2)nn1] |
| 234 | 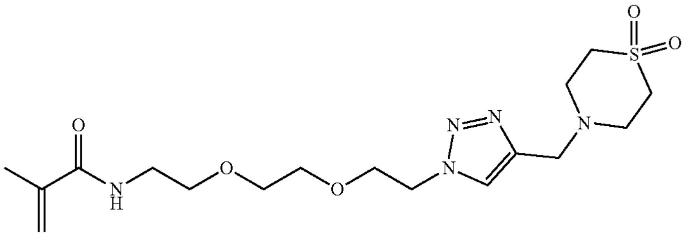 [SMILES: C=C(C)C(=O)NCCOCCOCCn1cc(CN2CCS(=O)(=O)CC2)nn1] |

TABLE 1-continued

| Exemplary compounds of Formula (I) | |
|---|---|
| Compound No. | Structure |
| 235 | 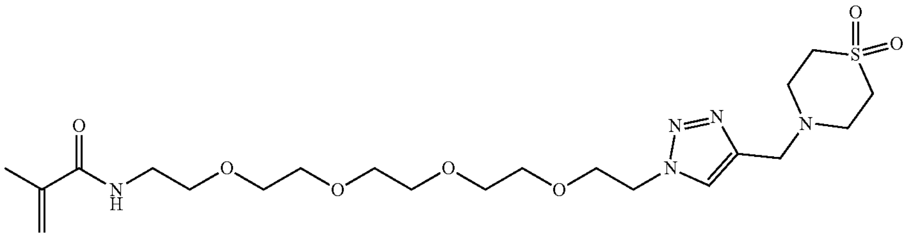 [SMILES: C=C(C)C(=O)NCCOCCOCCOCCOCCn1cc(CN2CCS(=O)(=O)CC2)nn1] |
| 236 | 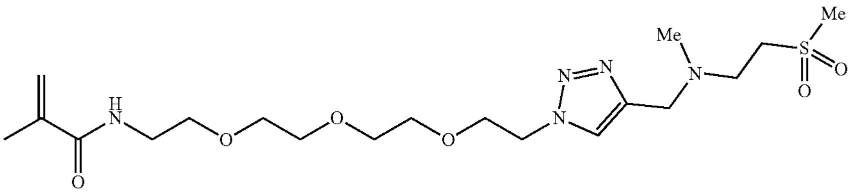 [SMILES: C=C(C)C(=O)NCCOCCOCCOCCn1cc(CN(C)CCS(C)(=O)=O)nn1] |
| 237 | 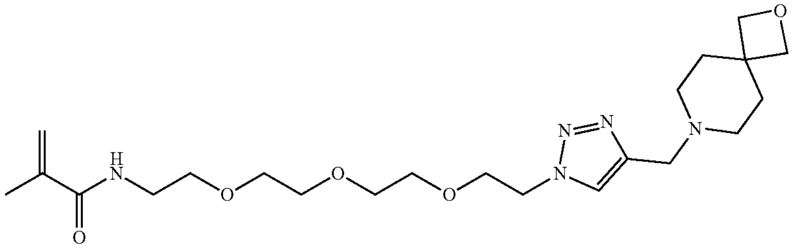 [SMILES: C=C(C)C(=O)NCCOCCOCCOCCn1cc(CN2CCC3(CC2)COC3)nn1] |

Polymers

The disclosure features a polymer modified with a compound of Formula (II):

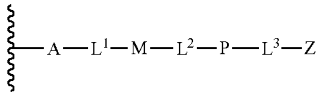

(II)

or a pharmaceutically acceptable salt thereof, wherein:

A is alkyl, alkenyl, alkynyl, heteroalkyl, cycloalkyl, heterocyclyl, aryl, heteroaryl, —O—, —C(O))—, —C(O)—, —OC(O)—, —N($R^C$)—, —N($R^C$)C(O)—, —C(O)N($R^C$)—, —N($R^C$)C(O)($C_1$-$C_6$-alkylene)-, —N($R^C$)C(O)($C_1$-$C_6$-alkenylene)-, —N($R^C$)N($R^D$)—, —NCN—, —C(=N($R^C$)($R^D$))O—, —S—, —$S(O)_x$—, —$OS(O)_x$—, —N($R^C$)$S(O)_x$—, —$S(O)_x$N($R^C$)—, —P($R^F$)$_y$—, —Si($OR^A$)$_2$—, —Si($R^G$)($OR^A$)—, —B($OR^A$)—, or a metal, each of which is optionally linked to an attachment group (e.g., an attachment group described herein) and is optionally substituted by one or more $R^1$;

each of $L^1$ and $L^3$ is independently a bond, alkyl, or heteroalkyl, wherein each alkyl and heteroalkyl is optionally substituted by one or more $R^2$;

$L^2$ is a bond;

M is absent, alkyl, heteroalkyl, cycloalkyl, heterocyclyl, aryl, or heteroaryl, each of which is optionally substituted by one or more $R^3$;

P is absent, cycloalkyl, heterocycyl, or heteroaryl, each of which is optionally substituted by one or more $R^4$;

Z is hydrogen, alkyl, alkenyl, alkynyl, heteroalkyl, —$OR^A$, —C(O)$R^A$, —C(O)$OR^A$, —C(O)N($R^C$)($R^D$), —N($R^C$)C(O)$R^A$, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$;

or $R^C$ and $R^D$, taken together with the nitrogen atom to which they are attached, form a ring (e.g., a 5-7 membered ring), optionally substituted with one or more $R^6$;

each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —C(O)$OR^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), $SR^{E1}$, $S(O)_xR^{E1}$, —$OS(O)_xR^{E1}$, —N($R^{C1}$)$S(O)_xR^{E1}$, —$S(O)_x$N($R^{C1}$)($R^{D1}$), -P($R^{F1}$)$_y$ cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

In some embodiments, the compound of Formula (II) is a compound of Formula (II-a):

(II-a)

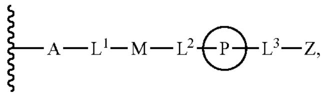

or a pharmaceutically acceptable salt thereof, wherein:

A is alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)N($R^D$)—, —NCN—, —C(=N($R^C$)($R^D$))O—, —S—, —S$(O)_x$—, —OS$(O)_x$—, —N($R^C$)S$(O)_x$—, —S$(O)_x$N($R^C$)—, —P$(R^F)_y$—, —Si$(OR^A)_2$—Si($R^G$)($OR^A$)—, —B($OR^A$)—, or a metal, each of which is optionally linked to an attachment group (e.g., an attachment group described herein) and optionally substituted by one or more $R^1$;

each of $L^1$ and $L^3$ is independently a bond, alkyl, or heteroalkyl, wherein each alkyl and heteroalkyl is optionally substituted by one or more $R^2$;

$L^2$ is a bond;

M is absent, alkyl, heteroalkyl, cycloalkyl, heterocyclyl, aryl, or heteroaryl, each of which is optionally substituted by one or more $R^3$;

P is heteroaryl optionally substituted by one or more $R^4$;

Z is alkyl, alkenyl, alkynyl, heteroalkyl, cycloalkyl, heterocyclyl, aryl, or heteroaryl, each of which is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$;

or $R^C$ and $R^D$, taken together with the nitrogen atom to which they are attached, form a ring (e.g., a 5-7 membered ring), optionally substituted with one or more $R^6$;

each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —C(O)$OR^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), $SR^{E1}$, $S(O)_xR^{E1}$, —OS$(O)_xR^{E1}$, —N($R^{C1}$)S$(O)_xR^{E1}$, —S$(O)_x$N($R^{C1}$)($R^{D1}$), —P$(R^{F1})_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

In some embodiments, for Formulas (II) and (II-a), A is alkyl, alkenyl, alkynyl, heteroalkyl, cycloalkyl, heterocyclyl, aryl, heteroaryl, —O—, —C(O))—, —C(O)—, —OC(O)—, —N($R^C$)C(O)—, —N($R^C$)C(O)($C_1$-$C_6$-alkylene)-, —N($R^C$)C(O)($C_1$-$C_6$-alkenylene)-, or —N($R^C$)—. In some embodiments, A is alkyl, alkenyl, alkynyl, heteroalkyl, cycloalkyl, heterocyclyl, aryl, heteroaryl, —O—, —C(O))—, —C(O)—, —OC(O)—, or —N($R^C$)—. In some embodiments, A is alkyl, alkenyl, alkynyl, heteroalkyl, —O—, —C(O))—, —C(O)—, —OC(O)—, or —N($R^C$)—. In some embodiments, A is alkyl, —O—, —C(O))—, —C(O)—, —OC(O), or —N($R^C$)—. In some embodiments, A is —N($R^C$)C(O)—, —N($R^C$)C(O)($C_1$-$C_6$-alkylene)-, or —N($R^C$)C(O)($C_1$-$C_6$-alkenylene)-. In some embodiments, A is —N($R^C$)—. In some embodiments, A is —N($R^C$)—, and $R^C$ an $R^D$ is independently hydrogen or alkyl. In some embodiments, A is —NH—. In some embodiments, A is —N($R^C$)C(O)($C_1$-$C_6$-alkylene)-, wherein alkylene is substituted with $R^1$. In some embodiments, A is —N($R^C$)C(O)($C_1$-$C_6$-alkylene)-, and $R^1$ is alkyl (e.g., methyl). In some embodiments, A is —NHC(O)C$(CH_3)_2$—. In some embodiments, A is —N($R^C$)C(O)(methylene)-, and $R^4$ is alkyl (e.g., methyl). In some embodiments, A is —NHC(O)CH($CH_3$)—. In some embodiments, A is —NHC(O)C($CH_3$)—.

In some embodiments, for Formulas (II) and (II-a), $L^1$ is a bond, alkyl, or heteroalkyl. In some embodiments, $L^1$ is a bond or alkyl. In some embodiments, $L^1$ is a bond. In some embodiments, $L^1$ is alkyl. In some embodiments, $L^1$ is $C_1$-$C_6$ alkyl. In some embodiments, $L^1$ is —$CH_2$—, —CH($CH_3$)—, —$CH_2CH_2CH_2$, or —$CH_2CH_2$—. In some embodiments, $L^1$ is —$CH_2$— or —$CH_2CH_2$-.

In some embodiments, for Formulas (II) and (II-a), $L^3$ is a bond, alkyl, or heteroalkyl. In some embodiments, $L^3$ is a bond. In some embodiments, $L^3$ is alkyl. In some embodiments, $L^3$ is $C_1$-$C_{12}$ alkyl. In some embodiments, $L^3$ is $C_1$-$C_6$ alkyl. In some embodiments, $L^3$ is —$CH_2$—. In some embodiments, $L^3$ is heteroalkyl. In some embodiments, $L^3$ is $C_1$-$C_{12}$ heteroalkyl, optionally substituted with one or more $R^2$ (e.g., oxo). In some embodiments, $L^3$ is $C_1$-$C_6$ heteroalkyl, optionally substituted with one or more $R^2$ (e.g., oxo). In some embodiments, $L^3$ is —C(O)$OCH_2$—, —$CH_2(OCH_2CH_2)_2$—, —$CH_2(OCH_2CH_2)_3$—, $CH_2CH_2O$—, or —$CH_2O$—. In some embodiments, $L^3$ is —$CH_2O$—.

In some embodiments, for Formulas (II) and (II-a), M is absent, alkyl, heteroalkyl, aryl, or heteroaryl. In some embodiments, M is heteroalkyl, aryl, or heteroaryl. In some embodiments, M is absent. In some embodiments, M is alkyl (e.g., $C_1$-$C_6$ alkyl). In some embodiments, M is —$CH_2$—. In some embodiments, M is heteroalkyl (e.g., $C_1$-$C_6$ heteroalkyl). In some embodiments, M is (—$OCH_2CH_2$—)z, wherein z is an integer selected from 1 to 10. In some embodiments, z is an integer selected from 1 to 5. In some embodiments, M is —$OCH_2CH_2$—, $(—OCH_2CH_2—)_2$, $(—OCH_2CH_2—)_3$, $(—OCH_2CH_2—)_4$, or $(—OCH_2CH_2—)_5$. In some embodiments, M is —$OCH_2CH_2$—, $(—OCH_2CH_2—)_2$, $(—OCH_2CH_2—)_3$, or $(—OCH_2CH_2—)_4$. In some embodiments, M is $(—OCH_2CH_2—)_3$. In some embodiments, M is aryl. In some embodiments, M is phenyl. In some embodiments, M is unsubstituted phenyl. In some embodiments, M is

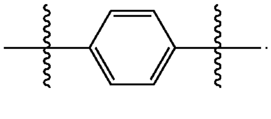.

In some embodiments, M is phenyl substituted with $R^7$ (e.g., 1 $R^7$). In some embodiments, M is

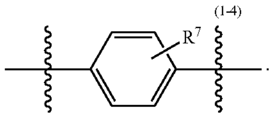

In some embodiments, $R^7$ is $CF_3$.

In some embodiments, for Formulas (II) and (II-a), P is absent, heterocyclyl, or heteroaryl. In some embodiments, P is absent. In some embodiments, for Formulas (I) and (I-a), P is a tricyclic, bicyclic, or monocyclic heteroaryl. In some embodiments, P is a monocyclic heteroaryl. In some embodiments, P is a nitrogen-containing heteroaryl. In some embodiments, P is a monocyclic, nitrogen-containing heteroaryl. In some embodiments, P is a 5-membered heteroaryl. In some embodiments, P is a 5-membered nitrogen-containing heteroaryl. In some embodiments, P is tetrazolyl, imidazolyl, pyrazolyl, or triazolyl, pyrrolyl, oxazolyl, or thiazolyl. In some embodiments, P is tetrazolyl, imidazolyl, pyrazolyl, or triazolyl, or pyrrolyl. In some embodiments, P is imidazolyl. In some embodiments, P is

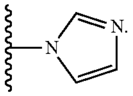 [SMILES: *n1ccnc1]

In some embodiments, P is triazolyl. In some embodiments, P is 1,2,3-triazolyl. In some embodiments, P is

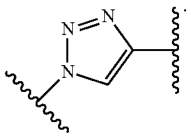 [SMILES: *c1cn(*)nn1]

In some embodiments, P is heterocyclyl. In some embodiments, P is a 5-membered heterocyclyl or a 6-membered heterocyclyl. In some embodiments, P is imidazolidinonyl. In some embodiments, P is

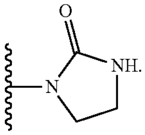 [SMILES: *N1CCNC1=O]

In some embodiments, P is thiomorpholinyl-1,1-dioxidyl. In some embodiments, P is

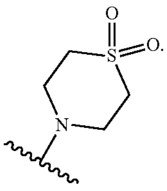 [SMILES: *N1CCS(=O)(=O)CC1]

In some embodiments, for Formulas (I) and (I-a), Z is alkyl, heteroalkyl, cycloalkyl, heterocyclyl, aryl, or heteroaryl. In some embodiments, Z is heterocyclyl. In some embodiments, Z is monocyclic or bicyclic heterocyclyl. In some embodiments, Z is an oxygen-containing heterocyclyl. In some embodiments, Z is a 4-membered heterocyclyl, 5-membered heterocyclyl, or 6-membered heterocyclyl. In some embodiments, Z is a 6-membered heterocyclyl. In some embodiments, Z is a 6-membered oxygen-containing heterocyclyl. In some embodiments, Z is tetrahydropyranyl. In some embodiments, Z is

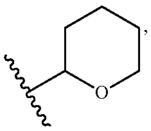, 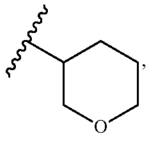, or 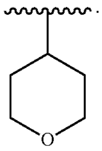.

In some embodiments, Z is a 4-membered oxygen-containing heterocyclyl. In some embodiments, Z is

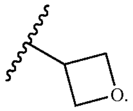 [SMILES: *C1COC1]

In some embodiments, Z is a bicyclic oxygen-containing heterocyclyl. In some embodiments, Z is phthalic anhydridyl. In some embodiments, Z is a sulfur-containing heterocyclyl. In some embodiments, Z is a 6-membered sulfur-containing heterocyclyl. In some embodiments, Z is a 6-membered heterocyclyl containing a nitrogen atom and a sulfur atom. In some embodiments, Z is thiomorpholinyl-1,1-dioxidyl. In some embodiments, Z is

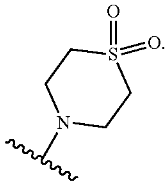 [SMILES: *N1CCS(=O)(=O)CC1]

In some embodiments, Z is a nitrogen-containing heterocyclyl. In some embodiments, Z is a 6-membered nitrogen-containing heterocyclyl. In some embodiments, Z is

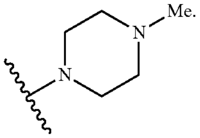 [SMILES: *N1CCN(C)CC1]

In some embodiments, Z is a bicyclic heterocyclyl. In some embodiments, Z is a bicyclic nitrogen-containing heterocyclyl, optionally substituted with one or more $R^5$. In some embodiments, Z is 2-oxa-7-azaspiro[3.5]nonanyl. In some embodiments, Z is

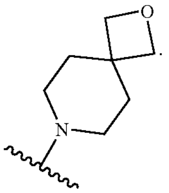 [SMILES: *N1CCC2(CC1)COC2]

In some embodiments, Z is 1-oxa-3,8-diazaspiro[4.5]decan-2-one. In some embodiments, Z is

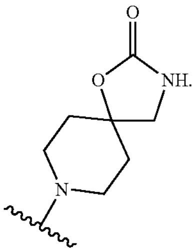 [SMILES: *N1CCC2(CC1)CNC(=O)O2]

In some embodiments, for Formulas (II) and (II-a), Z is aryl. In some embodiments, Z is monocyclic aryl. In some embodiments, Z is phenyl. In some embodiments, Z is monosubstituted phenyl (e.g., with 1 $R^5$). In some embodiments, Z is monosubstituted phenyl, wherein the 1 $R^5$ is a nitrogen-containing group. In some embodiments, Z is monosubstituted phenyl, wherein the 1 $R^5$ is $NH_2$. In some embodiments, Z is monosubstituted phenyl, wherein the 1 $R^5$ is an oxygen-containing group. In some embodiments, Z is monosubstituted phenyl, wherein the 1 $R^5$ is an oxygen-containing heteroalkyl. In some embodiments, Z is monosubstituted phenyl, wherein the 1 $R^5$ is $OCH_3$. In some embodiments, Z is monosubstituted phenyl, wherein the 1 $R^5$ is in the ortho position. In some embodiments, Z is monosubstituted phenyl, wherein the 1 $R^5$ is in the meta position. In some embodiments, Z is monosubstituted phenyl, wherein the 1 $R^5$ is in the para position.

In some embodiments, for Formulas (II) and (II-a), Z is alkyl. In some embodiments, Z is $C_1$-$C_{12}$ alkyl. In some embodiments, Z is $C_1$-$C_{10}$ alkyl. In some embodiments, Z is $C_1$-$C_8$ alkyl. In some embodiments, Z is $C_1$-$C_8$ alkyl substituted with 1-5 $R^5$. In some embodiments, Z is $C_1$-$C_8$ alkyl substituted with 1 $R^5$. In some embodiments, Z is $C_1$-$C_8$ alkyl substituted with 1 $R^5$, wherein $R^5$ is alkyl, heteroalkyl, halogen, oxo, —$OR^{A1}$, —$C(O)OR^{A1}$, —$C(O)R^{B1}$, —$OC(O)R^{B1}$, or —$N(R^{C1}(R^{D1})$. In some embodiments, Z is $C_1$-$C_8$ alkyl substituted with 1 $R^5$, wherein $R^5$ is -$OR^{A1}$ or —$C(O)OR^{A1}$. In some embodiments, Z is $C_1$-$C_8$ alkyl substituted with 1 $R^5$, wherein $R^5$ is —$OR^{A1}$ or —C(O)OH. In some embodiments, Z is —$CH_3$.

In some embodiments, for Formulas (II) and (II-a), Z is heteroalkyl. In some embodiments, Z is $C_1$-$C_{12}$ heteroalkyl. In some embodiments, Z is $C_1$-$C_{10}$ heteroalkyl. In some embodiments, Z is $C_1$-$C_8$ heteroalkyl. In some embodiments, Z is $C_1$-$C_6$ heteroalkyl. In some embodiments, Z is a nitrogen-containing heteroalkyl optionally substituted with one or more $R^5$. In some embodiments, Z is a nitrogen and sulfur-containing heteroalkyl substituted with 1-5 $R^5$. In some embodiments, Z is N-methyl-2-(methylsulfonyl)ethan-1-aminyl.

In some embodiments, Z is —$OR^A$ or —$C(O)OR^A$. In some embodiments, Z is —$OR^A$ (e.g., —OH or —$OCH_3$). In some embodiments, Z is —$OCH_3$. In some embodiments, Z is —$C(O)OR^A$ (e.g., —C(O)OH).

In some embodiments, Z is hydrogen.

In some embodiments, $L^2$ is a bond and P and $L^3$ are independently absent. In some embodiments, $L^2$ is a bond, P is heteroaryl, $L^3$ is a bond, and Z is hydrogen. In some embodiments, P is heteroaryl, $L^3$ is heteroalkyl, and Z is alkyl.

In some embodiments, the compound of Formula (II-a) is a compound of Formula (II-b):

(II-b)

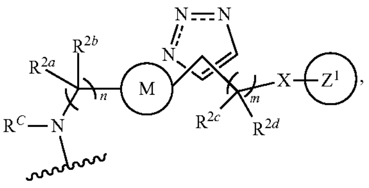

or a pharmaceutically acceptable salt thereof, wherein Ring $M^1$ is cycloalkyl, heterocyclyl, aryl, or heteroaryl, each of which is optionally substituted with 1-5 $R^3$; Ring $Z^1$ is cycloalkyl, heterocyclyl, aryl or heteroaryl, optionally substituted with 1-5 $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl, or each of $R^{2a}$ and $R^{2b}$ or $R^{2c}$ and $R^{2d}$ is taken together to form an oxo group; X is absent, $N(R^{10})(R^{11})$, O, or S; $R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; each $R^3$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, cycloalkyl, heterocyclyl, aryl, or heteroaryl; each of $R^{10}$ and $R^{11}$ is independently hydrogen, alkyl, alkenyl, alkynyl, heteroalkyl, —$C(O)OR^{A1}$, —$C(O)R^{B1}$, —$OC(O)R^{B1}$, —$C(O)N(R^{C1})$, cycloalkyl, heterocyclyl, aryl, or heteroaryl; each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, cyano, oxo, hydroxyl, cycloalkyl, or heterocyclyl; each m and n is independently 1, 2, 3, 4, 5, or 6; and "〰" refers to a connection to an attachment group or a polymer described herein. In some embodiments, for each $R^3$ and $R^5$, each alkyl, alkenyl, alkynyl, heteroalkyl, cycloalkyl, heterocyclyl, aryl, or heteroaryl is optionally and independently substituted with halogen, oxo, cyano, cycloalkyl, or heterocyclyl.

In some embodiments, the compound of Formula (II-b) is a compound of Formula (II-b-i):

(II-b-i)

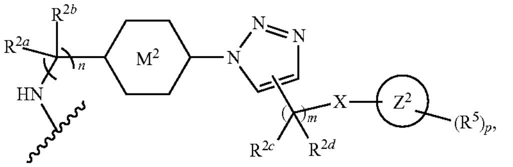

or a pharmaceutically acceptable salt thereof, wherein Ring $M^2$ is aryl or heteroaryl optionally substituted with one or more $R^3$; Ring $Z^2$ is cycloalkyl, heterocyclyl, aryl, or heteroaryl; each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group; X is absent, O, or S; each $R^3$ and $R^5$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with halogen, or two $R^5$ are taken together to form a 5-6 membered ring fused to Ring $Z^2$; each $R^{A1}$ and $R^{B1}$ is independently hydrogen, alkyl, or heteroalkyl; m and n are each independently 1, 2, 3, 4, 5, or 6; p is 0, 1, 2, 3, 4, 5, or 6; and "~~~" refers to a connection to an attachment group or a polymer described herein.

In some embodiments, the compound of Formula (II-b-i) is a compound of Formula (II-b-ii):

(II-b-ii)

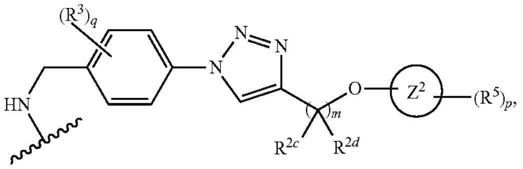

or a pharmaceutically acceptable salt thereof, wherein Ring $Z^2$ is cycloalkyl, heterocyclyl, aryl or heteroaryl; each of $R^{2c}$ and $R^{2d}$ is independently hydrogen, alkyl, or heteroalkyl, or $R^{2c}$ and $R^{2d}$ and taken together to form an oxo group; each $R^3$ and $R^5$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with halogen; each $R^{A1}$ and $R^{B1}$ is independently hydrogen, alkyl, or heteroalkyl; and each of p and q is independently 0, 1, 2, 3, 4, 5, or 6; and "~~~" refers to a connection to an attachment group or a polymer described herein.

In some embodiments, the compound of Formula (II-b-ii) is a compound of Formula (II-b-iii):

(II-b-iii)

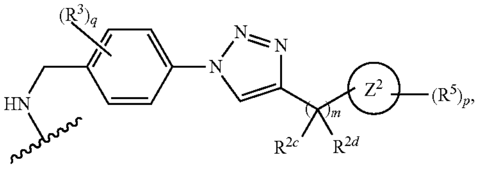

or a pharmaceutically acceptable salt thereof, wherein Ring $Z^2$ is cycloalkyl, heterocyclyl, aryl or heteroaryl; each of $R^{2c}$ and $R^{2d}$ is independently hydrogen, alkyl, or heteroalkyl, or $R^{2c}$ and $R^{2d}$ are taken together to form an oxo group; each $R^3$ and $R^5$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with halogen; each $R^{A1}$ and $R^{B1}$ is independently hydrogen, alkyl, or heteroalkyl; m is 1, 2, 3, 4, 5, or 6; and each of p and q is independently 0, 1, 2, 3, 4, 5, or 6; and "~~~" refers to a connection to an attachment group or a polymer described herein.

In some embodiments, the compound of Formula (II-a) is a compound of Formula (II-c):

(II-c)

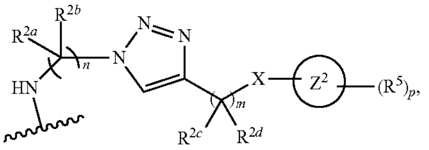

or a pharmaceutically acceptable salt thereof, wherein Ring $Z^2$ is cycloalkyl, heterocyclyl, aryl or heteroaryl; X is absent, O, or S; each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group; each $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; each of m and n is independently 1, 2, 3, 4, 5, or 6; p is 0, 1, 2, 3, 4, 5, or 6; and "~~~" refers to a connection to an attachment group or a polymer described herein.

In some embodiments, the compound of Formula (II-a) is a compound of Formula (II-d):

(II-d)

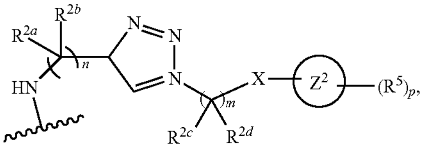

or a pharmaceutically acceptable salt thereof, wherein Ring $Z^2$ is cycloalkyl, heterocyclyl, aryl or heteroaryl; X is absent, O, or S; each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group; each $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; each of m and n is independently 1, 2, 3, 4, 5, or 6; p is 0, 1, 2, 3, 4, 5, or 6; and "~~~" refers to a connection to an attachment group or a polymer described herein.

In some embodiments, the compound of Formula (II) is a compound of Formula (II-e):

(II-e)

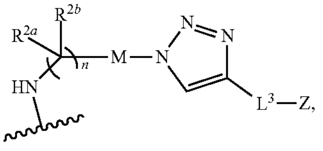

or a pharmaceutically acceptable salt thereof, wherein M is a bond, alkyl or aryl, each of which is optionally substituted with one or more $R^3$; $L^3$ is alkyl or heteroalkyl optionally substituted with one or more $R^2$; Z is hydrogen, alkyl, heteroalkyl, cycloalkyl, heterocyclyl, aryl, heteroaryl, or —$OR^A$, wherein alkyl and heteralkyl are optionally substituted with one or more $R^5$; $R^A$ is hydrogen; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; and n is independently 1, 2, 3, 4, 5, or 6; and "~~~" refers to a connection to an attachment group or a polymer described herein.

In some embodiments, the compound of Formula (II-e) is a compound of Formula (II-e-i):

(II-e-i)

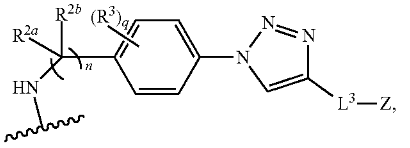

or a pharmaceutically acceptable salt thereof, wherein $L^3$ is alkyl or heteroalkyl, each of which is optionally substituted with one or more $R^2$; Z is hydrogen, alkyl, heteroalkyl, or —$OR^A$, wherein alkyl and heteroalkyl are optionally substituted with one or more $R^5$; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; n is independently 1, 2, 3, 4, 5, or 6; and "~~~" refers to a connection to an attachment group or a polymer described herein.

In some embodiments, the compound of Formula (II) is a compound of Formula (II-f):

(II-f)

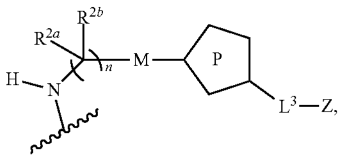

or a pharmaceutically acceptable salt thereof, wherein M is alkyl optionally substituted with one or more $R^3$; Ring P is heteroaryl optionally substituted with one or more $R^4$; $L^3$ is alkyl or heteroalkyl optionally substituted with one or more $R^2$; Z is alkyl, heteroalkyl, cycloalkyl, heterocyclyl, aryl, or heteroaryl, each of which is optionally substituted with one or more $R^5$; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, $R^4$, and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; n is independently 1, 2, 3, 4, 5, or 6; and "~~~" refers to a connection to an attachment group or a polymer described herein.

In some embodiments, the compound of Formula (II) is a compound of Formula (II-g):

(II-g)

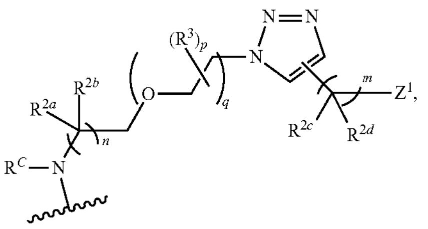

or a pharmaceutically acceptable salt thereof, wherein $Z^1$ is alkyl, alkenyl, alkynyl, heteroalkyl, cycloalkyl, heterocyclyl, aryl, or heteroaryl, each of which is optionally substituted with 1-5 $R^5$; $R^C$ is hydrogen, alkyl, alkenyl, alkynyl, or heteroalkyl, wherein each of alkyl, alkenyl, alkynyl, or heteroalkyl is optionally substituted with 1-6 $R^6$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; each of $R^3$, $R^5$, and $R^6$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; q is an integer from 0 to 25; and "~~~" refers to a connection to an attachment group or a polymer described herein.

In some embodiments, the compound of Formula (II-g) is a compound of Formula (II-g-i):

(II-g-i)

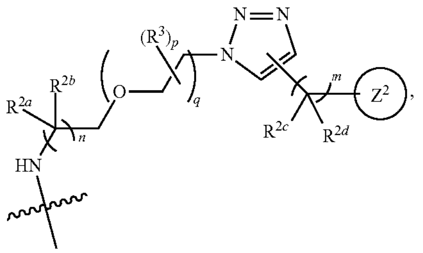

or a pharmaceutically acceptable salt thereof, wherein Ring $Z^2$ is cycloalkyl, heterocyclyl, aryl, or heteroaryl, each of which is optionally substituted with 1-5 $R^5$; each of $R^{2a}$, $R^{2b}$, $R^{2c}$, and $R^{2d}$ is independently hydrogen, alkyl, heteroalkyl, halo; or $R^{2a}$ and $R^{2b}$ or $R^{2c}$ and $R^{2d}$ are taken together to form an oxo group; each of $R^3$ and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; and o and p are each independently 0, 1, 2, 3, 4, or 5; q is an integer from 0 to 25; and "~~~" refers to a connection to an attachment group or a polymer described herein.

In some embodiments, the compound of Formula (I-g-i) is a compound of Formula (I-g-ii):

(I-g-ii)

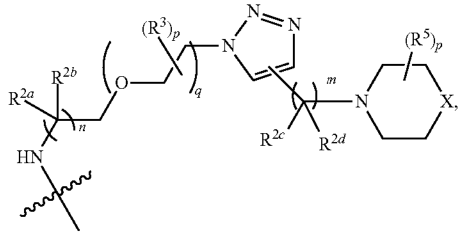

or a pharmaceutically acceptable salt thereof, wherein X is C(R')(R"), N(R'), or $S(O)_x$; each of R' and R" is independently hydrogen, alkyl, halogen, or cycloalkyl; each of $R^{2a}$, $R^{2b}$, $R^{2c}$, and $R^{2d}$ is independently hydrogen, alkyl, heteroalkyl, or halo; or $R^{2a}$ and $R^{2b}$ or $R^{2c}$ and $R^{2d}$ are taken together to form an oxo group; each of $R^3$ and $R^6$ is independently alkyl, heteroalkyl, halogen, oxo, $-OR^{A1}$, —C(O)$OR^{A1}$, or —C(O)$R^{B1}$; each $R^{A1}$ and $R^{B1}$ is independently hydrogen, alkyl, or heteroalkyl; m and n are each independently 1, 2, 3, 4, 5, or 6; p is 0, 1, 2, 3, 4, or 5; and q is an integer from 0 to 25; x is 0, 1, or 2.

In some embodiments, the compound is a compound of Formula (II). In some embodiments of Formula (I), $L^2$ is a bond and P and $L^3$ are independently absent.

In some embodiments of Formula (II), P is absent, $L^1$ is —$NHCH_2$, $L^2$ is a bond, M is aryl (e.g., phenyl), $L^3$ is —$CH_2O$, and Z is heterocyclyl (e.g., a nitrogen-containing heterocyclyl, e.g., thiomorpholinyl-1,1-dioxide). In some embodiments, the compound of Formula (II) is Compound 113.

In some embodiments of Formula (II), P is absent, $L^1$ is —$NHCH_2$, $L^2$ is a bond, M is absent, $L^3$ is a bond, and Z is heterocyclyl (e.g., an oxygen-containing heterocyclyl, e.g., tetrahydropyranyl, tetrahydrofuranyl, oxetanyl, or oxiranyl). In some embodiments, the compound of Formula (II) is Compound 102.

In some embodiments, the compound is a compound of Formula (II-a). In some embodiments of Formula (II-a), $L^2$ is a bond, P is heteroaryl, $L^3$ is a bond, and Z is hydrogen. In some embodiments, P is heteroaryl, $L^3$ is heteroalkyl, and Z is alkyl. In some embodiments, $L^2$ is a bond and P and $L^3$ are independently absent. In some embodiments, $L^2$ is a bond, P is heteroaryl, $L^3$ is a bond, and Z is hydrogen. In some embodiments, P is heteroaryl, $L^3$ is heteroalkyl, and Z is alkyl.

In some embodiments, the compound is a compound of Formula (II-b-i). In some embodiments of Formula (II-b-i), each of $R^{2a}$ and $R^{2b}$ is independently hydrogen or $CH_3$, each of $R^{2c}$ and $R^{2d}$ is independently hydrogen, m is 1 or 2, n is 1, X is O, p is 0, $M^2$ is phenyl optionally substituted with one or more $R^3$, $R^3$ is —$CF_3$, and $Z^2$ is heterocyclyl (e.g., an oxygen-containing heterocyclyl, e.g., tetrahydropyranyl, tetrahydrofuranyl, oxetanyl, or oxiranyl). In some embodiments, the compound of Formula (II-b-i) is Compound 103, Compound 104, Compound 105, Compound 106, or Compound 108.

In some embodiments, the compound is a compound of Formula (II-b-iii). In some embodiments of Formula (II-b-iii), each of $R^{2c}$ and $R^{2d}$ is independently hydrogen, m is 1, p is 1, q is 0, $R^5$ is —$CH_3$, and Z is heterocyclyl (e.g., a nitrogen-containing heterocyclyl, e.g., piperazinyl). In some embodiments, the compound of Formula (II-b-iii) is Compound 110.

In some embodiments, the compound is a compound of Formula (II-c). In some embodiments of Formula (II-c), each of $R^{2a}$, $R^{2b}$, $R^{2c}$, and $R^{2d}$ is independently hydrogen, m is 1, n is 3, X is 0, p is 0, and Z is heterocyclyl (e.g., an oxygen-containing heterocyclyl, e.g., tetrahydropyranyl, tetrahydrofuranyl, oxetanyl, or oxiranyl). In some embodiments, the compound of Formula (II-c) is Compound 107 or Compound 111.

In some embodiments, the compound is a compound of Formula (II-e). In some embodiments of Formula (II-e), each of $R^{2a}$ and $R^{2b}$ is independently hydrogen, n is 1, q is 0, $L_3$ is —$CH_2(OCH_2CH_2)_2$—, and Z is —$OCH_3$.

In some embodiments, the compound is a compound of Formula (II-e-i). In some embodiments of Formula (II-e-i), each of $R^{2a}$ and $R^{2b}$ is independently hydrogen, n is 1, q is 0, $L^3$ is —$CH_2(OCH_2CH_2)_2$, and Z is —$OCH_3$. In some embodiments, the compound of Formula (II-e-i) is Compound 109.

In some embodiments of Formula (II-e-i), each of $R^{2a}$ and $R^{2b}$ is independently hydrogen, n is 1, $L^3$ is a bond or —$CH_2$, and Z is hydrogen or —OH. In some embodiments, the compound of Formula (II-e-i) is Compound 100.

In some embodiments, the compound is a compound of Formula (II-g). In some embodiments of Formula (II-g), each of $R^{2a}$, $R^{2b}$, $R^{2c}$, and $R^{2d}$ is independently hydrogen, m is 1, n is 2, q is 3, p is 0, $R^C$ is hydrogen, and $Z^1$ is heteroalkyl optionally substituted with $R^5$ (e.g., —$N(CH_3)(CH_2CH_2)S(O)_2CH_3$). In some embodiments, the compound of Formula (II-g) is Compound 117.

In some embodiments, the compound is a compound of Formula (II-g-i). In some embodiments of Formula (II-g-i), each of $R^{2a}$, $R^{2b}$, $R^{2c}$, and $R^{2d}$ is independently hydrogen, m is 1, n is 2, q is 3, p is 0, $R^C$ is hydrogen, and $Z^2$ is heterocyclyl (e.g., an nitrogen-containing heterocyclyl, e.g., a nitrogen-containing spiro heterocyclyl, e.t., 2-oxa-7-azaspiro[3.5]nonanyl). In some embodiments, the compound of Formula (II-g-i) is Compound 118.

In some embodiments, the compound is a compound of Formula (II-g-ii). In some embodiments of Formula (II-g-ii), each of $R^{2a}$, $R^{2b}$, $R^{2c}$, and $R^{2d}$ is independently hydrogen, m is 1, n is 2, q is 1, 2, 3, or 4, p is 0, and X is $S(O)_2$. In some embodiments of Formula (II-g-ii), each of $R^{2a}$ and $R^{2b}$ is independently hydrogen, m is 1, n is 2, q is 1, 2, or 4, p is 0, and X is $S(O)_2$. In some embodiments, the compound of Formula (II-g-ii) is Compound 114, Compound 115, or Compound 116.

In some embodiments, the compound is a compound of Formula (II-b), (II-c), or (II-d). In some embodiments, the compound is a compound of Formula (II-b), (II-c), or (II-e). In some embodiments, the compound is a compound of Formula (II-b), (II-c), or (II-f). In some embodiments, the compound is a compound of Formula (II-b), (II-c), or (II-g).

In some embodiments, the compound of Formula (II) is not a compound disclosed in WO2012/112982, WO2012/167223, WO2014/153126, WO2016/019391, WO 2017/075630, US2012-0213708, US 2016-0030359 or US 2016-0030360.

In some embodiments, the compound of Formula (II) comprises a compound shown in Table 2, or a pharmaceutically acceptable salt thereof.

TABLE 2
| Exemplary compounds of Formula (II) | |
|---|---|
| Compound No. | Structure |
| 100 | 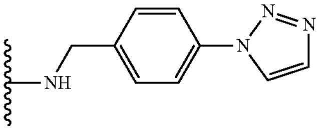 [SMILES: *NCc1ccc(-n2ccnn2)cc1] |
| 101 | 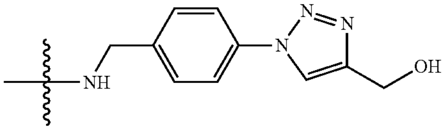 [SMILES: *NCc1ccc(-n2cc(CO)nn2)cc1] |
| 102 | 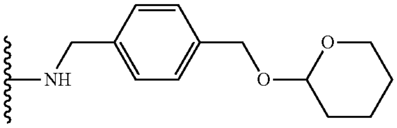 [SMILES: *NCc1ccc(COC2CCCCO2)cc1] |
| 103 | 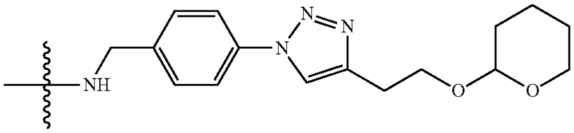 [SMILES: *NCc1ccc(-n2cc(CCOC3CCCCO3)nn2)cc1] |
| 104 | 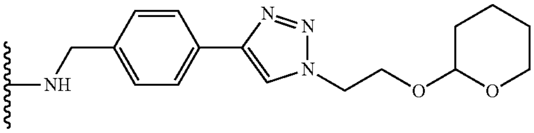 [SMILES: *NCc1ccc(-c2cn(CCOC3CCCCO3)nn2)cc1] |
| 105 | 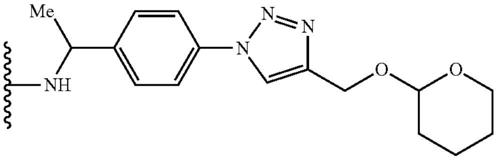 [SMILES: *NC(C)c1ccc(-n2cc(COC3CCCCO3)nn2)cc1] |
| 106 | 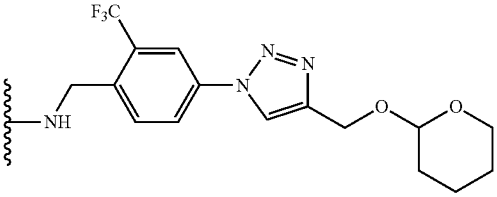 [SMILES: *NCc1ccc(-n2cc(COC3CCCCO3)nn2)cc1C(F)(F)F] |
| 107 | 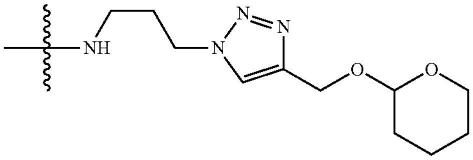 [SMILES: *NCCCn1cc(COC2CCCCO2)nn1] |
| 108 | 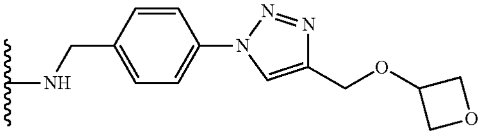 [SMILES: *NCc1ccc(-n2cc(COC3COC3)nn2)cc1] |

TABLE 2-continued
| Exemplary compounds of Formula (II) | |
|---|---|
| Compound No. | Structure |
| 109 | 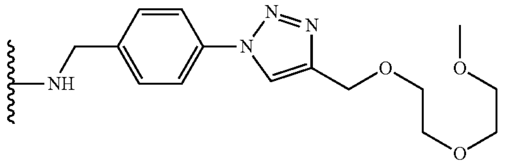 [SMILES: *NCc1ccc(-n2cc(COCCOCCOC)nn2)cc1] |
| 110 | 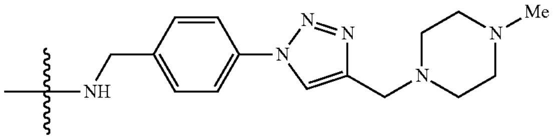 [SMILES: *NCc1ccc(-n2cc(CN3CCN(C)CC3)nn2)cc1] |
| 111 | 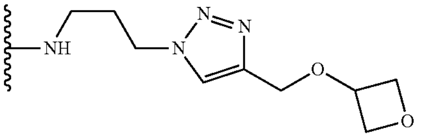 [SMILES: *NCCCn1cc(COC2COC2)nn1] |
| 112 | 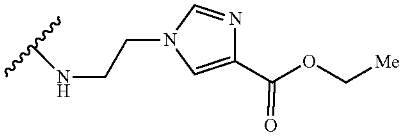 [SMILES: *NCCn1cnc(C(=O)OCC)c1] |
| 113 | 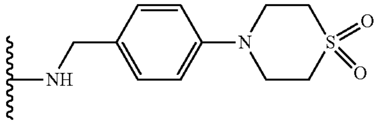 [SMILES: *NCc1ccc(N2CCS(=O)(=O)CC2)cc1] |
| 114 | 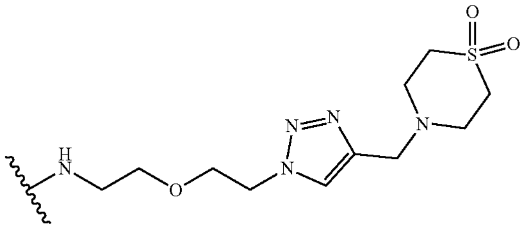 [SMILES: *NCCOCCn1cc(CN2CCS(=O)(=O)CC2)nn1] |
| 115 | 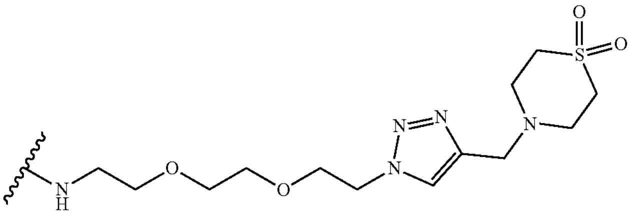 [SMILES: *NCCOCCOCCn1cc(CN2CCS(=O)(=O)CC2)nn1] |
| 116 | 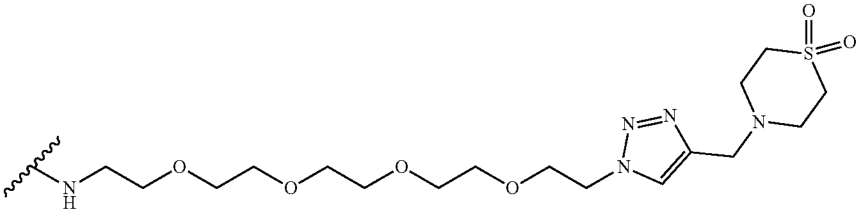 [SMILES: *NCCOCCOCCOCCOCCn1cc(CN2CCS(=O)(=O)CC2)nn1] |

TABLE 2-continued

| Exemplary compounds of Formula (II) | |
|---|---|
| Compound No. | Structure |
| 117 | 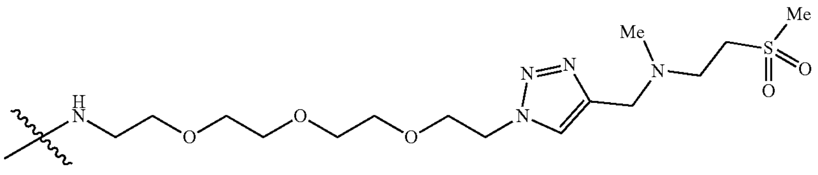 [SMILES: *NCCOCCOCCOCCn1cc(CN(C)CCS(C)(=O)=O)nn1] |
| 118 | 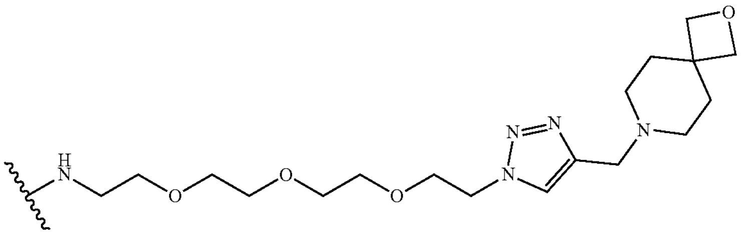 [SMILES: *NCCOCCOCCOCCn1cc(CN2CCC3(CC2)COC3)nn1] |

A polymer modified with a compound of Formula (II) or a pharmaceutically acceptable salt thereof may be a linear, branched, or cross-linked polymer, or a polymer of selected molecular weight ranges, degree of polymerization, viscosity or melt flow rate. Branched polymers can include one or more of the following types: star polymers, comb polymers, brush polymers, dendronized polymers, graft-co(polymers), ladders, and dendrimers. A polymer may be a thermoresponsive polymer, e.g., a gel (e.g., becomes a solid or liquid upon exposure to heat or a certain temperature) or a photocrosslinkable polymer. Exemplary polymers include polystyrene, polyethylene, polypropylene, polyacetylene, poly(vinyl chloride) (PVC), polyolefin copolymers, poly(urethane)s, polyacrylates and polymethacrylates, polyacrylamides and polymethacrylamides, poly(methyl methacrylate), poly(2-hydroxyethyl methacrylate), polyesters, polysiloxanes, polydimethylsiloxane (PDMS), polyethers, poly(orthoester), poly(carbonates), poly(hydroxyalkanoate)s, polyfluorocarbons, PEEK®, Teflon® (polytetrafluoroethylene, PTFE), PEEK, silicones, epoxy resins, Kevlar®, Dacron® (a condensation polymer obtained from ethylene glycol and terephthalic acid), polyethylene glycol, nylon, polyalkenes, phenolic resins, natural and synthetic elastomers, adhesives and sealants, polyolefins, polysulfones, polyacrylonitrile, biopolymers such as polysaccharides and natural latex, collagen, cellulosic polymers (e.g., alkyl celluloses, etc.), polyethylene glycol and 2-hydroxyethyl methacrylate (HEMA), polysaccharides, poly(glycolic acid), poly(L-lactic acid) (PLLA), poly(lactic glycolic acid) (PLGA), a polydioxanone (PDA), or racemic poly(lactic acid), polycarbonates, (e.g., polyamides (e.g., nylon)), fluoroplastics, carbon fiber, agarose, alginate, chitosan, and blends or copolymers thereof. In some embodiments, the polymer comprises poly(ethylene oxide). In some embodiments, the polymer comprises polyvinyl alcohol (PVA). In some embodiments, a polymer is made up of a single type of repeating monomeric unit. In other embodiments, a polymer is made up of different types of repeating monomeric units (e.g., two types of repeating monomeric units, three types of repeating monomeric units, e.g., a polymeric blend).

In some embodiments, the polymer is a polyethylene. Exemplary polyethylenes include ultra-low-density polyethylene (ULDPE) (e.g., with polymers with densities ranging from 0.890 to 0.905 $g/cm^3$, containing comonomer); very-low-density polyethylene (VLDPE) (e.g., with polymers with densities ranging from 0.905 to 0.915 $g/cm^3$, containing comonomer); linear low-density polyethylene (LLDPE) (e.g., with polymers with densities ranging from 0.915 to 0.935 $g/cm^3$, contains comonomer); low-density polyethylene (LDPE) (e.g., with polymers with densities ranging from about 0.915 to 0.935 $g/m^3$); medium density polyethylene (MDPE) (e.g., with polymers with densities ranging from 0.926 to 0.940 $g/cm^3$, may or may not contain comonomer); high-density polyethylene (HDPE) (e.g., with polymers with densities ranging from 0.940 to 0.970 $g/cm^3$, may or may not contain comonomer).

In some embodiments, the polymer is a polypropylene. Exemplary polypropylenes include homopolymers, random copolymers (homophasic copolymers), and impact copolymers (heterophasic copolymers), e.g., as described in McKeen, *Handbook of Polymer Applications in Medicine and Medical Devices,* 3-Plastics Used in Medical Devices, (2014):21-53, which is incorporated herein by reference in its entirety.

In some embodiments, the polymer is a polystyrene. Exemplary polystyrenes include general purpose or crystal (PS or GPPS), high impact (HIPS), and syndiotactic (SPS) polystyrene.

In some embodiments, the polymer is a thermoplastic elastomer (TPE). Exemplary TPEs include (i) TPA—polyamide TPE, comprising a block copolymer of alternating hard and soft segments with amide chemical linkages in the hard blocks and ether and/or ester linkages in the soft blocks; (ii) TPC—copolyester TPE, consisting of a block copolymer of alternating hard segments and soft segments, the chemical linkages in the main chain being ester and/or ether; (iii) TPO—olefinic TPE, consisting of a blend of a polyolefin and a conventional rubber, the rubber phase in the blend having little or no cross-linking; (iv) TPS—styrenic TPE, consisting of at least a triblock copolymer of styrene and a specific diene, where the two end blocks (hard blocks) are polystyrene and the internal block (soft block or blocks) is a polydiene or hydrogenated polydiene; (v) TPU—urethane TPE, consisting of a block copolymer of alternating hard and soft segments with urethane chemical linkages in the hard blocks and ether, ester or carbonate linkages or mixtures of them in the soft blocks; (vi) TPV—thermoplastic rubber vulcanizate consisting of a blend of a thermoplastic material and a conventional rubber in which the rubber has been cross-linked by the process of dynamic vulcanization during the blending and mixing step; and (vii) TPZ—unclassified TPE comprising any composition or structure other than those grouped in TPA, TPC, TPO, TPS, TPU, and TPV.

In some embodiments, the polymer is a hydrogel-forming polymer. Hydrogel-forming polymers comprise a hydrophilic structure that renders them capable of holding large amounts of water in a three-dimensional network. Hydrogel-forming polymers may include polymers which form homopolymeric hydrogels, copolymeric hydrogels, or multipolymer interpenetrating polymeric hydrogels, and may be amorphous, semicrystalline, or crystalline in nature, e.g., as described in Ahmed (2015) *J Adv Res* 6:105-121. Exemplary hydrogel-forming polymers include proteins (e.g., collagen), gelatin, polysaccharides (e.g., starch, alginate, hyaluronate, agarose), and synthetic polymers. In some embodiments, the hydrogel-forming polymer is a polysaccharide (e.g., alginate).

In some embodiments, the polymer is a polysaccharide. Exemplary polysaccharides include alginate, agar, agarose, carrageenan, hyaluronate, amylopectin, glycogen, gelatin, cellulose, amylose, chitin, chitosan, or a derivative or variant thereof, e.g., as described in Laurienzo (2010), *Mar Drugs* 9:2435-65. A polymer may comprise heparin, chondoitin sulfate, dermatan, dextran, or carboxymethylcellulose. In some embodiments, a polysaccharide is a cross-linked polymer. In some embodiments, a polysaccharide is a cell-surface polysaccharide.

In some embodiments, the polymer is a polysaccharide, and the polysaccharide is alginate. Algnate is a polysaccharide made up of β-D-mannuronic acid (M) and α-L-guluronic acid (G). In some embodiments, the alginate is a high guluronic acid (G) alginate, and comprises greater than about 50%, 55%, 60%, 65%, 70%, 75%, 80%, 85%, 90%, or more guluronic acid (G). In some embodiments, the alginate is a high mannuronic acid (M) alginate, and comprises greater than about 50%, 55%, 60%, 65%, 70%, 75%, 80%, 85%, 90%, or more mannuronic acid (M). In some embodiments, the ratio of M:G is about 1. In some embodiments, the ratio of M:G is less than 1. In some embodiments, the ratio of M:G is greater than 1.

A polymer modified with a compound of Formula (II) or a pharmaceutically acceptable salt thereof may be modified on one or more monomeric units. In some embodiments, at least 0.5% of the monomers of a polymer are modified with a compound of Formula (II) (e.g., at least 1%, 2.5%, 5%, 10%, 15%, 20%, 25%, 30%, 35%, 40%, 45%, 50%, 55%, 60%, 65%, 70%, 75%, 80%, 85%, 90%, 95%, 99%, or more of the monomers of a polymer are modified with a compound of Formula (II). In some embodiments, 0.5% to 50%, 10% to 90%, 10% to 50%, or 25-75%, of the monomers of a polymer are modified with a compound of Formula (II). In some embodiments, 1% to 20% of the monomers of a polymer are modified with a compound of Formula (II). In some embodiments, 1% to 10% of the monomers of a polymer are modified with a compound of Formula (II).

In some embodiments, the polymer (when modified with a compound of Formula II) comprises an increase in % N (as compared with unmodified polymer) of at least 0.1, 0.2, 0.5, 1.0, 1.5, 2, 2.5, 3, 3.5, 4, 4.5, 5, 5.5, 6, 6.5, 7, 7.5, 8, 8.5, 9, 9.5, or 10% N by weight, where % N is determined by elemental analysis and corresponds to the amount of compound of Formula II in the modified polymer.

In some embodiments, the polymer (when modified with a compound of Formula II) comprises an increase in % N (as compared with unmodified polymer) of 0.1 to 10% N by weight, where % N is determined by elemental analysis and corresponds to the amount of compound of Formula II in the modified polymer.

In some embodiments, the polymer (when modified with a compound of Formula II) comprises an increase in % N (as compared with unmodified polymer) of 0.1 to 2% N by weight, where % N is determined by elemental analysis and corresponds to the amount of compound of Formula II in the modified polymer.

In some embodiments, the polymer (when modified with a compound of Formula II) comprises an increase in % N (as compared with unmodified polymer) of 2 to 4% N by weight, where % N is determined by elemental analysis and corresponds to the amount of compound of Formula II in the modified polymer.

In some embodiments, the polymer (when modified with a compound of Formula II) comprises an increase in % N (as compared with unmodified polymer) of 4 to 8% N by weight, where % N is determined by elemental analysis and corresponds to the amount of compound of Formula II in the modified polymer.

An alginate modified with a compound of Formula (II) or a pharmaceutically acceptable salt thereof may be modified on one or more monomeric units. In some embodiments, at least 0.5% of the monomers in an alginate are modified with a compound of Formula (II) (e.g., at least 1%, 2.5%, 5%, 10%, 15%, 20%, 25%, 30%, 35%, 40%, 45%, 50%, 55%, 60%, 65%, 70%, 75%, 80%, 85%, 90%, 95%, 99%, or more of the monomers of an alginate are modified with a compound of Formula (II). In some embodiments, 0.5% to 50%, 10% to 90%, 10% to 50%, or 25-75%, of the monomers of an alginate are modified with a compound of Formula (II). In some embodiments, 1% to 20% of the monomers of an alginate are modified with a compound of Formula (II). In some embodiments, 1% to 10% of the monomers of an alginate are modified with a compound of Formula (II).

In some embodiments, an alginate is modified with a compound of Formula (II) (e.g., a compound of Formulas (II-a), (II-b), (II-b-i), (II-b-ii), (II-b-iii), (II-c), (II-d), (II-e), (II-e-i), (II-f), (II-g), (II-g-i), or (II-g-ii), or a pharmaceutically acceptable salt thereof). In some embodiments, an alginate is modified with a compound of Formula (II-a). In some embodiments, an alginate is modified with a compound of Formula (II-b). In some embodiments, an alginate is modified with a compound of Formula (II-b-i). In some embodiments, an alginate is modified with a compound of Formula (II-b-ii). In some embodiments, an alginate is modified with a compound of Formula (II-b-iii). In some embodiments, an alginate is modified with a compound of Formula (II-c). In some embodiments, an alginate is modified with a compound of Formula (II-d). In some embodiments, an alginate is modified with a compound of Formula (II-e). In some embodiments, an alginate is modified with a compound of Formula (II-e-i). In some embodiments, an alginate is modified with a compound of Formula (II-f). In some embodiments, an alginate is modified with a compound of Formula (II-g). In some embodiments, an alginate is modified with a compound of Formula (II-g-i). In some embodiments, an alginate is modified with a compound of Formula (II-g-ii).

In some embodiments, an alginate is modified with a compound shown in Table 2. In some embodiments, an alginate is modified with Compound 100. In some embodiments, an alginate is modified with Compound 101. In some embodiments, an alginate is modified with Compound 102. In some embodiments, an alginate is modified with Compound 103. In some embodiments, an alginate is modified with Compound 104. In some embodiments, an alginate is modified with Compound 105. In some embodiments, an alginate is modified with Compound 106. In some embodiments, an alginate is modified with Compound 107. In some embodiments, an alginate is modified with Compound 108. In some embodiments, an alginate is modified with Compound 109. In some embodiments, an alginate is modified with Compound 110. In some embodiments, an alginate is modified with Compound 111. In some embodiments, an alginate is modified with Compound 112. In some embodiments, an alginate is modified with Compound 113. In some embodiments, an alginate is modified with Compound 114. In some embodiments, an alginate is modified with Compound 115. In some embodiments, an alginate is modified with Compound 116. In some embodiments, an alginate is modified with Compound 117. In some embodiments, an alginate is modified with Compound 118.

Implantable Elements

The disclosure also features an implantable element (e.g., a device or material) comprising a compound of Formula (II) or a pharmaceutically acceptable salt thereof, as described herein. The compound of Formula (II) modification may impart an improved property to the implantable element when administered to a subject, e.g., modulation of the immune response in the subject, compared with an unmodified implantable element that is otherwise identical to the modified implantable element.

In some embodiments, the implantable element comprises a cell. In some embodiments, the cell is an engineered cell. In some embodiments, the cell is entirely or partially disposed with the implantable element. The implantable element may comprise an enclosing element that encapsulates or coats a cell, in part or in whole. In an embodiment, an implantable element comprises an enclosing component that is formed, or could be formed, in situ on or surrounding a cell, e.g., a plurality of cells, e.g., a cluster of cells, or on a microcarrier, e.g., a bead, or a matrix comprising a cell or cells.

Implantable elements can include any material, such as a material described herein. In some embodiments, an implantable element is made up of one material or many types of materials. Implantable elements can comprise non organic or metal components or materials, e.g., steel (e.g., stainless steel), titanium, other metal or alloy. Implantable elements can include nonmetal components or materials, e.g., ceramic, or hydroxyapatite elements.

Implantable elements can include components or materials that are made of a conductive material (e.g., gold, platinum, palladium, titanium, copper, aluminum, silver, metals, any combinations of these, etc.).

Implantable elements can include more than one component, e.g., more than one component disclosed herein, e.g., more than one of a metal, plastic, ceramic, composite, or hybrid material.

Exemplary implantable elements comprise materials such as metals, metallic alloys, ceramics, polymers, fibers, inert materials, and combinations thereof. An implantable element may be completely made up of one type of material, or may just refer to a surface or the surface of an implantable element (e.g., the outer surface or an inner surface).

In some embodiments, the implantable element (e.g., a device or material) comprises a metal or a metallic alloy. Exemplary metallic or metallic alloys include comprising titanium and titanium group alloys (e.g., nitinol, nickel titanium alloys, thermo-memory alloy materials), platinum, platinum group alloys, stainless steel, tantalum, palladium, zirconium, niobium, molybdenum, nickel-chrome, chromium molybdenum alloys, or certain cobalt alloys (e.g., cobalt-chromium and cobalt-chromium-nickel alloys, e.g., ELGILOY® and PHYNOX®). For example, a metallic material may be stainless steel grade 316 (SS 316L) (comprised of Fe, <0.3% C, 16-18.5% Cr, 10-14% Ni, 2-3% Mo, <2% Mn, <1% Si, <0.45% P, and <0.03% S). In metal-containing implantable elements, the amount of metal (e.g., by % weight, actual weight) can be at least 5%, e.g., at least 5%, 10%, 20%, 30%, 40%, 50%, 60%, 70%, 80%, 90%, 95%, 99%, or more, e.g., w/w; less than 20%, e.g., less than 20%, 15%, 10%, 5%, 1%, 0.5%, 0.1%, or less.

In some embodiments, the implantable element (e.g., a device or material) is a ceramic. Exemplary ceramic materials include oxides, carbides, or nitrides of the transition elements, such as titanium oxides, hafnium oxides, iridium oxides, chromium oxides, aluminum oxides, and zirconium oxides. Silicon based materials, such as silica, may also be used. In ceramic-containing implantable elements, the amount of ceramic (e.g., by % weight, actual weight) can be at least 5%, e.g., at least 5%, 10%, 20%, 30%, 40%, 50%, 60%, 70%, 80%, 90%, 95%, 99%, or more, e.g., w/w; less than 20%, e.g., less than 20%, 15%, 10%, 5%, 1%, 0.5%, 0.1%, or less.

In some embodiments, an implantable element comprises a polymer (e.g., hydrogel, plastic) component. Exemplary polymers include polyethylene, polypropylene, polystyrene, polyester (e.g., PLA, PLG, or PGA, polyhydroxyalkanoates (PHAs), or other biosorbable plastic), polycarbonate, polyvinyl chloride (PVC), polyethersulfone (PES), polyacrylate (e.g., acrylic or PMMA), hydrogel (e.g., acrylic polymer or blend of acrylic and silicone polymers), polysulfone, polyetheretherketone, thermoplastic elastomers (TPE or TPU), thermoset elastomer (e.g., silicone (e.g., silicone elastomer)), poly-p-xylylene (Parylene), fluoropolymers (e.g., PTFE), and polyacrylics such as poly(acrylic acid) and/or poly(acrylamide), or mixtures thereof. In polymer-containing implantable elements, the amount of polymer (e.g., by % weight, actual weight) can be at least 5%, e.g., at least 5%, 10%, 20%, 30%, 40%, 50%, 60%, 70%, 80%, 90%, 95%, 99%, or more, e.g., w/w; less than 20%, e.g., less than 20%, 15%, 10%, 5%, 1%, 0.5%, 0.1%, or less.

In some embodiments, the implantable element (e.g., a device or material) comprises a polymer that is covalently or non-covalently associated with the implantable element (e.g., the surface of the implantable element). In some embodiments, the polymer is covalently associated with the implantable element (e.g., on the inner surface or outer surface of an implantable element). In some embodiments, the polymer is non-covalently associated with the implantable element (e.g., on the inner surface or outer surface of an implantable element). The polymer can be applied to an implantable element by a variety of techniques in the art including, but not limited to, spraying, wetting, immersing, dipping, such as dip coating (e.g., intraoperative dip coating), painting, or otherwise applying a hydrophobic polymer to a surface of the implantable element.

In an embodiment, the implantable element comprises a flexible polymer, e.g., alginate (e.g., a chemically modified alginate), PLA, PLG, PEG, CMC, or mixtures thereof (referred to herein as a "polymer encapsulated implantable device").

In some embodiments, the implantable element comprises a hydrogel-forming polymer. Hydrogel-forming polymers comprise a hydrophilic structure that renders them capable of holding large amounts of water in a three-dimensional network. Hydrogel-forming polymers may include polymers which form homopolymeric hydrogels, copolymeric hydrogels, or multipolymer interpenetrating polymeric hydrogels, and may be amorphous, semicrystalline, or crystalline in nature, e.g., as described in Ahmed (2015) *J Adv Res* 6:105-121. Exemplary hydrogel-forming polymers include proteins (e.g., collagen), gelatin, polysaccharides (e.g., starch, alginate, hyaluronate, agarose), and synthetic polymers. In some embodiments, the hydrogel-forming polymer is a polysaccharide (e.g., alginate).

In some embodiments, the implantable element comprises a polysaccharide. Exemplary polysaccharides include alginate, agar, agarose, carrageenan, hyaluronate, amylopectin, glycogen, gelatin, cellulose, amylose, chitin, chitosan, or a derivative or variant thereof, e.g., as described in Laurienzo (2010), *Mar Drugs* 9:2435-65. An implantable element may comprise a polysaccharide comprising heparin, chondoitin sulfate, dermatan, dextran, or carboxymethylcellulose. In some embodiments, a polysaccharide is a cross-linked polymer. In some embodiments, a polysaccharide is a cell-surface polysaccharide.

In some embodiments, the implantable element comprises a polysaccharide, and the polysaccharide is alginate. Alginate is a polysaccharide made up of βP-D-mannuronic acid (M) and α-L-guluronic acid (G). In some embodiments, the alginate is a high guluronic acid (G) alginate, and comprises greater than about 50%, 55%, 60%, 65%, 70%, 75%, 80%, 85%, 90%, or more guluronic acid (G). In some embodiments, the alginate is a high mannuronic acid (M) alginate, and comprises greater than about 50%, 55%, 60%, 65%, 70%, 75%, 80%, 85%, 90%, or more mannuronic acid (M). In some embodiments, the ratio of M:G is about 1. In some embodiments, the ratio of M:G is less than 1. In some embodiments, the ratio of M:G is greater than 1.

In an embodiment, an implantable element comprises is formed, or could be formed, in situ on or surrounding cell, e.g., a plurality of cells, e.g., a cluster of cells, or on a microcarrier, e.g., a bead, or a matrix comprising cell or cells.

In an embodiment, an implantable element comprises is preformed prior to combination with the enclosed cell, e.g., a plurality of cells, e.g., a cluster of cells, or on a microcarrier, e.g., a bead, or a matrix comprising cell or cells. An implantable element can include a protein or polypeptide, e.g., an antibody, protein, enzyme, or growth factor. An implantable element can include an active or inactive fragment of a protein or polypeptide, such as glucose oxidase (e.g., for glucose sensor), kinase, phosphatase, oxygenase, hydrogenase, reductase.

Implantable elements included herein include implantable elements that are configured with a lumen, e.g., a lumen having one, two or more openings, e.g., tubular devices. A typical stent is an example of a device configured with a lumen and having two openings. Other examples include shunts.

Implantable elements included herein include flexible implantable elements, e.g., that are configured to conform to the shape of the body.

Implantable elements included herein include components that stabilize the location of the implantable element, e.g., an adhesive, or fastener, e.g., a torque-based or friction-based fastener, e.g., a screw or a pin.

Implantable elements included herein may be configured to monitor a substance, e.g., an exogenous substance, e.g., a therapeutic agent or toxin, or an endogenous body product, e.g., a polypeptide e.g., insulin. In some embodiments, the implantable element is a diagnostic.

Implantable elements included herein may be configured to release a substance, e.g., an exogenous substance, e.g., a therapeutic agent described herein. In some embodiments, the therapeutic agent is a compound of Formula (II) or a pharmaceutically acceptable salt thereof. In some embodiments, the therapeutic agent is a biological material. In some embodiments, the therapeutic agent is a nucleic acid (e.g., an RNA or DNA), protein (e.g., a hormone, enzyme, antibody, antibody fragment, antigen, or epitope), small molecule, lipid, drug, vaccine, or any derivative thereof.

Implantable elements herein may be configured to change conformation in response to a signal or movement of the body, e.g., an artificial joint, e.g., a knee, hip, or other artificial joint.

Exemplary implantable elements include a stent, shunt, dressing, ocular device, port, sensor, orthopedic fixation device, implant (e.g., a dental implant, ocular implant, silicon implant, corneal implant, dermal implant, intragastric implant, facial implant, hip implant, bone implant, cochlear implant, penile implant, implants for control of incontinence), skin covering device, dialysis media, drug-delivery device, artificial or engineered organ (e.g., a spleen, kidney, liver, or heart), drainage device (e.g., a bladder drainage device), cell selection system, adhesive (e.g., a cement, clamp, clip), contraceptive device, intrauterine device, defibrillator, dosimeter, electrode, pump (e.g., infusion pump) filter, embolization device, fastener, fillers, fixative, graft, hearing aid, cardio or heart-related device (e.g., pacemaker, heart valve), battery or power source, hemostatic agent, incontinence device, intervertebral body fusion device, intraoral device, lens, mesh, needle, nervous system stimulator, patch, peritoneal access device, plate, plug, pressure monitoring device, ring, transponder, and valve. Also included are devices used in one or more of anesthesiology, cardiology, clinical chemistry, otolaryngology, dentistry, gastroenterology, urology, hematology, immunology, microbiology, neurology, obstetrics/gynecology, ophthalmology, orthopedic, pathology, physical medicine, radiology, general or plastic surgery, veterinary medicine, psychiatry, surgery, and/or clinical toxicology.

Implantable elements included herein include FDA class 1, 2, or 3 devices, e.g., devices that are unclassified or not classified, or classified as a humanitarian use device (HUD).

In some embodiments, an implantable element includes encapsulated or entrapped cells or tissues. The cells or tissue can be encapsulated or entrapped in a polymer. In some embodiments, an implantable element includes an MSFC, e.g., an MSFC disposed within a polymeric enclosing component (e.g., alginate).

In some embodiments, an implantable element targets or is designed for a certain system of the body, e.g. the nervous system (e.g., peripheral nervous system (PNS) or central nervous system (CNS)), vascular system, skeletal system, respiratory system, endocrine system, lymph system, reproductive system, or gastrointestinal tract. In some embodiments, an implantable element is targeted to the CNS. In some embodiments, an implantable element targets or is designed for a certain part of the body, e.g., blood, eye, brain, skin, lung, stomach, mouth, ear, leg, foot, hand, liver, heart, kidney, bone, pancreas, spleen, large intestine, small intestine, spinal cord, muscle, ovary, uterus, vagina, or penis.

Components or materials used in an implantable element (or the entire implantable element) can be optimized for one or more of biocompatibility (e.g., it minimizes immune rejection or fibrosis; heat-resistance; elasticity; tensile strength; chemical resistance (e.g., resistance to oils, greases, disinfectants, bleaches, processing aids, or other chemicals used in the production, use, cleaning, sterilizing and disinfecting of the device); electrical properties; surface and volume conductivity or resistivity, dielectric strength; comparative tracking index; mechanical properties; shelf life, long term durability sterilization capability (e.g., capable of withstanding sterilization processes, such as steam, dry heat, ethylene oxide (EtO), electron beam, and/or gamma radiation, e.g., while maintaining the properties for the intended use of the device), e.g., thermal resistance to autoclave/steam conditions, hydrolytic stability for steam sterilization, chemical resistance to EtO, resistance to high-energy radiation (e.g., electron beam, UV, and gamma); or crystal structure.

An implantable element can be assembled in vivo (e.g., injectable substance that forms a structured shape in vivo, e.g., at body temperature) or ex vivo.

An implantable element can have nanodimensions, e.g., can comprise a nanoparticle, e.g., nanoparticle made of a polymer described herein, e.g., PLA. Nanoparticles can be chemically modified nanoparticles, e.g., modified to prevent uptake by macrophages and Kupfer cells (e.g., a process called opsonization); or to alter the circulation half-life of the nanoparticle. Nanoparticles can include iron nanoparticle (injectable) (e.g., Advanced Magnetics iron nanoparticles). Exemplary nanoparticles are described in Veiseh et al (2010) *Adv Drug Deliv Rev* 62:284-304, which is incorporated herein by reference in its entirety.

An implantable element can be configured for implantation, or implanted or disposed into or onto any site of the body. In some embodiments, an implantable element is configured for implantation, implanted or disposed into the omentum of a subject, into the subcutaneous fat of a subject, or into the muscle tissue of a subject. An implantable element can be configured for implantation, or implanted, or disposed on or in the skin; a mucosal surface, a body cavity, the peritoneal cavity (e.g., the lesser sac); the central nervous system, e.g., the brain or spinal cord; an organ, e.g., the heart, liver, kidney, spleen, lung, lymphatic system, vasculature, the oral cavity, the nasal cavity, the teeth, the gums, the GI tract; bone; hip; fat tissue; muscle tissue; circulating blood; the eye (e.g., intraocular); breast, vagina; uterus, a joint, e.g., the knee or hip joint, or the spine.

In some embodiments, the implantable element is configured for implantation or implanted or disposed into the peritoneal cavity (e.g., the omentum). In some embodiments, the implantable element is configured for implantation or implanted or disposed into or onto the lesser sac, also known as the omental bursa or bursalis omentum. The lesser sac refers to a cavity located in the abdomen formed by the omentum, and is in close proximity to, for example, the greater omentum, lesser omentum, stomach, small intestine, large intestine, liver, spleen, gastrosplenic ligament, adrenal glands, and pancreas. Typically, the lesser sac is connected to the greater sac via the omental foramen (i.e., the Foramen of Winslow). In some embodiments, the lesser sac comprises a high concentration of adipose tissue. An implantable element may be implanted in the peritoneal cavity (e.g., the omentum, e.g., the lesser sac) or disposed on a surface within the peritoneal cavity (e.g., omentum, e.g., lesser sac) via injection or catheter. Additional considerations for implantation or disposition of an implantable element into the omentum (e.g., the lesser sac) are provided in M. Pellicciaro et al. (2017) *Cell* R4 5(3):e2410, which is incorporated herein by reference in its entirety.

In some embodiments, the implantable element is configured for implantation or implanted or disposed into the central nervous system (CNS), e.g., the brain or spinal cord and their corresponding tissues and cavities. In vertebrates, the CNS is contained within the dorsal body cavity, including the cranial cavity and the spinal canal. In some embodiments, the implantable element is configured for implantation or implanted or disposed into an intracerebral space, e.g., the intraparenchymal space, the intraventricular space, or the subdural space. An implantable element may be implanted in the CNS or disposed on a surface within the CNS through a hole made in the skull and delivered via injection or catheter.

In some embodiments, the implantable element is configured for implantation or implanted in or disposed into the eye. Exemplary regions suitable for implantation or disposition of the implantable element include any surface or cavity within the eye, such as the retina, cornea, epithelium, aqueous humor, or vitreal space. In some embodiments, the implantable element is configured for implantation or implanted or disposed into the vitreal space. An implantable element may be implanted in the eye or disposed on a surface within the eye through incision and/or injection.

An implantable element can comprise an electrochemical sensor, e.g., an electrochemical sensor including a working electrode and a reference electrode. For example, an electrochemical sensor includes a working electrode and a reference electrode that reacts with an analyte to generate a sensor measurement related to a concentration of the analyte in a fluid to which the eye-mountable device is exposed. The implantable element can comprise a window, e.g., of a transparent polymeric material having a concave surface and a convex surface a substrate, e.g., at least partially embedded in a transparent polymeric material. An implantable element can also comprise an electronics module including one or more of an antenna; and a controller electrically connected to the electrochemical sensor and the antenna, wherein the controller is configured to control the electrochemical sensor to obtain a sensor measurement related to a concentration of an analyte in a fluid to which the implantable element, e.g., an mountable implantable element is exposed and use the antenna to indicate the sensor measurement.

In some embodiments, an implantable element has a mean diameter or size that is greater than 1 mm, preferably 1.5 mm or greater. In some embodiments, an implantable element can be as large as 8 mm in diameter or size. For example, an implantable element described herein is in a size range of 1 mm to 8 mm, 1 mm to 6 mm, 1 mm to 5 mm, 1 mm to 4 mm, 1 mm to 3 mm, 1 mm to 2 mm, 1 mm to 1.5 mm, 1.5 mm to 8 mm, 1.5 mm to 6 mm, 1.5 mm to 5 mm, 1.5 mm to 4 mm, 1.5 mm to 3 mm, 1.5 mm to 2 mm, 2 mm to 8 mm, 2 mm to 7 mm, 2 mm to 6 mm, 2 mm to 5 mm, 2 mm to 4 mm, 2 mm to 3 mm, 2.5 mm to 8 mm, 2.5 mm to 7 mm, 2.5 mm to 6 mm, 2.5 mm to 5 mm, 2.5 mm to 4 mm, 2.5 mm to 3 mm, 3 mm to 8 mm, 3 mm to 7 mm, 3 mm to 6 mm, 3 mm to 5 mm, 3 mm to 4 mm, 3.5 mm to 8 mm, 3.5 mm to 7 mm, 3.5 mm to 6 mm, 3.5 mm to 5 mm, 3.5 mm to 4 mm, 4 mm to 8 mm, 4 mm to 7 mm, 4 mm to 6 mm, 4 mm to 5 mm, 4.5 mm to 8 mm, 4.5 mm to 7 mm, 4.5 mm to 6 mm, 4.5 mm to 5 mm, 5 mm to 8 mm, 5 mm to 7 mm, 5 mm to 6 mm, 5.5 mm to 8 mm, 5.5 mm to 7 mm, 5.5 mm to 6 mm, 6 mm to 8 mm, 6 mm to 7 mm, 6.5 mm to 8 mm, 6.5 mm to 7 mm, 7 mm to 8 mm, or 7.5 mm to 8 mm. In some embodiments, the implantable element has a mean diameter or size between 1 mm to 8 mm. In some embodiments, the implantable element has a mean diameter or size between 1 mm to 4 mm. In some embodiments, the implantable element has a mean diameter or size between 1 mm to 2 mm.

In some embodiments, an implantable element comprises at least one pore or opening, e.g., to allow for the free flow of materials. In some embodiments, the mean pore size of an implantable element is between about 0.1 μm to about 10 μm. For example, the mean pore size may be between 0.1 μm to 10 μm, 0.1 μm to 5 μm, 0.1 μm to 2 μm, 0.15 μm to 10 μm, 0.15 μm to 5 μm, 0.15 μm to 2 μm, 0.2 μm to 10 μm, 0.2 μm to 5 μm, 0.25 μm to 10 μm, 0.25 μm to 5 μm, 0.5 μm to 10 μm, 0.75 μm to 10 μm, 1 μm to 10 μm, 1 μm to 5 μm, 1 μm to 2 μm, 2 μm to 10 μm, 2 μm to 5 μm, or 5 μm to 10 μm. In some embodiments, the mean pore size of an implantable element is between about 0.1 μm to 10 μm. In some embodiments, the mean pore size of an implantable element is between about 0.1 μm to 5 μm. In some embodiments, the mean pore size of an implantable element is between about 0.1 μm to 1 μm.

In some embodiments, an implantable element is capable of preventing materials over a certain size from passing through a pore or opening. In some embodiments, an implantable element is capable of preventing materials greater than 50 kD, 75 kD, 100 kD, 125 kD, 150 kD, 175 kD, 200 kD, 250 kD, 300 kD, 400 kD, 500 kD, 750 kD, 1,000 kD from passing through.

An implantable element (e.g., an implantable element described herein) may be provided as a preparation or composition for implantation or administration to a subject. In some embodiments, at least 20%, 30%, 35%, 40%, 45%, 50%, 55%, 60%, 65%, 70%, 75%, 80%, 85%, 90%, 95% or 100% of the implantable elements in a preparation or composition have a characteristic as described herein, e.g., mean pore size.

In some embodiments, an implantable element may be used for varying periods of time, ranging from a few minutes to several years. For example, an implantable element may be used from about 1 hour to about 10 years. In some embodiments, an implantable element is used for longer than about 1 hour, 2 hours, 4 hours, 8 hours, 16 hours, 1 day, 48 hours, 2 days, 3 days, 4 days, 5 days, 6 days, 1 week, 2 weeks, 1 month, 2 months, 3 months, 4 months, 5 months, 6 months, 8 months, 10 months, 1 year, 18 months, 2 years, 3 years, 4 years, 5 years, 6 years, 7 years, 8 years, 9 years, 10 years, or more. An implantable element may be configured for the duration of implantation, e.g., configured to resist fibrotic inactivation by fibrosis for all or part of the expected duration.

In some embodiments, the implantable element is easily retrievable from a subject, e.g., without causing injury to the subject or without causing significant disruption of the surrounding tissue. In an embodiment, the implantable element can be retrieved with minimal or no surgical separation of the implantable element from surrounding tissue, e.g., via minimally invasive surgical insection, extraction, or resection.

An implantable element can be configured for limited exposure (e.g., less than 2 days, e.g., less than 2 days, 1 day, 24 hours, 20 hours, 16 hours, 12 hours, 10 hours, 8 hours, 6 hours, 5 hours, 4 hours, 3 hours, 2 hours, 1 hour or less). An implantable element can be configured for prolonged exposure (e.g., at least 2 days, 3 days, 4 days, 5 days, 6 days, 7 days, 1 week, 2 weeks, 3 weeks, 4 weeks, 5 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 1 year, 1.5 years, 2 years, 2.5 years, 3 years, 3.5 years, 4 years or more) An implantable element can be configured for permanent exposure (e.g., at least 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 1 year, 1.5 years, 2 years, 2.5 years, 3 years, 3.5 years, 4 years or more).

In some embodiments, the implantable element is not an implantable element disclosed in any of WO2012/112982, WO2012/167223, WO2014/153126, WO2016/019391, US2012-0213708, US 2016-0030359, and US 2016-0030360.

In some embodiments, an implantable element is associated with a compound of Formula (II). In some embodiments, an implantable element is covalently modified with a compound of Formula (II). In some embodiments, an implantable element comprises a polymer modified with a compound of Formula (II). In some embodiments, an implantable element comprises a polymer modified with a compound of Formula (II) and a cell that is entirely or partially disposed within the implantable element.

In some embodiments, a surface of the implantable element comprising a cell (e.g., an engineered cell) is chemically modified with a compound of Formula (II). In some embodiments, a surface comprises an outer surface or an inner surface of the implantable element. In some embodiments, the surface (e.g., outer surface) of the implantable element comprising a cell (e.g., an engineered cell) is chemically modified with a compound of Formula (II). In some embodiments, the surface (e.g., outer surface) is covalently linked to a compound of Formula (II).

An implantable element may be coated with a compound of Formula (II) or a pharmaceutically acceptable salt thereof, or a polymer comprising a compound of Formula (II) or a pharmaceutically acceptable salt thereof. In an embodiment, the compound of Formula (II) is disposed on a surface, e.g., an inner or outer surface, of the implantable element. In some embodiments, the compound of Formula (II) is disposed on a surface, e.g., an inner or outer surface, of an enclosing component associated with an implantable element. In an embodiment, the compound of Formula (II) is distributed evenly across a surface. In an embodiment, the compound of Formula (II) is distributed unevenly across a surface.

In some embodiments, an implantable element (e.g., or an enclosing component thereof) is coated (e.g., covered, partially or in full), with a compound of Formula (II) or a polymer modified with a compound of Formula (II) or a pharmaceutically acceptable salt thereof. In some embodiments, an implantable element (e.g., or an enclosing component thereof) is coated with a single layer of a compound of Formula (II). In some embodiments, an implantable element is coated with multiple layers of a compound of Formula (II), e.g., at least 2 layers, 3 layers, 4 layers, 5 layers, 10 layers, 20 layers, 50 layers or more.

In an embodiment, a first portion of the surface of the implantable element comprises a compound of Formula (II) that modulates, e.g., downregulates or upregulates, a biological function and a second portion of the implantable element lacks the compound, or has substantially lower density of the compound.

In an embodiment a first portion of the surface of the implantable element comprises a compound of Formula (II) that modulates, e.g., down regulates, an immune response and a second portion of the surface comprises a second compound of Formula (II), e.g., that upregulates the immune response, second portion of the implantable element lacks the compound, or has substantially lower density of the compound.

In some embodiments, an implantable element is coated or chemically derivatized in a symmetrical manner with a compound of Formula (II), or a material comprising Formula (II), or a pharmaceutically acceptable salt thereof. In some embodiments, an implantable element is coated or chemically derivatized in an asymmetrical manner with a compound of Formula (II), or a polymer modified with a compound of Formula (II), or a pharmaceutically acceptable salt thereof. For example, an exemplary implantable element may be partially coated (e.g., at least about 5%, 10%, 15%, 20%, 25%, 30%, 35%, 40%, 45%, 50%, 55%, 60%, 65%, 70%, 75%, 80%, 85%, 90%, 95%, 99%, or 99.9% coated) with a compound of Formula (I) or a polymer modified with a compound of Formula (II) or a pharmaceutically acceptable salt thereof.

Exemplary implantable elements coated or chemically derivatized with a compound of Formula (II), or a polymer modified with a compound Formula (II), or a pharmaceutically acceptable salt thereof may be prepared using any method known in the art, such as through self-assembly (e.g., via block copolymers, adsorption (e.g., competitive adsorption), phase separation, microfabrication, or masking).

In some embodiments, the implantable element comprises a surface exhibiting two or more distinct physicochemical properties (e.g., 3, 4, 5, 6, 7, 8, 9, 10, or more distinct physicochemical properties).

In some embodiments, the coating or chemical derivatization of the surface of an exemplary implantable element with a compound of Formula (II), a polymer modified with a compound of Formula (II), or a pharmaceutically acceptable salt thereof is described as the average number of attached compounds per given area, e.g., as a density. For example, the density of the coating or chemical derivatization of an exemplary implantable element may be 0.01, 0.1, 0.5, 1, 5, 10, 15, 20, 50, 75, 100, 200, 400, 500, 750, 1,000, 2,500, or 5,000 compounds per square μm or square mm, e.g., on the surface or interior of said implantable element.

An implantable element comprising a compound of Formula (II) or a pharmaceutically acceptable salt thereof may have a reduced immune response (e.g., a marker of an immune response) compared to an otherwise identical implantable element that does not comprise a compound of Formula (I) or a pharmaceutically acceptable salt thereof. A marker of immune response is one or more of: cathepsin level or the level of a marker of immune response, e.g., TNF-α, IL-13, IL-6, G-CSF, GM-CSF, IL-4, CCL2, or CCL4, as measured, e.g., by ELISA. In some embodiments, an implantable element comprising a compound of Formula (II) or a pharmaceutically acceptable salt thereof has about a 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99%, or about 100% reduced immune response (e.g., a marker of an immune response) compared to an implantable element that does not comprise a compound of Formula (II) or a pharmaceutically acceptable salt thereof. In some embodiments, the reduced immune response (e.g., a marker of an immune response) is measured after about 30 minutes, about 1 hour, about 6 hours, about 12 hours, about 1 day, about 2 days, about 3 days, about 4 days, about 1 week, about 2 weeks, about 1 month, about 2 months, about 3 months, about 6 months, or longer. In some embodiments, an implantable element comprising a compound of Formula (II) is coated by the compound of Formula (II) or encapsulated a compound of Formula (II).

An implantable element comprising a compound of Formula (II) or a pharmaceutically acceptable salt thereof may have an increased immune response (e.g., a marker of an immune response) compared to an implantable element that does not comprise a compound of Formula (II) or a pharmaceutically acceptable salt thereof. A marker of immune response is one or more of: cathepsin activity, or the level of a marker of immune response, e.g., TNF-α, IL-13, IL-6, G-CSF, GM-CSF, IL-4, CCL2, or CCL4, as measured, e.g., by ELISA. In some embodiments, a device comprising a compound of Formula (II) or a pharmaceutically acceptable salt thereof has about a 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99%, or about 100%, or about 1000% increased immune response (e.g., a marker of an immune response) compared to an implantable element that does not comprise a compound of Formula (II) or a pharmaceutically acceptable salt thereof. In some embodiments, the increased immune response (e.g., a marker of an immune response) is measured after about 30 minutes, about 1 hour, about 6 hours, about 12 hours, about 1 day, about 2 days, about 3 days, about 4 days, about 1 week, about 2 weeks, about 1 month, about 2 months, about 3 months, about 6 months, or longer. In some embodiments, an implantable element comprising a compound of Formula (II) is coated by the compound of Formula (I) or encapsulated a compound of Formula (II).

An implantable element may have a smooth surface, or may comprise a protuberance, depression, well, slit, or hole, or any combination thereof. Said protuberance, depression, well, slit or hole may be any size, e.g., from 10 μm to about 1 nm, about 5 μm to about 1 nm, about 2.5 μm to about 1 nm, 1 μm to about 1 nm, 500 nm to about 1 nm, or about 100 nm to about 1 nm. The smooth surface or protuberance, depression, well, slit, or hole, or any combination thereof, may be coated or chemically derivatized with a compound of Formula (II), polymer modified with a compound of Formula (II), or a pharmaceutically acceptable salt thereof.

An implantable element may take any suitable shape, such as a sphere, spheroid, ellipsoid, disk, cylinder, torus, cube, stadiumoid, cone, pyramid, triangle, rectangle, square, or rod, or may comprise a curved or flat section. Any shaped, curved, or flat implantable element may be coated or chemically derivatized with a compound of Formula (II), a polymer modified with a compound of Formula (II), or a pharmaceutically acceptable salt thereof.

An implantable element comprising a polymer modified with a compound of Formula (II) or a pharmaceutically acceptable salt thereof may be modified on one or more of the monomeric units of the polymer. In some embodiments, at least 0.5% of the monomers of a polymer are modified with a compound of Formula (II) (e.g., at least 1%, 2.5%, 5%, 10%, 15%, 20%, 25%, 30%, 35%, 40%, 45%, 50%, 55%, 60%, 65%, 70%, 75%, 80%, 85%, 90%, 95%, 99%, or more of the monomers of a polymer are modified with a compound of Formula (II). In some embodiments, 0.5% to 50%, 10% to 90%, 10% to 50%, or 25-75%, of the monomers of a polymer are modified with a compound of Formula (II). In some embodiments, 1% to 20% of the monomers of a polymer are modified with a compound of Formula (II). In some embodiments, 1% to 10% of the monomers of a polymer are modified with a compound of Formula (II).

In some embodiments, the implantable element (when comprising a compound of Formula II) comprises an increase in % N (as compared with an implantable element not comprising a compound of Formula II) of at least 0.1, 0.2, 0.5, 1.0, 1.5, 2, 2.5, 3, 3.5, 4, 4.5, 5, 5.5, 6, 6.5, 7, 7.5, 8, 8.5, 9, 9.5, or 10% N by weight, where % N is determined by elemental analysis and corresponds to the amount of compound of Formula II in the implantable element.

In some embodiments, the implantable element (when comprising a compound of Formula II) comprises an increase in % N (as compared with an implantable element not comprising a compound of Formula II) of 0.1 to 10% N by weight, where % N is determined by elemental analysis and corresponds to the amount of compound of Formula II in the implantable element.

In some embodiments, the implantable element (when comprising a compound of Formula II) comprises an increase in % N (as compared with an implantable element not comprising a compound of Formula II) of 0.1 to 2% N by weight, where % N is determined by elemental analysis and corresponds to the amount of compound of Formula II in the implantable element.

In some embodiments, the implantable element (when modified with a compound of Formula II) comprises an increase in % N (as compared with an implantable element not comprising a compound of Formula II) of 2 to 4% N by weight, where % N is determined by elemental analysis and corresponds to the amount of compound of Formula II in the implantable element.

In some embodiments, the implantable element (when comprising a compound of Formula II) comprises an increase in % N (as compared with an implantable element not comprising a compound of Formula II) of 4 to 8% N by weight, where % N is determined by elemental analysis and corresponds to the amount of compound of Formula II in the implantable element.

An implantable element comprising an alginate modified with a compound of Formula (II) or a pharmaceutically acceptable salt thereof may be modified on one or more of the monomeric units of the alginate. In some embodiments, at least 0.5% of the monomers of an alginate of an implantable element are modified with a compound of Formula (II) (e.g., at least 1%, 2.5%, 5%, 10%, 15%, 20%, 25%, 30%, 35%, 40%, 45%, 50%, 55%, 60%, 65%, 70%, 75%, 80%, 85%, 90%, 95%, 99%, or more of the monomers of an alginate of an implantable element are modified with a compound of Formula (II). In some embodiments, 0.5% to 50%, 10% to 90%, 10% to 50%, or 25-75%, of the monomers of an alginate of an implantable element are modified with a compound of Formula (II). In some embodiments, 1% to 20% of the monomers of an alginate of an implantable element are modified with a compound of Formula (II). In some embodiments, 1% to 10% of the monomers an alginate of an implantable element are modified with a compound of Formula (II).

In some embodiments, an implantable element comprises an alginate modified with a compound of Formula (II) (e.g., a compound of Formulas (II-a), (II-b), (II-b-i), (II-b-ii), (II-b-iii), (II-c), (II-c-i), (II-d), (II-e), (II-e-i), (II-f), (II-g), (II-g-i), or (II-g-ii), or a pharmaceutically acceptable salt thereof). In some embodiments, an implantable element comprises an alginate modified with a compound of Formula (II-a). In some embodiments, an implantable element comprises an alginate modified with a compound of Formula (II-b). In some embodiments, an implantable element comprises an alginate modified with a compound of Formula (II-b-i). In some embodiments, an implantable element comprises an alginate modified with a compound of Formula (II-b-ii). In some embodiments, an implantable element comprises an alginate modified with a compound of Formula (II-c). In some embodiments, an implantable element comprises an alginate modified with a compound of Formula (II-d). In some embodiments, an implantable element comprises an alginate modified with a compound of Formula (II-e). In some embodiments, an implantable element comprises an alginate modified with a compound of Formula (II-e-i). In some embodiments, an implantable element comprises an alginate modified with a compound of Formula (II-f). In some embodiments, an implantable element comprises an alginate modified with a compound of Formula (II-g). In some embodiments, an implantable element comprises an alginate modified with a compound of Formula (II-g-i). In some embodiments, an implantable element comprises an alginate modified with a compound of Formula (II-g-ii).

In some embodiments, an implantable element comprises an alginate modified with a compound shown in Table 2. In some embodiments, an implantable element comprises an alginate modified with Compound 100. In some embodiments, an implantable element comprises an alginate modified with Compound 101. In some embodiments, an implantable element comprises an alginate modified with Compound 102. In some embodiments, an implantable element comprises an alginate modified with Compound 103. In some embodiments, an implantable element comprises an alginate modified with Compound 104. In some embodiments, an implantable element comprises an alginate modified with Compound 105. In some embodiments, an implantable element comprises an alginate modified with Compound 106. In some embodiments, an implantable element comprises an alginate modified with Compound 107. In some embodiments, an implantable element comprises an alginate modified with Compound 108. In some embodiments, an implantable element comprises an alginate modified with Compound 109. In some embodiments, an implantable element comprises an alginate modified with Compound 110. In some embodiments, an alginate is modified with Compound 111. In some embodiments, an implantable element comprises an alginate modified with Compound 112. In some embodiments, an implantable element comprises an alginate modified with Compound 113. In some embodiments, an implantable element comprises an alginate modified with Compound 114. In some embodiments, an implantable element comprises an alginate modified with Compound 115. In some embodiments, an implantable element comprises an alginate modified with Compound 116. In some embodiments, an implantable element comprises an alginate modified with Compound 117. In some embodiments, an implantable element comprises an alginate modified with Compound 118.

Cells and Therapeutic Agents

The implantable elements of the present disclosure may comprise a wide variety of different cell types (e.g., human cells), including epithelial cells, endothelial cells, fibroblast cells, mesenchymal stem cells, and keratinocyte cells. Exemplary cell types include the cell types recited in WO 2017/075631. In an embodiment, the implantable elements described herein comprise a plurality of cells. In an embodiment, the plurality of cells is in the form of a cell suspension prior to being encapsulated within an implantable elements described herein. The cells in the suspension may take the form of single cells (e.g., from a monolayer cell culture), or provided in another form, e.g., disposed on a microcarrier (e.g., a bead or matrix) or as a three-dimensional aggregate of cells (e.g., a cell cluster or spheroid). The cell suspension can comprise multiple cell clusters (e.g., as spheroids) or microcarriers.

The present invention features a cell that produces or is capable of producing a therapeutic agent for the prevention or treatment of a disease, disorder, or condition described herein. In an embodiment, the cell is an engineered cell. The therapeutic agent may be any biological substance, such as a nucleic acid (e.g., a nucleotide, DNA, or RNA), a polypeptide, a lipid, a sugar (e.g., a monosaccharide, disaccharide, oligosaccharide, or polysaccharide), or a small molecule, each of which are further elaborated below. Exemplary therapeutic agents include the agents listed in WO 2017/075631.

In some embodiments, the cells (e.g., engineered cells) produce a nucleic acid. A nucleic acid produced by a cell described herein may vary in size and contain one or more nucleosides or nucleotides, e.g., greater than 2, 3, 4, 5, 10, 25, 50, or more nucleosides or nucleotides. In some embodiments, the nucleic acid is a short fragment of RNA or DNA, e.g., and may be used as a reporter or for diagnostic purposes. Exemplary nucleic acids include a single nucleoside or nucleotide (e.g., adenosine, thymidine, cytidine, guanosine, uridine monophosphate, inosine monophosphate), RNA (e.g., mRNA, siRNA, miRNA, RNAi), and DNA (e.g., a vector, chromosomal DNA). In some embodiments, the nucleic acid has an average molecular weight of about 0.25 kD, 0.5 kD, 1 kD, 1.5 kD, 2 kD, 2.5 kD, 5 kD, 10 kD, 25 kD, 50 kD, 100 kD, 150 kD, 200 kD, or more.

In some embodiments, the therapeutic agent is a peptide or polypeptide (e.g., a protein), such as a hormone, enzyme, cytokine (e.g., a pro-inflammatory cytokine or an anti-inflammatory cytokine), growth factor, clotting factor, or lipoprotein. A peptide or polypeptide (e.g., a protein, e.g., a hormone, growth factor, clotting factor or coagulation factor, antibody molecule, enzyme, cytokine, cytokine receptor, or a chimeric protein including cytokines or a cytokine receptor) produced by an MSFC can have a naturally occurring amino acid sequence, or may contain a variant of the naturally occurring sequence. The variant can be a naturally occurring or non-naturally occurring amino acid substitution, mutation, deletion or addition relative to the reference naturally occurring sequence. The naturally occurring amino acid sequence may be a polymorphic variant. The naturally occurring amino acid sequence can be a human or a non-human amino acid sequence. In some embodiments, the naturally occurring amino acid sequence or naturally occurring variant thereof is a human sequence. In addition, a peptide or polypeptide (e.g., a protein) for use with the present invention may be modified in some way, e.g., via chemical or enzymatic modification (e.g., glycosylation, phosphorylation). In some embodiments, the peptide has about 2, 3, 4, 5, 6, 7, 8, 9, 10, 12, 14, 16, 18, 20, 25, 30, 35, 40, 45, or 50 amino acids. In some embodiments, the protein has an average molecular weight of 5 kD, 10 kD, 25 kD, 50 kD, 100 kD, 150 kD, 200 kD, 250 kD, 500 kD, or more.

In some embodiments, the protein is a hormone. Exemplary hormones include anti-diuretic hormone (ADH), oxytocin, growth hormone (GH), prolactin, growth hormone-releasing hormone (GHRH), thyroid stimulating hormone (TSH), thyrotropin-release hormone (TRH), adrenocorticotropic hormone (ACTH), follicle-stimulating hormone (FSH), luteinizing hormone (LH), luteinizing hormone-releasing hormone (LHRH), thyroxine, calcitonin, parathyroid hormone, aldosterone, cortisol, epinephrine, glucagon, insulin, estrogen, progesterone, and testosterone. In some embodiments, the protein is insulin (e.g., insulin A-chain, insulin B-chain, or proinsulin). In some embodiments, the protein is a growth hormone, such as human growth hormone (hGH), recombinant human growth hormone (rhGH), bovine growth hormone, methione-human growth hormone, des-phenylalanine human growth hormone, and porcine growth hormone. In some embodiments, the protein is not insulin (e.g., insulin A-chain, insulin B-chain, or proinsulin).

In some embodiments, the protein is a growth factor, e.g., vascular endothelial growth factor (VEGF), nerve growth factor (NGF), platelet-derived growth factor (PDGF), fibroblast growth factor (FGF), epidermal growth factor (EGF), transforming growth factor (TGF), and insulin-like growth factor-I and -II (IGF-I and IGF-II).

In some embodiments, the protein is a clotting factor or a coagulation factor, e.g., a blood clotting factor or a blood coagulation factor. In some embodiments, the protein is a protein involved in coagulation, i.e., the process by which blood is converted from a liquid to solid or gel. Exemplary clotting factors and coagulation factors include Factor I (e.g., fibrinogen), Factor II (e.g., prothrombin), Factor III (e.g., tissue factor), Factor V (e.g., proaccelerin, labile factor), Factor VI, Factor VII (e.g., stable factor, proconvertin), Factor VIII (e.g., antihemophilic factor A), Factor VIIIC, Factor IX (e.g., antihemophilic factor B), Factor X (e.g., Stuart-Prower factor), Factor XI (e.g., plasma thromboplastin antecedent), Factor XII (e.g., Hagerman factor), Factor XIII (e.g., fibrin-stabilizing factor), von Willebrand factor, prekallikrein, heparin cofactor II, high molecular weight kininogen (e.g., Fitzgerald factor), antithrombin III, and fibronectin. In some embodiments, the protein is an anti-clotting factor, such as Protein C.

In some embodiments, the protein is an antibody molecule. As used herein, the term "antibody molecule" refers to a protein, e.g., an immunoglobulin chain or fragment thereof, comprising at least one immunoglobulin variable domain sequence. The term "antibody molecule" includes, for example, a monoclonal antibody (including a full length antibody which has an immunoglobulin Fc region). In an embodiment, an antibody molecule comprises a full-length antibody, or a full-length immunoglobulin chain. In an embodiment, an antibody molecule comprises an antigen binding or functional fragment of a full-length antibody, or a full-length immunoglobulin chain. In an embodiment, an antibody molecule is a monospecific antibody molecule and binds a single epitope, e.g., a monospecific antibody molecule having a plurality of immunoglobulin variable domain sequences, each of which binds the same epitope. In an embodiment, an antibody molecule is a multispecific antibody molecule, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes are on the same antigen, e.g., the same protein (or subunit of a multimeric protein). In an embodiment, a multispecific antibody molecule comprises a third, fourth or fifth immunoglobulin variable domain. In an embodiment, a multispecific antibody molecule is a bispecific antibody molecule, a trispecific antibody molecule, or tetraspecific antibody molecule.

Various types of antibody molecules may be produced by the MSFCs described herein, including whole immunoglobulins of any class, fragments thereof, and synthetic proteins containing at least the antigen binding variable domain of an antibody. The antibody molecule can be an antibody, e.g., an IgG antibody, such as $IgG_1$, $IgG_2$, $IgG_3$, or $IgG_4$. An antibody molecule can be in the form of an antigen binding fragment including a Fab fragment, F(ab')2 fragment, a single chain variable region, and the like. Antibodies can be polyclonal or monoclonal (mAb). Monoclonal antibodies may include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity. In some embodiments, the antibody molecule is a single-domain antibody (e.g., a nanobody). The described antibodies can also be modified by recombinant means, for example by deletions, additions or substitutions of amino acids, to increase efficacy of the antibody in mediating the desired function. Exemplary antibodies include anti-beta-galactosidase, anti-collagen, anti-CD14, anti-CD20, anti-CD40, anti-HER2, anti-IL-1, anti-IL-4, anti-IL6, anti-IL-13, anti-IL17, anti-IL18, anti-IL-23, anti-IL-28, anti-IL-29, anti-IL-33, anti-EGFR, anti-VEGF, anti-CDF, anti-flagellin, anti-IFN-α, anti-IFN-β, anti-IFN-γ, anti-mannose receptor, anti-VEGF, anti-TLR1, anti-TLR2, anti-TLR3, anti-TLR4, anti-TLR5, anti-TLR6, anti-TLR9, anti-PDF, anti-PD1, anti-PDL-1, or anti-nerve growth factor antibody. In some embodiments, the antibody is an anti-nerve growth factor antibody (e.g., fulranumab, fasinumab, tanezumab).

In some embodiments, the protein is a cytokine or a cytokine receptor, or a chimeric protein including cytokines or their receptors, including, for example tumor necrosis factor alpha and beta, their receptors and their derivatives, renin; lipoproteins; colchicine; corticotrophin; vasopressin; somatostatin; lypressin; pancreozymin; leuprolide; alpha-1-antitrypsin; atrial natriuretic factor; lung surfactant; a plasminogen activator other than a tissue-type plasminogen activator (t-PA), for example a urokinase; bombesin; thrombin; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; chorionic gonadotropin; a microbial protein, such as beta-lactamase; DNase; inhibin; activin; receptors for hormones or growth factors; integrin; protein A or D; rheumatoid factors; platelet-derived growth factor (PDGF); epidermal growth factor (EGF); transforming growth factor (TGF) such as TGF-α and TGF-β including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; an interferon such as interferon-alpha (e.g., interferon.alpha.2A), -beta, -gamma, -lambda and consensus interferon; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; transport proteins; homing receptors; addressins; fertility inhibitors such as the prostaglandins; fertility promoters; regulatory proteins; antibodies (including fragments thereof) and chimeric proteins, such as immunoadhesins; precursors, derivatives, prodrugs and analogues of these compounds, and pharmaceutically acceptable salts of these compounds, or their precursors, derivatives, prodrugs and analogues. Suitable proteins or peptides may be native or recombinant and include, e.g., fusion proteins.

Examples of a polypeptide (e.g., a protein) produced by an MSFC described herein also include CCL1, CCL2 (MCP-1), CCL3 (MIP-1α), CCL4 (MIP-1β), CCL5 (RANTES), CCL6, CCL7, CCL8, CCL9 (CCL10), CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1 (KC), CXCL2 (SDF1a), CXCL3, CXCL4, CXCL5, CXCL6, CXCL7, CXCL8 (IL8), CXCL9, CXCL10, CXCL11, CXCL12, CXCL13, CXCL14, CXCL15, CXCL16, CXCL17, CX3CL1, XCL1, XCL2, TNFA, TNFB (LTA), TNFC (LTB), TNFSF4, TNFSF5 (CD40LG), TNFSF6, TNFSF7, TNFSF8, TNFSF9, TNFSF10, TNFSF11, TNFSF13B, EDA, IL2, IL15, IL4, IL13, IL7, IL9, IL21, IL3, IL5, IL6, IL11, IL27, IL30, IL31, OSM, LIF, CNTF, CTF1, IL12a, IL12b, IL23, IL27, IL35, IL14, IL16, IL32, IL34, IL10, IL22, IL19, IL20, IL24, IL26, IL29, IFNL1, IFNL2, IFNL3, IL28, IFNA1, IFNA2, IFNA4, IFNA5, IFNA6, IFNA7, IFNA8, IFNA10, IFNA13, IFNA14, IFNA16, IFNA17, IFNA21, IFNB1, IFNK, IFNW1, IFNG, IL1A (IL1F1), IL1B (IL1F2), IL1Ra (IL1F3), IL1F5 (IL36RN), IL1F6 (IL36A), IL1F7 (IL37), IL1F8 (IL36B), IL1F9 (IL36G), IL1F10 (IL38), IL33 (IL1F11), IL18 (IL1G), IL17, KITLG, IL25 (IL17E), CSF1 (M-CSF), CSF2 (GM-CSF), CSF3 (G-CSF), SPP1, TGFB1, TGFB2, TGFB3, CCL3L1, CCL3L2, CCL3L3, CCL4L1, CCL4L2, IL17B, IL17C, IL17D, IL17F, AIMP1 (SCYE1), MIF, Areg, BC096441, Bmp1, Bmp10, Bmp15, Bmp2, Bmp3, Bmp4, Bmp5, Bmp6, Bmp7, Bmp8a, Bmp8b, Clqtnf4, Cc121a, Cc127a, Cd70, Cerl, Cklf, Clcfl, Cmtm2a, Cmtm2b, Cmtm3, Cmtm4, Cmtm5, Cmtm6, Cmtm7, Cmtm8, Crlf1, Ctf2, Ebi3, Edn1, Fam3b, Fas1, Fgf2, Flt31, Gdf10, Gdf11, Gdf15, Gdf2, Gdf3, Gdf5, Gdf6, Gdf7, Gdf9, Gm12597, Gm13271, Gm13275, Gm13276, Gm13280, Gm13283, Gm2564, Gpil, Greml, Grem2, Grn, Hmgb1, Ifna11, Ifna12, Ifna9, Ifnab, Ifne, I117a, Il123a, I125, I131, Iltifb, Inhba, Lefty1, Lefty2, Mstn, Nampt, Ndp, Nodal, Pf4, Pglyrp1, Prl7d1, Scg2, Scgb3a1, Slurp1, Spp1, Thpo, Tnfsf10, Tnfsf11, Tnfsf12, Tnfsf13, Tnfsf13b, Tnfsf14, Tnfsf15, Tnfsf18, Tnfsf4, Tnfsf8, Tnfsf9, Tslp, Vegfa, Wnt1, Wnt2, Wnt5a, Wnt7a, Xcl1, epinephrine, melatonin, triiodothyronine, a prostaglandin, a leukotriene, prostacyclin, thromboxane, islet amyloid polypeptide, müllerian inhibiting factor or hormone, adiponectin, corticotropin, angiotensin, vasopressin, arginine vasopressin, atriopeptin, brain natriuretic peptide, calcitonin, cholecystokinin, cortistatin, enkephalin, endothelin, erythropoietin, follicle-stimulating hormone, galanin, gastric inhibitory polypeptide, gastrin, ghrelin, glucagon, glucagon-like peptide-1, gonadotropin-releasing hormone, hepcidin, human chorionic gonadotropin, human placental lactogen, inhibin, somatomedin, leptin, lipotropin, melanocyte stimulating hormone, motilin, orexin, oxytocin, pancreatic polypeptide, pituitary adenylate cyclase-activating peptide, relaxin, renin, secretin, somatostatin, thrombopoietin, thyrotropin, thyrotropin-releasing hormone, vasoactive intestinal peptide, androgen, alpha-glucosidase (also known as acid maltase), glycogen phosphorylase, glycogen debrancher enzyme, phosphofructokinase, phosphoglycerate kinase, phosphoglycerate mutase, lactate dehydrogenase, carnitine palymityl transferase, carnitine, and myoadenylate deaminase.

In some embodiments, the protein is a replacement therapy or a replacement protein. In some embodiments, the replacement therapy or replacement protein is a clotting factor or a coagulation factor, e.g., Factor VIII (e.g., comprises a naturally occurring human Factor VIII amino acid sequence or a variant thereof) or Factor IX (e.g., comprises a naturally occurring human Factor IX amino acid sequence or a variant thereof).

In some embodiments, the cell is engineered to express a Factor VIII, e.g., a recombinant Factor VIII. In some embodiments, the MSFC is derived from human tissue and is engineered to express a Factor VIII, e.g., a recombinant Factor VIII. In some embodiments, the recombinant Factor VIII is a B-domain-deleted recombinant Factor VIII (FVIII-BDD).

In some embodiments, the cell is derived from human tissue and is engineered to express a Factor IX, e.g., a recombinant Factor IX. In some embodiments, the MSFC is engineered to express a Factor IX, e.g., a wild-type human Factor IX (FIX), or a polymorphic variant thereof. In some embodiments, the cell is engineered to express a gain-in-function (GIF) variant of a wild-type FIX protein (FIX-GIF), wherein the GIF variant has higher specific activity than the corresponding wild-type FIX.

In some embodiments, the replacement therapy or replacement protein is an enzyme, e.g., alpha-galactosidase, alpha-L-iduronidase (IDUA), or N-sulfoglucosamine sulfohydrolase (SGSH). In some embodiments, the replacement therapy or replacement protein is an enzyme, e.g., an alpha-galactosidase A (e.g., comprises a naturally-occurring human alpha-galactosidase A amino acid sequence or a variant thereof). In some embodiments, the replacement therapy or replacement protein is a cytokine or an antibody.

In some embodiments, the therapeutic agent is a sugar, e.g., monosaccharide, disaccharide, oligosaccharide, or polysaccharide. In some embodiments, a sugar comprises a triose, tetrose, pentose, hexose, or heptose moiety. In some embodiments, the sugar comprises a a linear monosaccharide or a cyclized monosaccharide. In some embodiments, the sugar comprises a glucose, galactose, fructose, rhamnose, mannose, arabinose, glucosamine, galactosamine, sialic acid, mannosamine, glucuronic acid, galactosuronic acid, mannuronic acid, or guluronic acid moiety. In some embodiments, the sugar is attached to a protein (e.g., an N-linked glycan or an O-linked glycan). Exemplary sugars include glucose, galactose, fructose, mannose, rhamnose, sucrose, ribose, xylose, sialic acid, maltose, amylose, inulin, a fructooligosaccharide, galactooligosaccharide, a mannan, a lectin, a pectin, a starch, cellulose, heparin, hyaluronic acid, chitin, amylopectin, or glycogen. In some embodiments, the therapeutic agent is a sugar alcohol.

In some embodiments, the therapeutic agent is a lipid. A lipid may be hydrophobic or amphiphilic, and may form a tertiary structure such as a liposome, vesicle, or membrane or insert into a liposome, vesicle, or membrane. A lipid may comprise a fatty acid, glycerolipid, glycerophospholipid, sterol lipid, prenol lipid, sphingolipid, saccharolipid, polyketide, or sphingolipid. Examples of lipids produced by the MSFCs described herein include anandamide, docosahexaenoic acid, aprostaglandin, a leukotriene, a thromboxane, an eicosanoid, a triglyceride, a cannabinoid, phosphatidylcholine, phosphatidylethanolamine, a phosphatidylinositol, a phosohatidic acid, a ceramide, a sphingomyelin, a cerebroside, a ganglioside, estrogen, androsterone, testosterone, cholesterol, a carotenoid, a quinone, a hydroquinone, or a ubiquinone.

In some embodiments, the therapeutic agent is a small molecule. A small molecule may include a natural product produced by a cell. In some embodiments, the small molecule has poor availability or does not comply with the Lipinski rule of five (a set of guidelines used to estimate whether a small molecule will likely be an orally active drug in a human; see, e.g., Lipinski, C. A. et al (2001) *Adv Drug Deliv* 46:2-36). Exemplary small molecule natural products include an anti-bacterial drug (e.g., carumonam, daptomycin, fidaxomicin, fosfomycin, ispamicin, micronomicin sulfate, miocamycin, mupiocin, netilmicin sulfate, teicoplanin, thienamycin, rifamycin, erythromycin, vancomycin), an anti-parasitic drug (e.g., artemisinin, ivermectin), an anti-cancer drug (e.g., doxorubicin, aclarubicin, aminolaevulinic acid, arglabin, omacetaxine mepesuccinate, paclitaxel, pentostatin, peplomycin, romidepsin, trabectdin, actinomycin D, bleomycin, chromomycin A, daunorubicin, leucovorin, neocarzinostatin, streptozocin, trabectedin, vinblastine, vincristine), anti-diabetic drug (e.g., voglibose), a central nervous system drug (e.g., L-dopa, galantamine, zicontide), a statin (e.g., mevastatin), an anti-fungal drug (e.g., fumagillin, cyclosporin), 1-deoxynojirimycin, and theophylline, sterols (cholesterol, estrogen, testosterone). Additional small molecule natural products are described in Newman, D. J. and Cragg, M. (2016) *J Nat Prod* 79:629-661 and Butler, M. S. et al (2014) *Nat Prod Rep* 31:1612-1661, which are incorporated herein by reference in their entirety.

In some embodiments, the cell is engineered to synthesize a non-protein or non-peptide small molecule. For example, in an embodiment an cell can produce a statin (e.g., taurostatin, pravastatin, fluvastatin, or atorvastatin).

In some embodiments, the therapeutic agent is an antigen (e.g., a viral antigen, a bacterial antigen, a fungal antigen, a plant antigen, an environmental antigen, or a tumor antigen). An antigen is recognized by those skilled in the art as being immunostimulatory, i.e., capable of stimulating an immune response or providing effective immunity to the organism or molecule from which it derives. An antigen may be a nucleic acid, peptide, protein, sugar, lipid, or a combination thereof.

The cells, e.g., engineered cells, e.g., engineered cells described herein, may produce a single therapeutic agent or a plurality of therapeutic agents. In some embodiments, the cells produce a single therapeutic agent. In some embodiments, a cluster of cells comprises cells that produce a single therapeutic agent. In some embodiments, at least about 1%, 5%, 10%, 20%, 25%, 30%, 40%, 50%, 60%, 70%, 80%, 90%, 95%, or 99% of the cells in a cluster produce a single therapeutic agent (e.g., a therapeutic agent described herein). In some embodiments, the MSFCs produce a plurality of therapeutic agents, e.g., at least 2, 3, 4, 5, 6, 7, 8, 9, or 10 therapeutic agents. In some embodiments, a cluster of cells comprises cells that produce a plurality of therapeutic agents. In some embodiments, at least about 1%, 5%, 10%, 20%, 25%, 30%, 40%, 50%, 60%, 70%, 80%, 90%, 95%, or 99% of the cells in a cluster produce a plurality of therapeutic agents (e.g., a therapeutic agent described herein).

The therapeutic agents may be related or may form a complex. In some embodiments, the therapeutic agent secreted or released from a cell in an active form. In some embodiments, the therapeutic agent is secreted or released from an cell in an inactive form, e.g., as a prodrug. In the latter instance, the therapeutic agent may be activated by a downstream agent, such as an enzyme. In some embodiments, the therapeutic agent is not secreted or released from a cell, but is maintained intracellularly. For example, the therapeutic agent may be an enzyme involved in detoxification or metabolism of an unwanted substance, and the detoxification or metabolism of the unwanted substance occurs intracellularly.

Methods of Treatment

Described herein are methods for preventing or treating a disease, disorder, or condition in a subject through administration or implantation of an implantable element or polymer comprising a compound of Formula (II) or a pharmaceutically acceptable salt thereof. In some embodiments, the methods described herein directly or indirectly reduce or alleviate at least one symptom of a disease, disorder, or condition. In some embodiments, the methods described herein prevent or slow the onset of a disease, disorder, or condition. In some embodiments, the subject is a human.

In some embodiments, the disease, disorder, or condition affects a system of the body, e.g. the nervous system (e.g., peripheral nervous system (PNS) or central nervous system (CNS)), vascular system, skeletal system, respiratory system, endocrine system, lymph system, reproductive system, or gastrointestinal tract. In some embodiments, the disease, disorder, or condition affects a part of the body, e.g., blood, eye, brain, skin, lung, stomach, mouth, ear, leg, foot, hand, liver, heart, kidney, bone, pancreas, spleen, large intestine, small intestine, spinal cord, muscle, ovary, uterus, vagina, or penis.

In some embodiments, the disease, disorder or condition is a neurodegenerative disease, diabetes, a heart disease, an autoimmune disease, a cancer, a liver disease, a lysosomal storage disease, a blood clotting disorder or a coagulation disorder, an orthopedic conditions, an amino acid metabolism disorder.

In some embodiments, the disease, disorder or condition is a neurodegenerative disease. Exemplary neurodegenerative diseases include Alzheimer's disease, Huntington's disease, Parkinson's disease (PD) amyotrophic lateral sclerosis (ALS), multiple sclerosis (MS) and cerebral palsy (CP), dentatorubro-pallidoluysian atrophy (DRPLA), neuronal intranuclear hyaline inclusion disease (NIHID), dementia with Lewy bodies, Down's syndrome, Hallervorden-Spatz disease, prion diseases, argyrophilic grain dementia, cortocobasal degeneration, dementia pugilistica, diffuse neurofibrillary tangles, Gerstmann-Straussler-Scheinker disease, Jakob-Creutzfeldt disease, Niemann-Pick disease type 3, progressive supranuclear palsy, subacute sclerosing panencephalitis, spinocerebellar ataxias, Pick's disease, and dentatorubral-pallidoluysian atrophy.

In some embodiments, the disease, disorder, or condition is an autoimmune disease, e.g., scleroderma, multiple sclerosis, lupus, or allergies.

In some embodiments, the disease is a liver disease, e.g., hepatitis B, hepatitis C, cirrhosis, NASH.

In some embodiments, the disease, disorder, or condition is cancer. Exemplary cancers include leukemia, lymphoma, melanoma, lung cancer, brain cancer (e.g., glioblastoma), sarcoma, pancreatic cancer, renal cancer, liver cancer, testicular cancer, prostate cancer, or uterine cancer.

In some embodiments, the disease, disorder, or condition is an orthopedic condition. Exemplary orthopedic conditions include osteoporosis, osteonecrosis, Paget's disease, or a fracture.

In some embodiments, the disease, disorder or condition is a lysosomal storage disease. Exemplary lysosomal storage diseases include Gaucher disease (e.g., Type I, Type II, Type III), Tay-Sachs disease, Fabry disease, Farber disease, Hurler syndrome (also known as mucopolysaccharidosis type I (MPS I)), Hunter syndrome, lysosomal acid lipase deficiency, Niemann-Pick disease, Salla disease, Sanfilippo syndrome (also known as mucopolysaccharidosis type IIIA (MPS3A)), multiple sulfatase deficiency, Maroteaux-Lamy syndrome, metachromatic leukodystrophy, Krabbe disease, Scheie syndrome, Hurler-Scheie syndrome, Sly syndrome, hyaluronidase deficiency, Pompe disease, Danon disease, gangliosidosis, or Morquio syndrome.

In some embodiments, the disease, disorder, or condition is a blood clotting disorder or a coagulation disorder. Exemplary blood clotting disorders or coagulation disorders include hemophilia (e.g., hemophilia A or hemophilia B), Von Willebrand disease, thrombocytopenia, uremia, Bernard-Soulier syndrome, Factor XII deficiency, vitamin K deficiency, or congenital afibrinogenimia.

In some embodiments, the disease, disorder, or condition is an amino acid metabolism disorder, e.g., phenylketonuria, tyrosinemia (e.g., Type 1 or Type 2), alkaptonuria, homocystinuria, hyperhomocysteinemia, maple syrup urine disease.

In some embodiments, the disease, disorder, or condition is a fatty acid metabolism disorder, e.g., hyperlipidemia, hypercholesterolemia, galactosemia.

In some embodiments, the disease, disorder, or condition is a purine or pyrimidine metabolism disorder, e.g., Lesch-Nyhan syndrome.

In some embodiments, the disease, disorder, or condition is not diabetes (e.g., Type I or Type II diabetes).

The present invention further comprises methods for identifying a subject having or suspected of having a disease, disorder, or condition described herein, and upon such identification, administering to the subject implantable element comprising a cell, e.g., optionally encapsulated by an enclosing component, and optionally modified with a compound of Formula (II) as described herein, or a composition thereof. In an embodiment, the subject is a human.

EXAMPLES

In order that the invention described herein may be more fully understood, the following examples are set forth. The synthetic and biological examples described in this application are offered to illustrate the compounds, compositions, devices, and methods provided herein and are not to be construed in any way as limiting their scope.

The compounds, polymers, implantable elements, and compositions thereof provided herein can be prepared from readily available starting materials using modifications to the specific synthesis protocols set forth below that would be well known to those of skill in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

Exemplary compounds, polymers, implantable elements, and compositions of the invention may be prepared using any of the strategies described below.

Example 1: Synthesis of Exemplary Compounds

General Protocols

The procedures below describe methods of preparing exemplary compounds for preparation of chemically modified implantable elements. The compounds provided herein can be prepared from readily available starting materials using modifications to the specific synthesis protocols set forth below that would be well known to those of skill in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

Huisgen Cycloaddition to Afford 1,4-Substituted Triazoles

The copper-catalyzed Huisgen [3+2] cycloaddition was used to prepare triazole-based compounds and compositions, devices, and materials thereof. The scope and typical protocols have been the subject of many reviews (e.g., Meldal, M. and Tornoe, C. W. *Chem. Rev.* (2008) 108:2952-3015; Hein, J. E. and Fokin, V. V. *Chem. Soc. Rev.* (2010) 39(4):1302-1315; both of which are incorporated herein by reference).

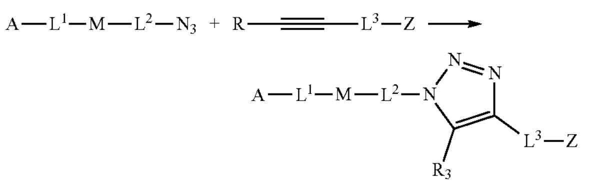

In the example shown above, the azide is the reactive moiety in the fragment containing the connective element A, while the alkyne is the reactive component of the pendant group Z. As depicted below, these functional handles can be exchanged to produce a structurally related triazole product. The preparation of these alternatives is similar, and do not require special considerations.

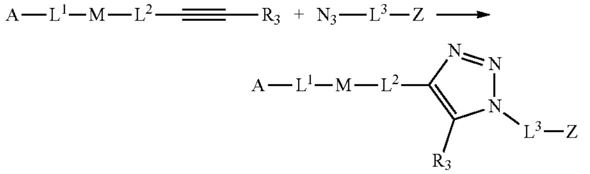

A typical Huisgen cycloaddition procedure starting with an iodide is outlined below. In some instances, iodides are transformed into azides during the course of the reaction for safety.

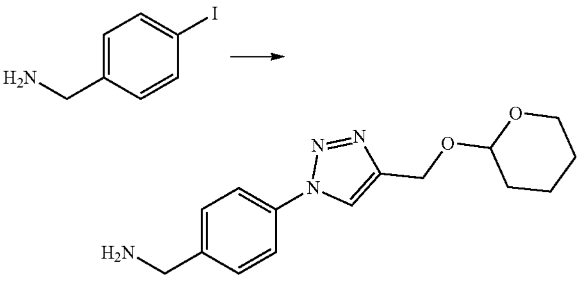

A solution of sodium azide (1.1 eq), sodium ascorbate, (0.1 eq) trans-N,N'-dimethylcyclohexane-1,2-diamine (0.25 eq), copper (I) iodide in methanol (1.0 M, limiting reagent) was degassed with bubbling nitrogen and treated with the acetylene (1 eq) and the aryl iodide (1.2 eq). This mixture was stirred at room temperature for 5 minutes, then warmed to 55° C. for 16 h. The reaction was then cooled to room temperature, filtered through a funnel, and the filter cake washed with methanol. The combined filtrates were concentrated and purified via flash chromatography on silica gel (120 g silica, gradient of 0 to 40% (3% aqueous ammonium hydroxide, 22% methanol, remainder dichloromethane) in dichloromethane to afford the desired target material.

A typical Huisgen cycloaddition procedure starting with an azide is outlined below.

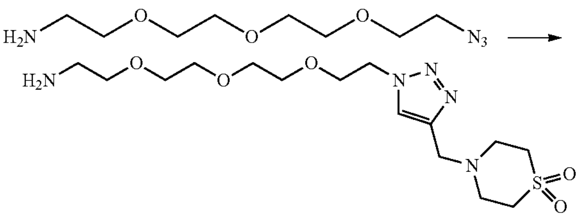

A solution of tris[(1-benzyl-1H-1,2,3-triazol-4-yl)methyl]amine (0.2 eq), triethylamine (0.5 eq), copper (I) iodide (0.06 eq) in methanol (0.4 M, limiting reagent) was treated with the acetylene (1.0 eq) and cooled to 0° C. The reaction was allowed to warm to room temperature over 30 minutes, then heated to 55° C. for 16 h. The reaction was cooled to room temperature, concentrated, and purified with HPLC (C18 column, gradient of 0 to 100% (3% aqueous ammonium hydroxide, 22% methanol remainder dichloromethane) in dichloromethane to afford the desired target material.

Huisgen Cycloaddition to Afford 1,5-Substituted Triazoles

The Huisgen [3+2] cycloaddition was also performed with ruthenium catalysts to obtain 1,5-disubstituted products preferentially (e.g., as described in Zhang et al, *J. Am. Chem. Soc.,* 2005, 127, 15998-15999; Boren et al, *J. Am. Chem. Soc.,* 2008, 130, 8923-8930, each of which is incorporated herein by reference in its entirety).

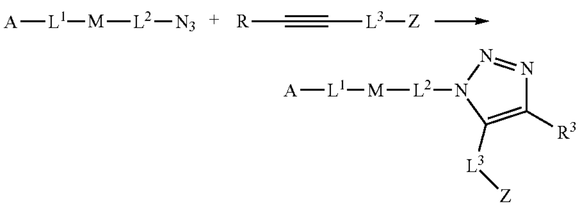

As described previously, the azide and alkyne groups may be exchanged to form similar triazoles as depicted below.

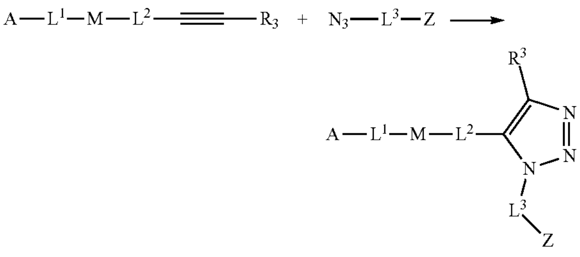

A typical procedure is described as follows: a solution of the alkyne (1 eq) and the azide (1 eq) in dioxane (0.8M) were added dropwise to a solution of pentamethylcyclo-pentadienylbis(triphenylphosphine) ruthenium(II) chloride (0.02 eq) in dioxane (0.16M). The vial was purged with nitrogen, sealed and the mixture heated to 60° C. for 12 h. The resulting mixture was concentrated and purified via flash chromatography on silica gel to afford the requisite compound.

Experimental Procedure for (4-(4-((4-methylpiperazin-1-yl)methyl)-1H-1,2,3-triazol-1-yl)phenyl) methanamine (3)

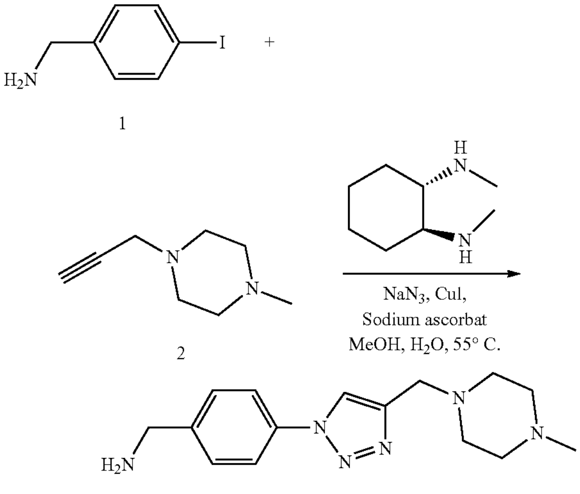

1

2

3

A mixture of (4-iodophenyl)methanamine (1, 843 mg, 3.62 mmol, 1.0 eq), (1S,2S)—N1,N2-dimethylcyclohexane-1,2-diamine (74 μL, 0.47 mmol, 0.13 eq), Sodium ascorbate (72 mg, 0.36 mmol, 0.1 eq), Copper Iodide (69 mg, 0.36 mmol, 0.1 eq), Sodium azide (470 mg, 7.24 mmol, 2.0 eq), and 1-methyl-4-(prop-2-yn-1-yl)piperazine (2, 0.5 g, 3.62 mmol, 1.0 eq) in Methanol (9 mL) and water (1 mL) were purged with nitrogen for 5 minutes and heated to 55° C. for over night. The reaction mixture was cooled to room temperature, concentrated under reduced pressure, and the brownish slurry was extracted with dichloromethane. Celite was added to the combined dichloromethane phases and the solvent was removed under reduced pressure. The crude product was purified over silica gel (80 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 7.5% to afford (4-(4-((4-methylpiperazin-1-yl)methyl)-1H-1,2,3-triazol-1-yl)phenyl)methanamine (3, 0.45 g, 43%). LCMS m/z: $[M+H]^+$ Calcd for $C_{15}H_{22}N_6$ 287.2; Found 287.1.

Experimental Procedure for N-(4-(4-((4-methylpiperazin-1-yl)methyl)-1H-1,2,3-triazol-1-yl)benzyl) methacrylamide (4)

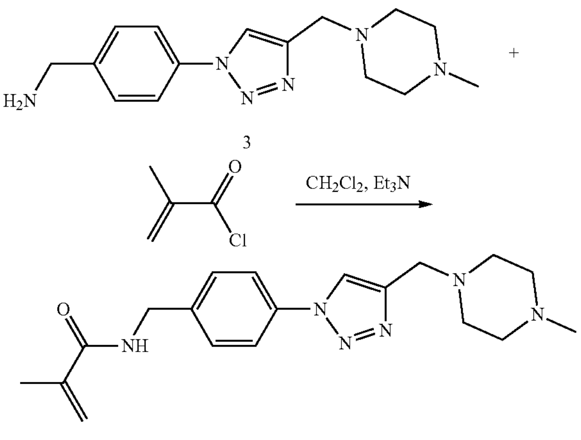

3

4

A solution of (4-(4-((4-methylpiperazin-1-yl)methyl)-1H-1,2,3-triazol-1-yl)phenyl)methanamine (3, 1.2 g, 4.19 mmol, 1.0 eq) and triethylamine (0.70 mL, 5.03 mmol, 1.2 eq) in $CH_2Cl_2$ (50 mL) was cooled to 0° C. with an ice-bath and methacryloyl chloride (0.43 mL, 4.40 mmol, 1.05 eq in 5 mL of $CH_2Cl_2$) was added. The reaction was stirred for a day while cooled with an ice-bath. 10 grams of Celite were added and the solvent was removed under reduced pressure. The residue was purified by silica gel chromatography (80 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 7.5%. The solvent was removed under reduced pressure and the resulting solid was triturated with diethyl ether, filtered and washed multiple times with diethyl ether to afford N-(4-(4-((4-methylpiperazin-1-yl)methyl)-1H-1,2,3-triazol-1-yl)benzyl)methacrylamide (4, 0.41 g, 28% yield) as a white solid. LCMS m/z: $[M+H]^+$ Calcd for $C_{19}H_{26}N_6O$ 355.2; Found 355.2.

Experimental Procedure for (4-(4-((2-(2-methoxyethoxy)ethoxy)methyl)-1H-1,2,3-triazol-1-yl)phenyl) methanamine (6)

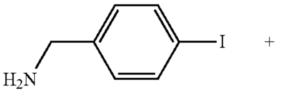

1

-continued

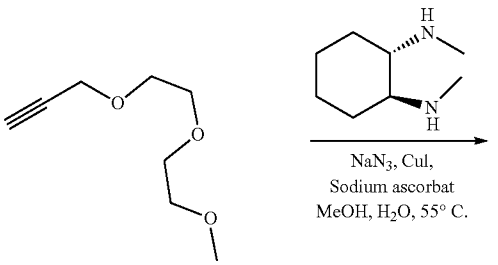

5

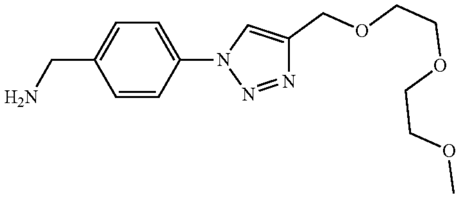

6

A mixture of (4-iodophenyl)methanamine (1, 2.95 g, 12.64 mmol, 1.0 eq), (1S,2S)—N1,N2-dimethylcyclohexane-1,2-diamine (259 μL, 1.64 mmol, 0.13 eq), Sodium ascorbate (250 mg, 1.26 mmol, 0.1 eq), Copper Iodide (241 mg, 1.26 mmol, 0.1 eq), Sodium azide (1.64 g, 25.29 mmol, 2.0 eq), and 1-methyl-4-(prop-2-yn-1-yl)piperazine (5, 2.0 g, 12.64 mmol, 1.0 eq) in Methanol (40 mL) and water (4 mL) were purged with Nitrogen for 5 minutes and heated to 55° C. overnight. The reaction mixture was cooled to room temperature and concentrated under reduced pressure. The residue was dissolved in dichloromethane, filtered, and concentrated with Celite (10 g). The crude product was purified by silica gel chromatography (220 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 6.25% to afford (4-(4-((2-(2-methoxyethoxy)ethoxy)methyl)-1H-1,2,3-triazol-1-yl)phenyl)methanamine (6, 1.37 g, 35%). LCMS m/z: $[M+H]^+$ Calcd for $C_{15}H_{22}N_4O_3$307.2; Found 307.0.

Experimental Procedure for N-(4-(4-((2-(2-methoxyethoxy)ethoxy)methyl)-1H-1,2,3-triazol-1-yl)benzyl)methacrylamide (7)

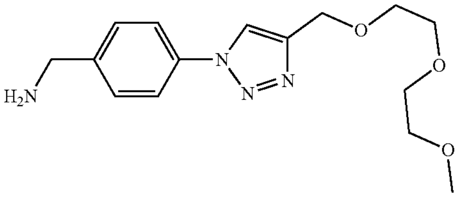

+

6

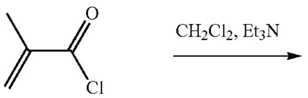

-continued

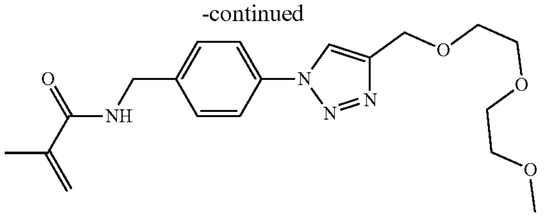

7

A solution of 4-(4-(2-(2-methoxyethoxy)ethoxy)methyl)-1H-1,2,3-triazol-1-yl)phenyl)methanamine (6, 1.69 g, 5.52 mmol, 1.0 eq) and triethylamine (0.92 mL, 6.62 mmol, 1.2 eq) in $CH_2Cl_2$(50 mL) was cooled to 0° C. with an ice-bath and methacryloyl chloride (0.57 mL, 5.79 mmol, 1.05 eq) was added in a dropwise fashion. The reaction was stirred for 4 h at room temperature. 10 grams of Celite were added and the solvent was removed under reduced pressure. The residue was purified by silica gel (80 g) chromatography using dichloromethane/(methanol containing 12% (v/v) aqueous ammonium hydroxide) as mobile phase. The concentration of (methanol containing 12% (v/v) aqueous ammonium hydroxide) was gradually increased from 0% to 1.25% to afford N-(4-(4-((2-(2-methoxyethoxy)ethoxy)methyl)-1H-1,2,3-triazol-1-yl)benzyl)methacrylamide (7, 1.76 g, 85% yield) as a white solid. LCMS m/z: $[M+H]^+$ Calcd for $C_{19}H_{26}N_4O_4$ 375.2; Found 375.0.

Experimental Procedure for 3-(prop-2-yn-1-yloxy)oxetane (9)

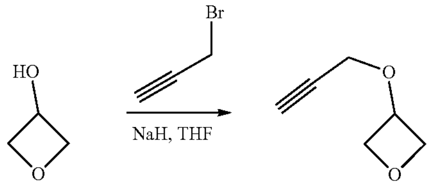

8

9

A suspension of sodium hydride (27.0 g, 675 mmol, 60% purity) in THF (200 mL) was cooled with an ice bath. Oexetan-3-ol (8, 25 g, 337 mmol) was added in a dropwise fashion and stirred for 30 minutes at 0° C. 3-Bromopropl-yne (9, 41.2 mL, 371 mmol, 80% purity) was then added in a dropwise fashion. The mixture was stirred over night while allowed to warm to room temperature. The mixture was filtered over Celite, washed with THF, and concentrated with Celite under reduced pressure. The crude product was purified over silica gel (220 g) and eluted with Hexanes/EtOAc. The concentration of EtOAc in the mobile phase was increased from 0 to 25% to afford a yellow oil of (9, 18.25 g 48%).

Experimental Procedure for 3-(4-((oxetan-3-yloxy)methyl)-1H-1,2,3-triazol-1-yl)propan-1-amine (11)

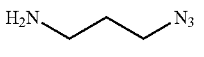

+

10

-continued

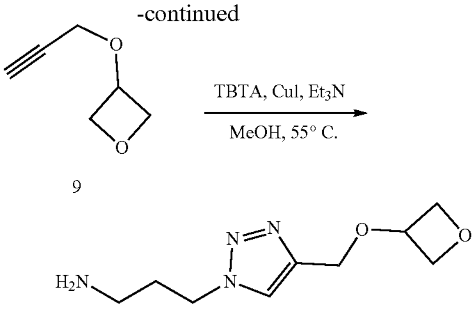

9

11

A mixture of 3-(prop-2-yn-1-yloxy)oxetane (9, 7.96 g, 71 mmol, 1.0 eq), 3-azidopropan-1-amine (10, 7.82 g, 78 mmol, 1.1 eq), Tris[(1-benzyl-1H-1,2,3-triazol-4-yl) methyl]-amine (8.29 g, 15.6 mmol, 0.22 eq), Copper Iodide (1.35 g, 7.1 mmol, 0.1 eq), and Triethylamine (2.47 mL, 17.8 mmol, 0.25 eq) in Methanol (80 mL) was warmed to 55° C. and stirred over night under Nitrogen atmosphere. The reaction mixture was cooled to room temperature, Celite (20 g) was added, and concentrated under reduced pressure. The crude product was purified over silica gel (220 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 15% to afford 3-(4-((oxetan-3-yloxy)methyl)-1H-1,2,3-triazol-1-yl) propan-1-amine (11, 11.85 g, 79%) as a yellow oil. LCMS m/z: $[M+H]^+$ Calcd for $C_9H_{16}N_4O_2$ 213.1; Found 213.0.

Experimental Procedure for N-(3-(4-((oxetan-3-yloxy)methyl)-1H-1,2,3-triazol-1-yl)propyl)methacrylamide (12)

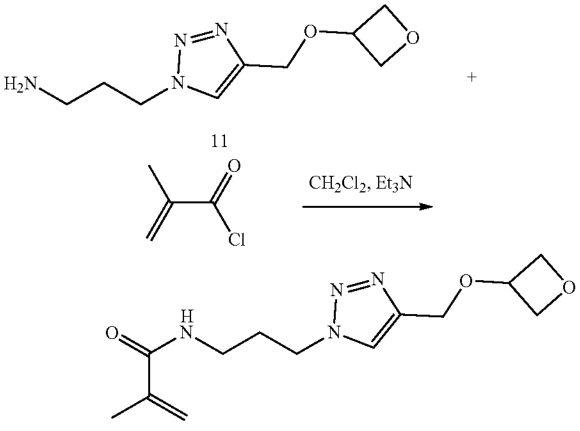

11

12

A solution of 3-(4-((oxetan-3-yloxy)methyl)-1H-1,2,3-triazol-1-yl)propan-1-amine (11, 3.94 g, 18.56 mmol, 1.0 eq) and triethylamine (3.1 mL, 22.28 mmol, 1.2 eq) in $CH_2Cl_2$ (100 mL) was cooled to 0° C. with an ice-bath and methacryloyl chloride (1.99 mL, 20.42 mmol, 1.1 eq) was added in a dropwise fashion. The reaction was stirred over night while allowed to warm to room temperature. 20 grams of Celite were added and the solvent was removed under reduced pressure. The residue was purified by silica gel chromatography (220 g) using dichloromethane/methanol as mobile phase. The concentration of methanol was gradually increased from 0% to 5% to afford N-(3-(4-((oxetan-3-yloxy)methyl)-1H-1,2,3-triazol-1-yl)propyl)methacrylamide (12, 3.22 g, 62% yield) as a solid. LCMS m/z: $[M+H]^+$ Calcd for $C_{13}H_{20}N_4O_3$ 281.2; Found 281.0.

Experimental Procedure for N-(4-(1H-1,2,3-triazol-1-yl)benzyl) methacrylamide (14)

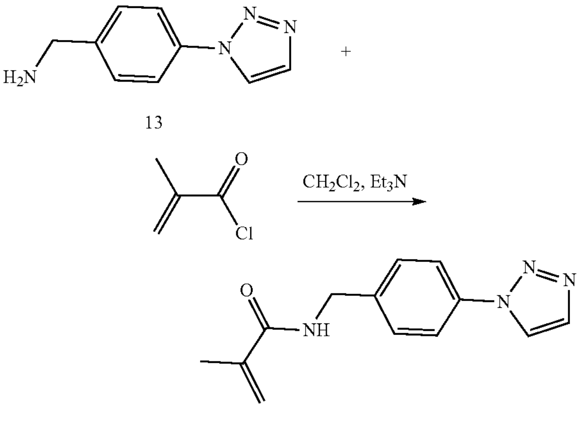

13

14

To a solution of (4-(1H-1,2,3-triazol-1-yl)phenyl)methanamine (13, obtained from WuXi, 1.2 g, 5.70 mmol, 1.0 eq) and triethylamine (15 mL, 107.55 mmol, 18.9 eq) in $CH_2Cl_2$ (100 mL) was slowly added methacryloyl chloride (893 mg, 8.54 mmol, 1.5 eq) in a dropwise fashion. The reaction was stirred over night. 20 grams of Celite were added and the solvent was removed under reduced pressure. The residue was purified by silica gel chromatography using dichloromethane/(methanol containing 12% (v/v) aqueous ammonium hydroxide) as mobile phase. The concentration of (methanol containing 12% (v/v) aqueous ammonium hydroxide) was gradually increased from 0% to 1.25% to afford N-(4-(1H-1,2,3-triazol-1-yl)benzyl) methacrylamide (14, 1.38 g, 40% yield).

Experimental Procedure for (4-(4-(((tetrahydro-2H-pyran-2-yl)oxy)methyl)-1H-1,2,3-triazol-1-yl)phenyl)methanamine (15)

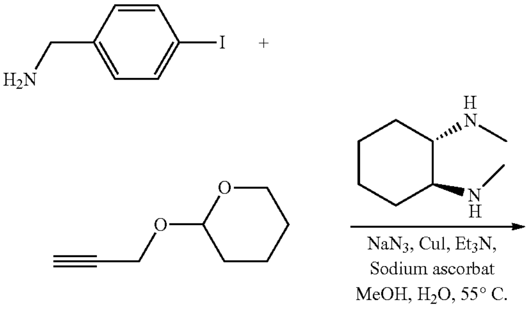

-continued

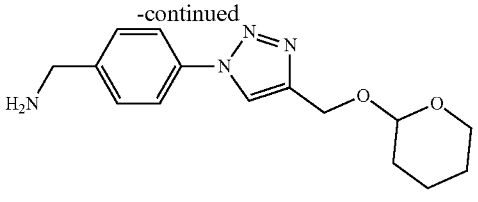

15

A mixture of (4-iodophenyl)methanamine hydrochloride (5.0 g, 18.55 mmol, 1.0 eq), (1S,2S)—N1,N2-dimethylcyclohexane-1,2-diamine (0.59 mL 3.71 mmol, 0.2 eq), Sodium ascorbate (368 mg, 1.86 mmol, 0.1 eq), Copper Iodide (530 mg, 2.78 mmol, 0.15 eq), Sodium azide (2.41 g, 37.1 mmol, 2.0 eq), $Et_3N$ (3.11 mL, 22.26 mmol, 1.2 eq) and 2-(prop-2-yn-1-yloxy)tetrahydro-2H-pyran (2.6 g, 18.55 mmol, 1.0 eq) in Methanol (50 mL) and water (12 mL) were purged with Nitrogen for 5 minutes and heated to 55° C. for over night. The reaction mixture was cooled to room temperature and filtered through 413 filter paper. Celite was added and the solvent was removed under reduced pressure and the residue was purified over silica gel (120 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 6.25% to afford (4-(4-(((tetrahydro-2H-pyran-2-yl)oxy)methyl)-1H-1,2,3-triazol-1-yl)phenyl)methanamine (15, 3.54 g, 66%) as a white solid. LCMS m/z: $[M+H]^+$ Calcd for $C_{15}H_{20}N_4O_2$ 289.2; Found 289.2.

Experimental Procedure for N-(4-(4-(((tetrahydro-2H-pyran-2-yl)oxy)methyl)-1H-1,2,3-triazol-1-yl)benzyl)methacrylamide (16)

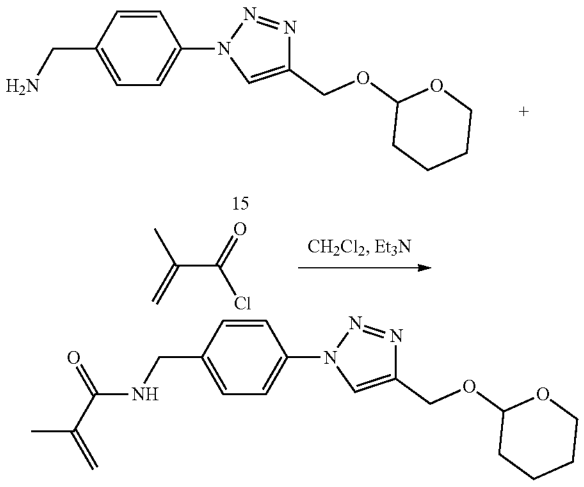

15

16

A solution of (4-(4-(((tetrahydro-2H-pyran-2-yl)oxy)methyl)-1H-1,2,3-triazol-1-yl)phenyl)methanamin (15, 3.46 g, 12.00 mmol, 1.0 eq) and triethylamine (2.01 mL, 14.40 mmol, 1.2 eq) in $CH_2Cl_2$(40 mL) was cooled to 0° C. with an ice-bath and methacryloyl chloride (1.23 mL, 12.60 mmol, 1.05 eq, diluted in 5 mL of $CH_2Cl_2$) was added in a dropwise fashion. The cooling bath was removed and the reaction was stirred for 4 h. 20 grams of Celite was added and the solvent was removed under reduced pressure. The residue was purified by silica gel chromatography (80 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 3.75% to afford N-(4-(4-(((tetrahydro-2H-pyran-2-yl)oxy)methyl)-1H-1,2,3-triazol-1-yl)benzyl)methacrylamide (16, 2.74 g, 64% yield) as a white solid. LCMS m/z: $[M+H]^+$ Calcd for $C_{19}H_{24}N_4O_3$ 357.2; Found 357.3.

Experimental Procedure for N-(4-(4-(hydroxymethyl)-1H-1,2,3-triazol-1-yl)benzyl)methacrylamide (17)

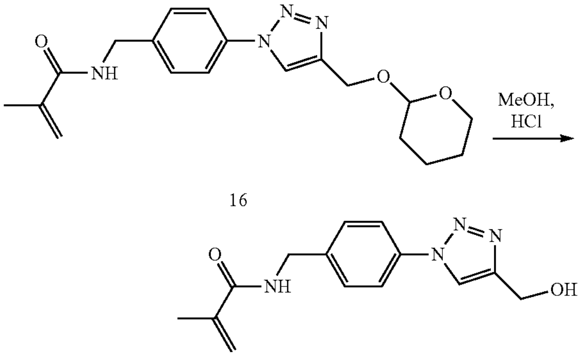

16

17

A solution of N-(4-(4-(hydroxymethyl)-1H-1,2,3-triazol-1-yl)benzyl)methacrylamide (16, 1.2 g, 3.37 mmol, 1.0 eq) was dissolved in Methanol (6 mL) and HCl (1N, aq., 9 mL) for over night at room temperature. Celite was added and the solvent was removed under reduced pressure. The crude product was purified over silica gel chromatography (24 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 12.5% to afford N-(4-(4-(hydroxymethyl)-1H-1,2,3-triazol-1-yl)benzyl)methacrylamide (17, 0.85 g, 92% yield) as a white solid. LCMS m/z: $[M+H]^+$ Calcd for $C_{14}H_{16}N_4O_2$ 273.1; Found 273.1.

Experimental Procedure for (4-(((tetrahydro-2H-pyran-2-yl)oxy)methyl)benzyl)carbamate (19)

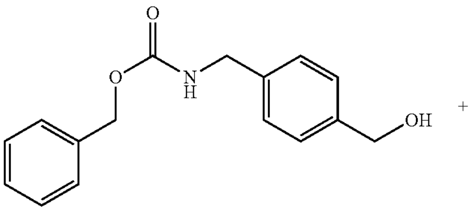

18

-continued

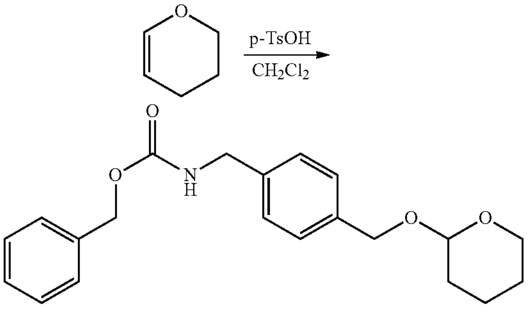

19

Benzyl (4-(hydroxymethyl)benzyl)carbamate (2.71 g, 10 mmol, 1 eq), 3,4-dihydro-2H-pyran (1.81 mL, 20 mmol, 2 eq), p-Toluenesulfonic acid monohydrate (285 mg, 1.5 mmol, 0.15 eq) in dichloromethane (100 mL) were stirred at room temperature over night. Celite was added and the solvent was removed under reduced pressure. The crude product was purified over silica gel (24 g) using Hexanes/EtOAc as eluent starting at 100% Hexanes and increasing the concentration of EtOAc gradually to 100% to afford benzyl (4-(((tetrahydro-2H-pyran-2-yl)oxy)methyl)benzyl)-carbamate (19, 2.4 g, 68%) as a colorless oil. LCMS m/z: $[M+Na]^+$ Calcd for $C_{21}H_{25}NO_4$ 378.17 Found 378.17.

Experimental Procedure for (4-(((tetrahydro-2H-pyran-2-yl)oxy)methyl)-phenyl)methanamine (20)

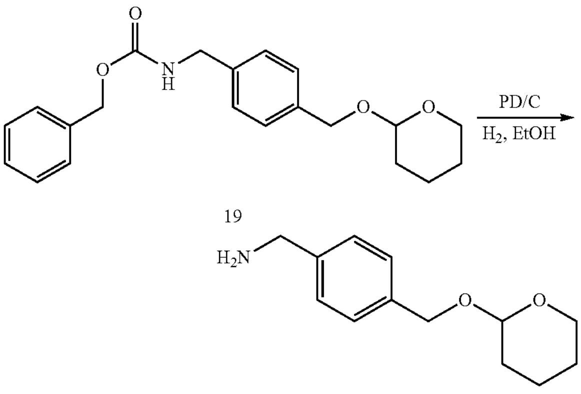

19

20

(4-(((tetrahydro-2H-pyran-2-yl)oxy)methyl)benzyl)carbamate (19, 1.5 g, 4.2 mmol, 1 eq), Palladium on carbon (160 mg, 10 wt. %) in EtOH was briefly evacuated and then Hydrogen was added via a balloon and the mixture was stirred for 1 hour at room temperature. Celite was added and the solvent was removed under reduced pressure. The crude product was purified over silica gel (12 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 25% to afford (4-(((tetrahydro-2H-pyran-2-yl)oxy)methyl)phenyl) methanamine (20, 890 mg, 95%) as a colorless oil. LCMS m/z: $[M+H]^+$ Calcd for $C_{13}H_{19}NO_2$ 222.15 Found 222.14.

Experimental Procedure for N-(4-(((tetrahydro-2H-pyran-2-yl)oxy)methyl)benzyl)-methacrylamide (21)

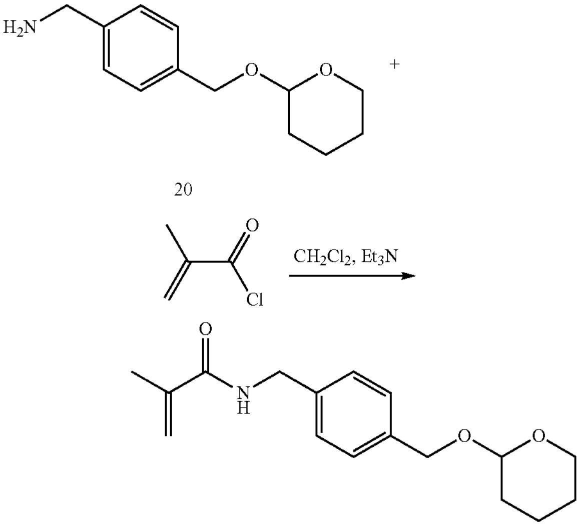

20

21

A solution of (4-(((tetrahydro-2H-pyran-2-yl)oxy)methyl) phenyl)methanamine (20, 0.5 g, 2.26 mmol, 1.0 eq) and triethylamine (0.47 mL, 3.39 mmol, 1.5 eq) in $CH_2Cl_2$(10 mL) were briefly evacuated and flushed with Nitrogen. Methacryloyl chloride (0.33 mL, 3.39 mmol, 1.5 eq) was added in a dropwise fashion. The reaction mixture was stirred over night at room temperature. 10 grams of Celite was added and the solvent was removed under reduced pressure. The residue was purified by silica gel chromatography (12 g) using Hexanes/EtOAc as eluent starting at 100% Hexanes and increasing the concentration of EtOAc gradually to 100% to afford N-(4-(((tetrahydro-2H-pyran-2-yl)oxy)methyl)benzyl)methacrylamide (21, 0.47 g, 72% yield) as a colorless solid. LCMS m/z: $[M+Na]^+$ Calcd for $C_{17}H_{23}NO_3$ 312.16; Found 312.17.

Experimental Procedure (4-(4-(2-((tetrahydro-2H-pyran-2-yl)oxy)ethyl)-1H-1,2,3-triazol-1-yl)phenyl) methanamine (22)

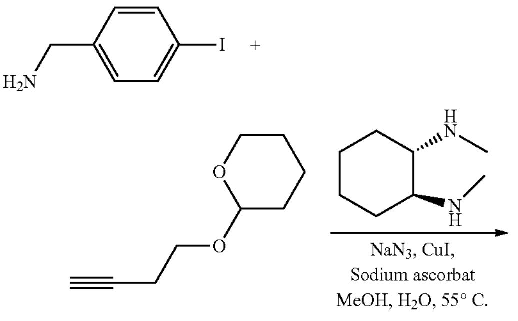

-continued

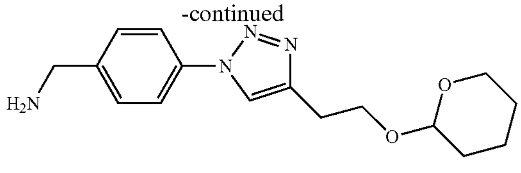

22

A mixture of (4-iodophenyl)methanamine (5.0 g, 21.45 mmol, 1.0 eq), (1S,2S)—N1,N2-dimethylcyclohexane-1,2-diamine (0.44 mL 2.79 mmol, 0.13 eq), Sodium ascorbate (425 mg, 2.15 mmol, 0.1 eq), Copper Iodide (409 mg, 2.15 mmol, 0.1 eq), Sodium azide (2.79 g, 42.91 mmol, 2.0 eq), and 2-(but-3-yn-1-yloxy)tetrahydro-2H-pyran (3.36 mL, 21.45 mmol, 1.0 eq) in Methanol (20 mL) and water (5 mL) were purged with Nitrogen for 5 minutes and heated to 55° C. for over night. The reaction mixture was cooled to room temperature and filtered through 413 filter paper. Celite (10 g) was added and the solvent was removed under reduced pressure and the residue was purified over silica gel (220 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 5% to afford (4-(4-(2-((tetrahydro-2H-pyran-2-yl)oxy)ethyl)-1H-1,2,3-triazol-1-yl)phenyl)methanamine (22, 3.15 g, 49%) as a solid. LCMS m/z: $[M+H]^+$ Calcd for $C_{16}H_{22}N_4O_2$ 303.18; Found 303.18.

Experimental Procedure for N-(4-(4-(2-((tetrahydro-2H-pyran-2-yl)oxy)ethyl)-1H-1,2,3-triazol-1-yl)benzyl)methacrylamide (23)

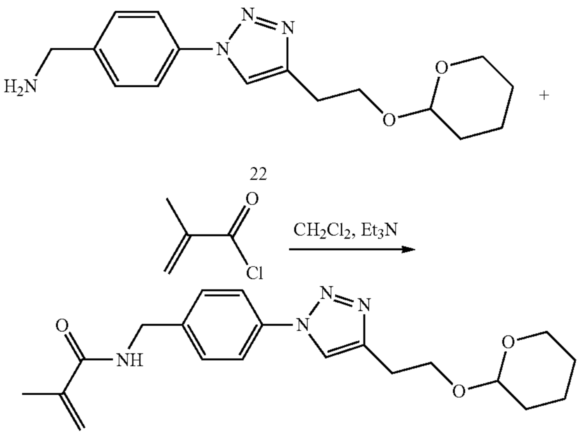

22

23

A solution of (4-(4-(2-((tetrahydro-2H-pyran-2-yl)oxy)ethyl)-1H-1,2,3-triazol-1-yl)phenyl)methanamine (22, 3.10 g, 10.25 mmol, 1.0 eq) and triethylamine (1.71 mL, 12.30 mmol, 1.2 eq) in $CH_2Cl_2$(55 mL) was cooled to 0° C. with an ice-bath and methacryloyl chloride (1.05 mL, 12.30 mmol, 1.2 eq, diluted in 5 mL of $CH_2Cl_2$) was added in a dropwise fashion. The cooling bath was removed and the reaction was stirred for 4 h. 8 grams of Celite was added and the solvent was removed under reduced pressure. The residue was purified by silica gel chromatography (80 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 2.5% to afford N-(4-(4-(2-((tetrahydro-2H-pyran-2-yl)oxy)ethyl)-1H-1,2,3-triazol-1-yl)benzyl)methacrylamide (23, 2.06 g, 54% yield) as a white solid. LCMS m/z: $[M+H]^+$ Calcd for $C_{20}H_{26}N_4O_3$ 371.2078; Found 371.2085.

Experimental Procedure (4-(1-(2-((tetrahydro-2H-pyran-2-yl)oxy)ethyl)-1H-1,2,3-triazol-4-yl)phenyl) methanamine (24)

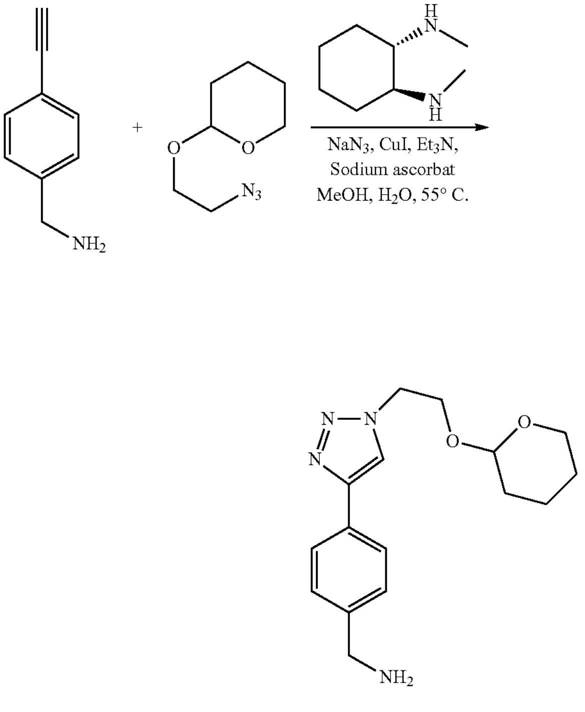

24

A mixture of (4-ethynylphenyl)methanamine (2.36 g, 18.00 mmol, 1.0 eq), (1S,2S)—N1,N2-dimethylcyclohexane-1,2-diamine (0.56 mL, 3.60 mmol, 0.2 eq), Sodium ascorbate (357 mg, 1.80 mmol, 0.1 eq), Copper Iodide (514 mg, 2.70 mmol, 0.15 eq), and 2-(2-azidoethoxy)tetrahydro-2H-pyran (3.08, 18.00 mmol, 1.0 eq) in Methanol (24 mL) and water (6 mL) were purged with Nitrogen for 5 minutes and heated to 55° C. for over night. The reaction mixture was cooled to room temperature and filtered over Celite and rinsed with MeOH (3×50 mL). The solvent was removed under reduced pressure and the residue was redissolved in dichloromethane, Celite (20 g) was added and the solvent was removed under reduced pressure and the residue was purified over silica gel (120 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 25% to afford (4-(1-(2-((tetrahydro-2H-pyran-2-yl)oxy)ethyl)-1H-1,2,3-triazol-4-yl)phenyl)methanamine (24, 3.51 g, 64%) as a yellowish oil. LCMS m/z: $[M+H]^+$ Calcd for $C_{16}H_{22}N_4O_2$ 303.1816; Found 303.1814.

Experimental Procedure for N-(4-(1-(2-((tetrahydro-2H-pyran-2-yl)oxy)ethyl)-1H-1,2,3-triazol-4-yl)benzyl)methacrylamide (25)

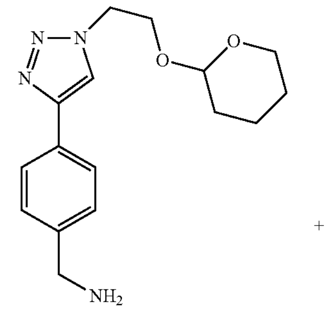

24

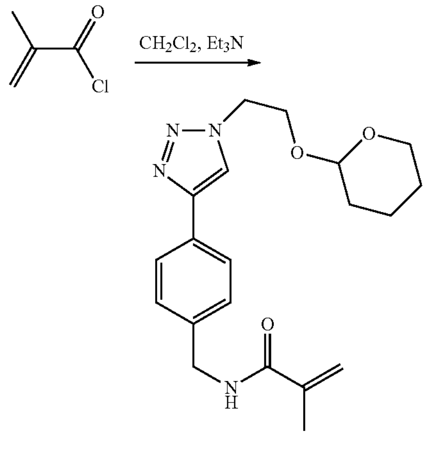

25

A solution of (4-(1-(2-((tetrahydro-2H-pyran-2-yl)oxy)ethyl)-1H-1,2,3-triazol-4-yl)phenyl)methanamine (24, 1.5 g, 4.96 mmol, 1.0 eq) and triethylamine (1.04 mL, 7.44 mmol, 1.5 eq) in $CH_2Cl_2$(30 mL) were briefly evacuated and flushed with Nitrogen. Methacryloyl chloride (0.72 mL, 7.44 mmol, 1.5 eq) was added in a dropwise fashion. The reaction mixture was stirred for 2 h at room temperature. 10 grams of Celite was added and the solvent was removed under reduced pressure. The residue was purified by silica gel chromatography (40 g) using Hexanes/EtOAc as eluent starting at 100% Hexanes and increasing the concentration of EtOAc gradually to 100% to afford N-(4-(1-(2-((tetrahydro-2H-pyran-2-yl)oxy)ethyl)-1H-1,2,3-triazol-4-yl)benzyl)methacrylamide (25, 0.9 g, 49% yield) as a colorless solid. LCMS m/z: $[M+Na]^+$ Calcd for $C_{20}H_{26}N_4O_3$ 371.2078; Found 371.2076.

Experimental Procedure for 1-(4-(4-(((tetrahydro-2H-pyran-2-yl)oxy)methyl)-1H-1,2,3-triazol-1-yl)phenyl)ethan-1-amine (26)

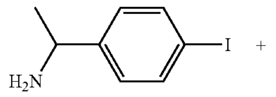

-continued

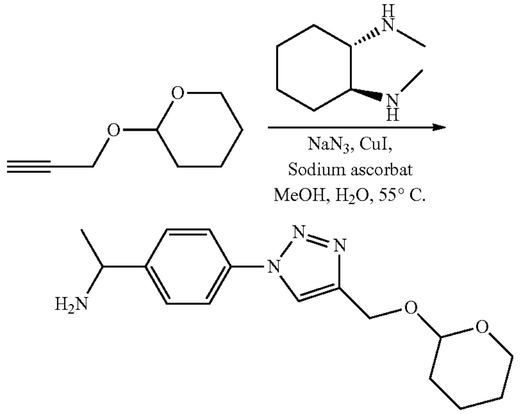

26

A mixture of 1-(4-iodophenyl)ethan-1-amine hydrochloride (1.0 g, 4.05 mmol, 1.0 eq), (1S,2S)—N1,N2-dimethylcyclohexane-1,2-diamine (0.08 mL 0.53 mmol, 0.13 eq), Sodium ascorbate (80 mg, 0.40 mmol, 0.1 eq), Copper Iodide (77 mg, 0.40 mmol, 0.1 eq), Sodium azide (526 g, 8.09 mmol, 2.0 eq), and 2-(prop-2-yn-1-yloxy)tetrahydro-2H-pyran (0.57 g, 4.05 mmol, 1.0 eq) in Methanol (9 mL) and water (1 mL) were purged with Nitrogen for 5 minutes and heated to 55° C. for over night. The reaction mixture was cooled to room temperature and the solvent was removed under reduced pressure. The residue was redissolved in dichloromethane and filtered over a plug of Celite. Celite was added to the filtrate and the solvent was removed under reduced pressure. The residue was purified over silica gel (40 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 5% to afford 1-(4-(4-(((tetrahydro-2H-pyran-2-yl)oxy)methyl)-1H-1,2,3-triazol-1-yl)phenyl)ethan-1-amine (26, 0.62 g, 51%) as a yellowish solid. LCMS m/z: $[M+H]^+$ Calcd for $C_{16}H_{22}N_4O_2$ 303.2; Found 303.2.

Experimental Procedure for N-(1-(4-(4-(((tetrahydro-2H-pyran-2-yl)oxy)methyl)-1H-1,2,3-triazol-1-yl)phenyl)ethyl)methacrylamide (27)

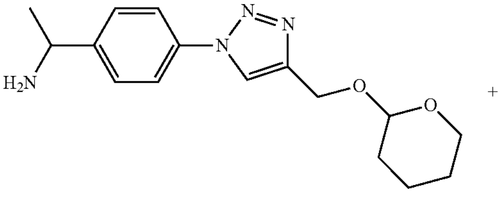

26

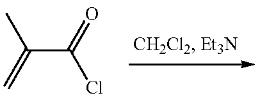

-continued

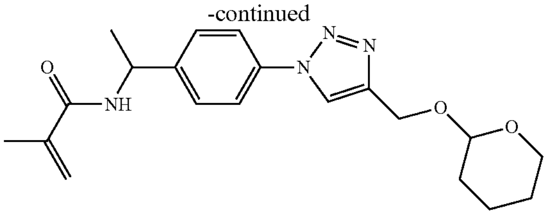

27

A solution of 1-(4-(4-(((tetrahydro-2H-pyran-2-yl)oxy)methyl)-1H-1,2,3-triazol-1-yl)phenyl)ethan-1-amine (26, 0.52 g, 1.7 mmol, 1.0 eq) and triethylamine (0.29 mL, 2.1 mmol, 1.2 eq) in $CH_2Cl_2$(11 mL) was cooled to 0° C. with an ice-bath and methacryloyl chloride (0.18 mL, 1.8 mmol, 1.05 eq, diluted in 11 mL of $CH_2Cl_2$) was added in a dropwise fashion. The cooling bath was removed and the reaction was stirred for 4 h. 5 grams of Celite was added and the solvent was removed under reduced pressure. The residue was purified by silica gel chromatography (40 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 2.5% to afford N-(1-(4-(4-(((tetrahydro-2H-pyran-2-yl)oxy)methyl)-1H-1,2,3-triazol-1-yl)phenyl)ethyl)methacrylamide (27, 0.49 g, 76% yield) as a white solid. LCMS m/z: $[M+H]^+$ Calcd for $C_{20}H_{26}N_4O_3$ 371.2078; Found 371.2087.

Experimental Procedure for (4-(4-(((tetrahydro-2H-pyran-2-yl)oxy)methyl)-1H-1,2,3-triazol-1-yl)-2-(trifluoromethyl)phenyl)methanamine (28)

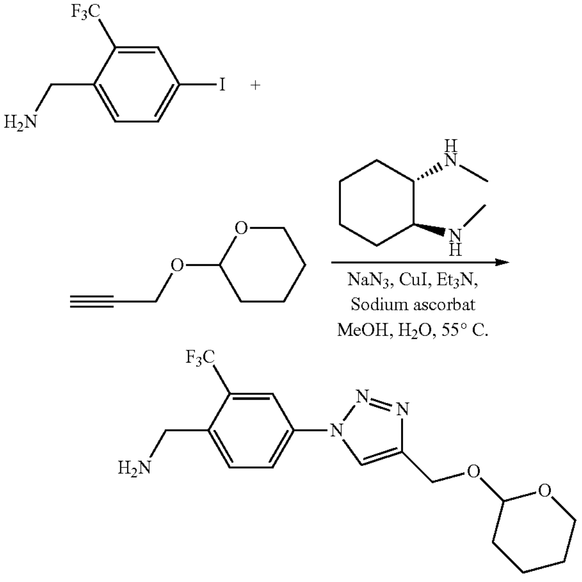

28

A mixture of (4-iodo-2-(trifluoromethyl)phenyl)methanamine (3.0 g, 9.97 mmol, 1.0 eq), (1S,2S)—N1,N2-dimethylcyclohexane-1,2-diamine (0.31 mL 1.99 mmol, 0.2 eq), Sodium ascorbate (197 mg, 1.00 mmol, 0.1 eq), Copper Iodide (285 mg, 1.49 mmol, 0.15 eq), Sodium azide (1.30 g, 19.93 mmol, 2.0 eq), $Et_3N$ (1.67 mL, 11.96 mmol, 1.2 eq) and 2-(prop-2-yn-l-yloxy)tetrahydro-2H-pyran (1.40 g, 9.97 mmol, 1.0 eq) in Methanol (24 mL) and water (6 mL) were purged with Nitrogen for 5 minutes and heated to 55° C. for over night. The reaction mixture was cooled to room temperature and filtered through a plug of Celite and rinsed with Methanol (3x50 mL). Celite was added to the filtrate and the solvent was removed under reduced pressure. The residue was purified over silica gel (120 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 25% to afford (4-(4-(((tetrahydro-2H-pyran-2-yl)oxy)methyl)-1H-1,2,3-triazol-1-yl)-2-(trifluoromethyl)phenyl)methanamine (28, 2.53 g, 71%) as a green oil. LCMS m/z: $[M+H]^+$ Calcd for $C_{16}H_{19}N_4O_2F_3$ 357.2; Found 357.1.

Experimental Procedure for N-(4-(4-(((tetrahydro-2H-pyran-2-yl)oxy)methyl)-1H-1,2,3-triazol-1-yl)-2 (trifluoromethyl)benzyl) methacrylamide (29)

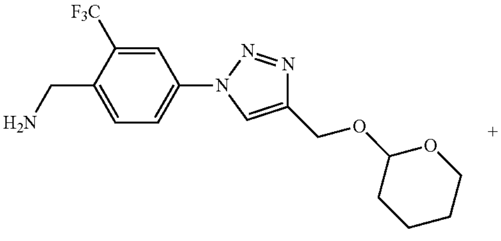

28

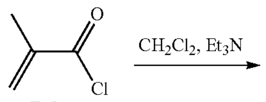

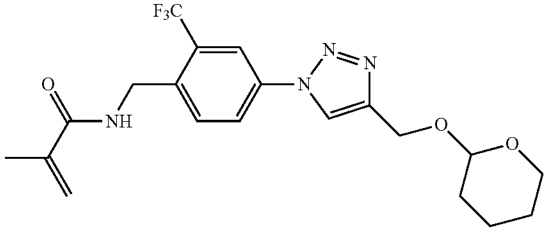

29

A solution of (4-(4-(((tetrahydro-2H-pyran-2-yl)oxy)methyl)-1H-1,2,3-triazol-1-yl)-2-(trifluoromethyl)phenyl)methanamine (28, 1.0 g, 2.81 mmol, 1.0 eq) and triethylamine (0.59 mL, 4.21 mmol, 1.5 eq) in $CH_2Cl_2$(25 mL) were briefly evacuated and flushed with Nitrogen. Methacryloyl chloride (0.41 mL, 4.21 mmol, 1.5 eq) was added in a dropwise fashion. The reaction mixture was stirred for 6 h at room temperature. 10 grams of Celite was added and the solvent was removed under reduced pressure. The residue was purified by silica gel chromatography (40 g) using Hexanes/EtOAc as eluent starting at 100% Hexanes and increasing the concentration of EtOAc gradually to 100% to afford N-(4-(4-(((tetrahydro-2H-pyran-2-yl)oxy)methyl)-1H-1,2,3-triazol-1-yl)-2(trifluoromethyl)benzyl) methacrylamide (29, 0.65 g, 55% yield) as a colorless solid. LCMS m/z: $[M+H]^+$ Calcd for $C_{20}H_{23}N_4O_3F_3$ 425.2; Found 425.1.

Experimental Procedure for 3-(4-(((tetrahydro-2H-pyran-2-yl)oxy)methyl)-1H-1,2,3-triazol-1-yl)propan-1-amine (30)

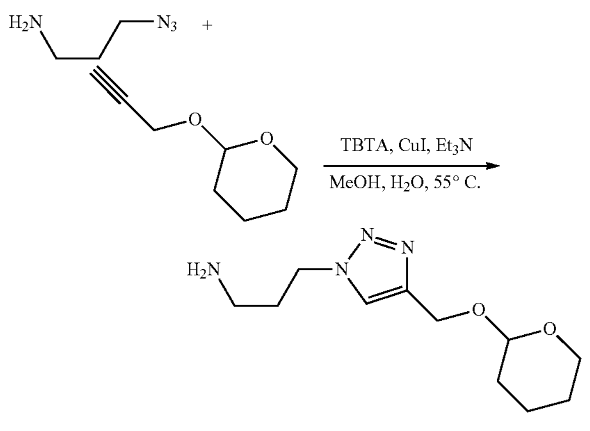

30

A mixture of 3-azidopropan-1-amine hydrochloride (1.5 g, 14.98 mmol, 1.0 eq), Tris[(1-benzyl-1H-1,2,3-triazol-4-yl)methyl]-amine (1.99 g, 3.75 mmol, 0.25 eq), Copper Iodide (0.29 g, 1.50 mmol, 0.1 eq), and Triethylamine (0.52 mL, 3.75 mmol, 0.25 eq) in Methanol (50 mL) and water (6 mL) were purged with Nitrogen for 5 minutes and cooled to 0 C. 2-(prop-2-yn-1-yloxy)tetrahydro-2H-pyran (2.10 g, 14.98 mmol, 1.0 eq) was added and the reaction mixture was warmed to 55° C. and stirred over night under Nitrogen atmosphere. The reaction mixture was cooled to room temperature, filtered over a plug of Celite and rinsed with Methanol (3×50 mL). Celite (20 g) was added to the filtrate the solvent was removed under reduced pressure. The residue was purified over silica gel (120 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 20% to afford 3-(4-(((tetrahydro-2H-pyran-2-yl)oxy)methyl)-1H-1,2,3-triazol-1-yl)propan-1-amine (30, 2.36 g, 66%). LCMS m/z: $[M+H]^+$ Calcd for $C_{11}H_{20}N_4O_2$ 241.2; Found 241.2.

Experimental Procedure for N-(3-(4-(((tetrahydro-2H-pyran-2-yl)oxy)methyl)-1H-1,2,3-triazol-1-yl)propyl)methacrylamide (31)

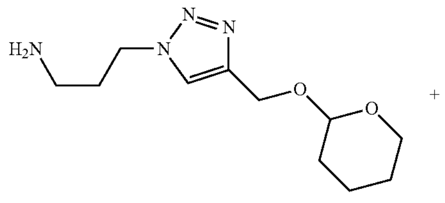

30

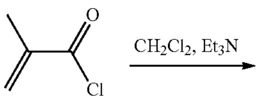

-continued

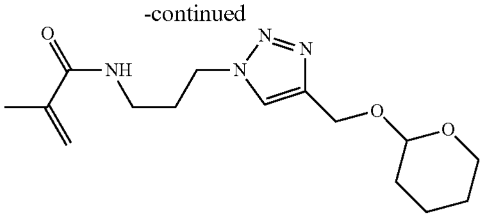

31

A solution of 3-(4-(((tetrahydro-2H-pyran-2-yl)oxy)methyl)-1H-1,2,3-triazol-1-yl)propan-1-amine (30, 1.0 g, 4.16 mmol, 1.0 eq) and triethylamine (0.58 mL, 4.16 mmol, 1.0 eq) in $CH_2Cl_2$(20 mL) were briefly evacuated and flushed with Nitrogen. Methacryloyl chloride (0.40 mL, 4.16 mmol, 1.0 eq) was added in a dropwise fashion. The reaction mixture was stirred at room temperature over night. 10 grams of Celite was added and the solvent was removed under reduced pressure. The residue was purified by silica gel chromatography (40 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 20% to afford N-(3-(4-(((tetrahydro-2H-pyran-2-yl)oxy)methyl)-1H-1,2,3-triazol-1-yl)propyl)methacrylamide (31, 0.96 g, 75% yield) as a colorless oil. LCMS m/z: $[M+H]^+$ Calcd for $C_{15}H_{24}N_4O_3$ 309.2; Found 309.4.

Experimental Procedure for (4-(4-((oxetan-3-yloxy)methyl)-1H-1,2,3-triazol-1-yl)phenyl)methanamine (32)

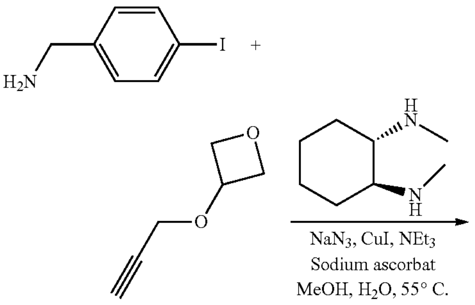

9

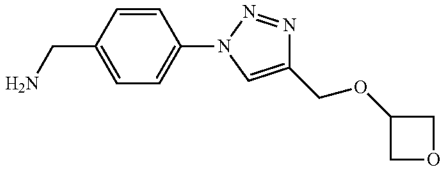

32

A mixture of (4-iodophenyl)methanamine hydrochloride (2.64 g, 9.80 mmol, 1.0 eq), (1S,2S)—N1,N2-dimethylcyclohexane-1,2-diamine (0.31 mL 1.96 mmol, 0.2 eq), Sodium ascorbate (198 mg, 0.98 mmol, 0.1 eq), Copper Iodide (279 mg, 1.47 mmol, 0.15 eq), Sodium azide (1.27 g, 19.59 mmol, 2.0 eq), $Et_3N$ (1.64 mL, 11.75 mmol, 1.2 eq) and 3-(prop-2-yn-1-yloxy)oxetane (9, 1.10 g, 9.80 mmol, 1.0 eq) in Methanol (24 mL) and water (6 mL) were purged with Nitrogen for 5 minutes and heated to 55° C. for over night. The reaction mixture was cooled to room temperature and filtered through a plug of Celite and rinsed with Methanol (3×50 mL). Celite was added to the filtrate and the solvent was removed under reduced pressure. The residue was purified over silica gel (120 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 25% to afford (4-(4-((oxetan-3-yloxy)methyl)-1H-1,2,3-triazol-1-yl)phenyl)methanamine (32, 1.43 g, 56%) as an oil. LCMS m/z: $[M+H]^+$ Calcd for $C_{13}H_{16}N_4O_2$ 261.1346; Found 261.1342.

Experimental Procedure for N-(4-(4-((oxetan-3-yloxy)methyl)-1H-1,2,3-triazol-1-yl)benzyl)methacrylamide (33)

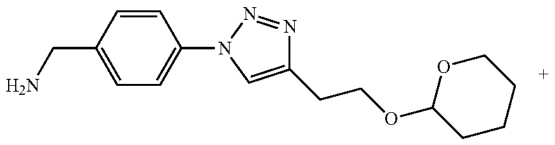

32

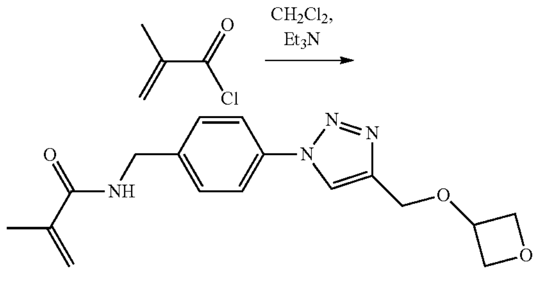

33

A solution of (4-(4-((oxetan-3-yloxy)methyl)-1H-1,2,3-triazol-1-yl)phenyl)methanamine (32, 0.58 g, 2.23 mmol, 1.0 eq) and triethylamine (0.47 mL, 3.34 mmol, 1.5 eq) in $CH_2Cl_2$(20 mL) were briefly evacuated and flushed with Nitrogen. Methacryloyl chloride (0.32 mL, 3.34 mmol, 1.5 eq) was added in a dropwise fashion. The reaction mixture was stirred for 6 h at room temperature. 10 grams of Celite was added and the solvent was removed under reduced pressure. The residue was purified by silica gel chromatography (24 g) using Hexanes/EtOAc as eluent starting at 100% Hexanes and increasing the concentration of EtOAc gradually to 100% to afford N-(4-(4-((oxetan-3-yloxy)methyl)-1H-1,2,3-triazol-1-yl)benzyl)methacrylamide (33, 0.48 g, 66% yield) as a colorless solid. LCMS m/z: $[M+H]^+$ Calcd for $C_{17}H_{20}N_4O_3$ 329.1608; Found 329.1611.

Experimental Procedure for ethyl 1-(2-methacrylamidoethyl)-M-imidazole-4-carboxylate (35)

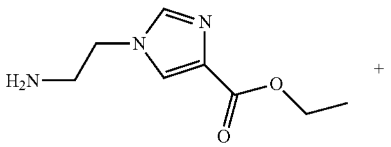

34

-continued

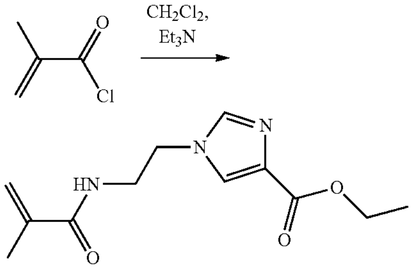

35

A solution of ethyl 1-(2-aminoethyl)-1H-imidazole-4-carboxylate (34, 2.0 g, 10.91 mmol, 1.0 eq) and triethylamine (3.80 mL, 27.29 mmol, 2.5 eq) in $CH_2Cl_2$(20 mL) were briefly evacuated and flushed with Nitrogen. Methacryloyl chloride (1.60 mL, 16.37 mmol, 1.5 eq) was added in a dropwise fashion. The reaction mixture was stirred for 3 h at room temperature. 15 grams of Celite was added and the solvent was removed under reduced pressure. The residue was purified by silica gel chromatography (40 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 25% to afford ethyl 1-(2-methacrylamidoethyl)-1H-imidazole-4-carboxylate (35, 1.28 g, 47% yield) as a colorless solid. LCMS m/z: $[M+H]^+$ Calcd for $C_{12}H_{17}N_3O_3$ 252.1; Found 252.1.

Experimental Procedure for N-(4-(1,1-dioxidothiomorpholino)benzyl)methacrylamide (37)

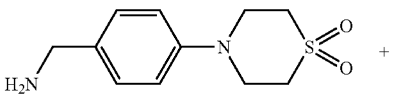

36

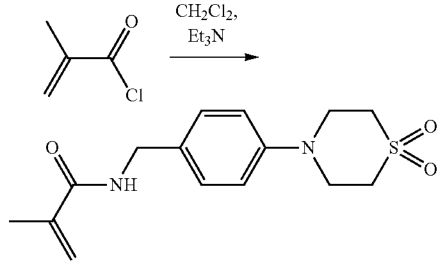

37

To a solution of 4-(4-(aminomethyl)phenyl)thiomorpholine 1,1-dioxide hydrochloride (36, 1.15 g, 4.15 mmol, 1.0 eq) and triethylamine (1.39 mL, 9.97 mmol, 2.4 eq) in $CH_2Cl_2$(80 mL) was added a solution of methacryloyl chloride (0.43 mL, 4.36 mmol, 1.05 eq, in $CH_2Cl_2$, 5 mL) in a dropwise fashion. The reaction mixture was stirred for 22 h at room temperature. 8 grams of Celite was added and the solvent was removed under reduced pressure. The residue was purified by silica gel chromatography (80 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 3.75% to afford N-(4-(1,1-dioxidothiomorpholino)benzyl) methacrylamide (37, 0.32 g, 25% yield) as a solid.

Experimental Procedure for N-methyl-N-(2-(methylsulfonyl)ethyl)prop-2-yn-1-amine (38)

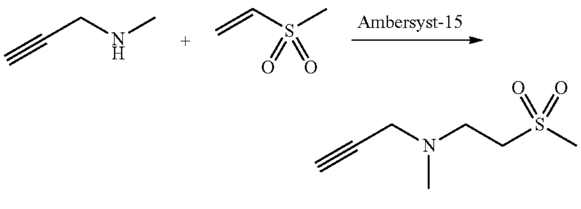

38

To a mixture of 1-methylsulfonylethylene (4.99 g, 47.03 mmol, 4.13 mL) and Amberlyst-15 ((30% w/w)), N-methylprop-2-yn-1-amine (2.6 g, 37.62 mmol) was added in a dropwise fashion. The mixture was stirred at room temperature for 12 hours. The catalyst was removed by filtration and the filtrate was concentrated under reduced pressure to afford: N-methyl-N-(2-(methylsulfonyl)ethyl)prop-2-yn-1-amine (38, 6.43 g, 98%) as an oil. LCMS m/z: $[M+H]^+$ Calcd for $C_7H_{13}NSO_2$ 176.11; Found 176.1.

Experimental Procedure for N-((1-(2-(2-(2-(2-aminoethoxy)ethoxy)ethoxy)ethyl)-1H-1,2,3-triazol-4-yl)methyl)-N-methyl-2-(methylsulfonyl)ethan-1-amine (40)

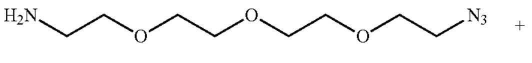

39

-continued

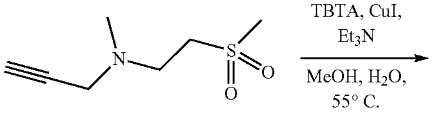

38

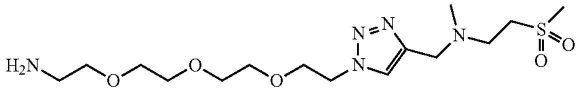

40

A mixture of N-methyl-N-(2-(methylsulfonyl)ethyl)prop-2-yn-1-amine (38, 5.02 g, 28.64 mmol, 1.25 eq), Tris[(1-benzyl-1H-1,2,3-triazol-4-yl)methyl]-amine (3.04 g, 5.73 mmol, 0.25 eq), Copper Iodide (436 mg, 2.29 mmol, 0.1 eq), and Triethylamine (0.8 mL, 5.7 mmol, 0.25 eq) in Methanol (50 mL) and water (6 mL) was evacuated and flushed with Nitrogen (3 times) and cooled with an ice bath. 2-(2-(2-(2-azidoethoxy)ethoxy)ethoxy)ethan-1-amine (39, 5.02 g, 22.91 mmol, 1.0 eq) was added in a dropwise fashion, the cooling bath was removed and the mixture was stirred for 5 minutes. The reaction was warmed to 55° C. and stirred over night under Nitrogen atmosphere. The reaction mixture was cooled to room temperature, Celite (20 g) was added, and concentrated under reduced pressure. The crude product was purified over silica gel (220 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 25% to afford N-((1-(2-(2-(2-(2-aminoethoxy)ethoxy)ethoxy)ethyl)-1H-1,2,3-triazol-4-yl)methyl)-N-methyl-2-(methylsulfonyl)ethan-1-amine (40, 4.98 g, 55%) as an oil. LCMS m/z: $[M+H]^+$ Calcd for $C_{15}H_{31}N_5O_5S$ 394.2; Found 394.2.

Experimental Procedure N-(2-(2-(2-(2-(4-((methyl (2-(methylsulfonyl)ethyl)amino)methyl)-1H-1,2,3-triazol-1-yl)ethoxy)ethoxy)ethoxy)ethyl)methacrylamide (41)

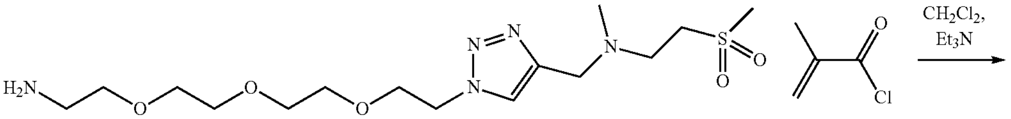

40

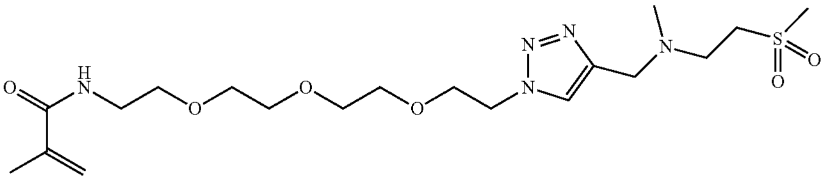

41

To a solution of N-((1-(2-(2-(2-(2-aminoethoxy)ethoxy)ethoxy)ethyl)-1H-1,2,3-triazol-4-yl)methyl)-N-methyl-2-(methylsulfonyl)ethan-1-amine (40, 1.0 g, 2.54 mmol, 1.0 eq) and triethylamine (0.43 mL, 3.05 mmol, 1.2 eq) in $CH_2Cl_2$(15 mL) was added a solution of methacryloyl chloride (0.30 mL, 3.05 mmol, 1.5 eq) in a dropwise fashion. The reaction mixture was stirred for 5 h at room temperature. Celite was added and the solvent was removed under reduced pressure. The residue was purified by silica gel chromatography (40 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 12.5% to afford N-(2-(2-(2-(2-(4-((methyl(2-(methylsulfonyl)ethyl)amino)methyl)-1H-1,2,3-triazol-1-yl)ethoxy)ethoxy)ethoxy)ethyl)methacrylamide (41, 0.86 g, 73% yield) as an oil. LCMS m/z: $[M+H]^+$ Calcd for $C_{19}H_{35}N_5O_6S$ 462.2; Found 462.2.

Experimental Procedure for 7-(prop-2-yn-1-yl)-2-oxa-7-azaspiro[3.5]nonane (42)

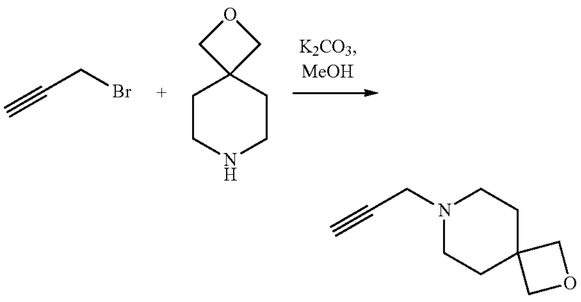

42

3-Bromoprop-1-yne (4.4 mL, 39.32 mmol 1.0 eq) was added to a mixture of 2-oxa-7-azaspiro[3.5]nonane (8.54 g, 39.32 mmol, 1.0 eq), potassium carbonate (17.9 g, 129.7 mmol, 3.3 eq) in Methanol (200 mL) and stirred over night at room temperature. The mixture was filtered, Celite was added and the solvent was removed under reduced pressure. The residue was purified by silica gel chromatography (220 g) using dichloromethane/methanol as mobile phase. The concentration of methanol was gradually increased from 0% to 5% to afford 7-(prop-2-yn-1-yl)-2-oxa-7-azaspiro[3.5]nonane (42, 4.44 g, 68%) as an oil.

Experimental Procedure for 2-(2-(2-(2-(4-((2-oxa-7-azaspiro[3.5]nonan-7-yl)methyl)-1H-1,2,3-triazol-1-yl)ethoxy)ethoxy)ethoxy)ethan-l-amine (43)

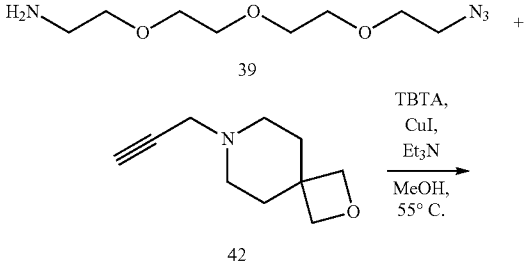

39

42

-continued

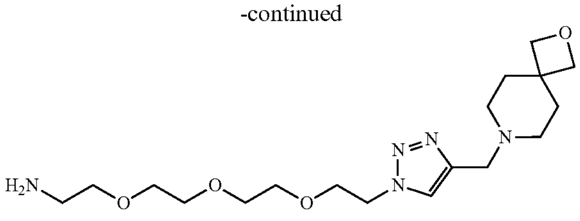

43

A mixture of 7-(prop-2-yn-1-yl)-2-oxa-7-azaspiro[3.5]nonane (42, 2.5 g, 15.13 mmol, 1.0 eq), Tris[(1-benzyl-1H-1,2,3-triazol-4-yl)methyl]-amine (1.77 g, 3.33 mmol, 0.22 eq), Copper Iodide (288 mg, 1.51 mmol, 0.1 eq), and Triethylamine (0.53 mL, 3.8 mmol, 0.25 eq) in Methanol (50 mL) was cooled with an ice bath. 2-(2-(2-(2-azidoethoxy)ethoxy)ethoxy)ethan-l-amine (39, 3.86 g, 17.70 mmol, 1.17 eq) was added in a dropwise fashion, the cooling bath was removed and the mixture was stirred for 5 minutes. The reaction was warmed to 55° C. and stirred over night under Nitrogen atmosphere. The reaction mixture was cooled to room temperature, Celite (10 g) was added, and concentrated under reduced pressure. The crude product was purified over silica gel (220 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 10% to afford for 2424242444(2-oxa-7-azaspiro[3.5]nonan-7-yl)methyl)-1H-1,2,3-triazol-1-yl)ethoxy)ethoxy)ethoxy)ethan-1-amine (43, 4.76 g, 82%) as an oil. LCMS m/z: $[M+H]^+$ Calcd for $C_{18}H_{33}N_5O_4$ 384.3; Found 384.2.

Experimental Procedure for N-(2-(2-(2-(2-(4-((2-oxa-7-azaspiro[3.5]nonan-7-yl)methyl)-1H-1,2,3-triazol-1-yl)ethoxy)ethoxy)ethoxy)ethyl)methacrylamide (44)

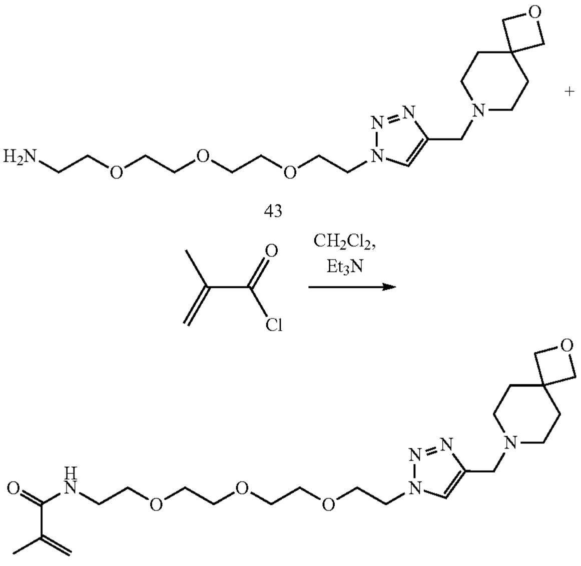

43

44

A solution of 2-(2-(2-(2-(4-((2-oxa-7-azaspiro[3.5]nonan-7-yl)methyl)-1H-1,2,3-triazol-1-yl)ethoxy)ethoxy)ethoxy)

ethan-1-amine (43, 2.65 g, 6.91 mmol, 1.0 eq) and triethylamine (1.16 mL, 8.29 mmol, 1.2 eq) in $CH_2Cl_2$(100 mL) was cooled with an ice-bath under Nitrogen atmosphere. Methacryloyl chloride (0.74 mL, 7.6 mmol, 1.1 eq) was added in a dropwise fashion. The cooling bath was removed and the reaction mixture was stirred for 4 h at room temperature. 10 grams of Celite was added and the solvent was removed under reduced pressure. The residue was purified by silica gel chromatography (120 g) using dichloromethane/methanol as mobile phase. The concentration of methanol was gradually increased from 0% to 10% to afford N-(2-(2-(2-(2-(4-(2-oxa-7-azaspiro[3.5]nonan-7-yl) methyl)-1H-1,2,3-triazol-1-yl)ethoxy)ethoxy)ethoxy)ethyl) methacrylamide (44, 1.50 g, 48% yield) as a colorless oil. LCMS m/z: $[M+H]^+$ Calcd for $C_{22}H_{37}N_5O_5$ 452.29; Found 452.25.

Experimental Procedure for 4-((1-(2-(2-aminoethoxy)ethyl)-1H-1,2,3-triazol-4-yl)methyl)thiomorpholine 1,1-dioxide (45)

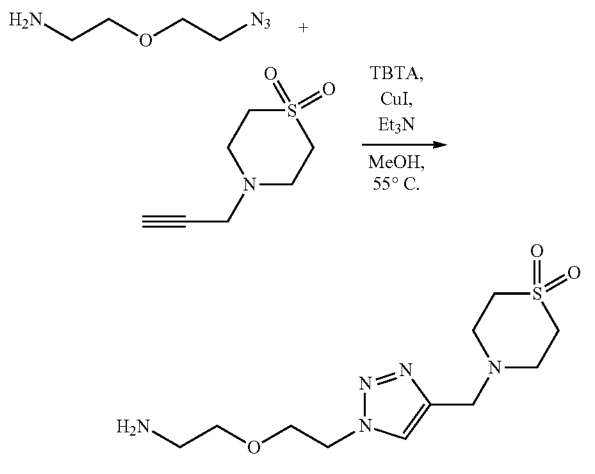

45

A mixture of 4-(prop-2-yn-1-yl)thiomorpholine 1,1-dioxide (1.14 g, 6.58 mmol, 1.0 eq), Tris[1-benzyl-1H-1,2,3-triazol-4-yl)methyl]-amine (768 mg, 1.45 mmol, 0.22 eq), Copper Iodide (125 mg, 0.66 mmol, 0.1 eq), and Triethylamine (0.23 mL, 1.65 mmol, 0.25 eq) in Methanol (20 mL) was cooled with an ice bath. 2-(2-azidoethoxy)ethan-1-amine (1.00 g, 7.70 mmol, 1.17 eq) was added in a dropwise fashion, the cooling bath was removed and the mixture was stirred for 5 minutes. The reaction was warmed to 55° C. and stirred over night under Nitrogen atmosphere. The reaction mixture was cooled to room temperature, Celite (10 g) was added, and concentrated under reduced pressure. The crude product was purified over silica gel (40 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 9.5% to afford for 4-((1-(2-(2-aminoethoxy)ethyl)-1H-1,2,3-triazol-4-yl)methyl)thiomorpholine 1,1-dioxide (45, 1.86 g, 93%) as a white solid. LCMS m/z: $[M+H]^+$ Calcd for $C_{11}H_{21}N_5O_4S$ 304.1438; Found 304.1445.

Experimental Procedure for N-(2-(2-(4-((1,1-dioxidothiomorpholino)methyl)-1H-1,2,3-triazol-1-yl) ethoxy)ethyl)methacrylamide (46)

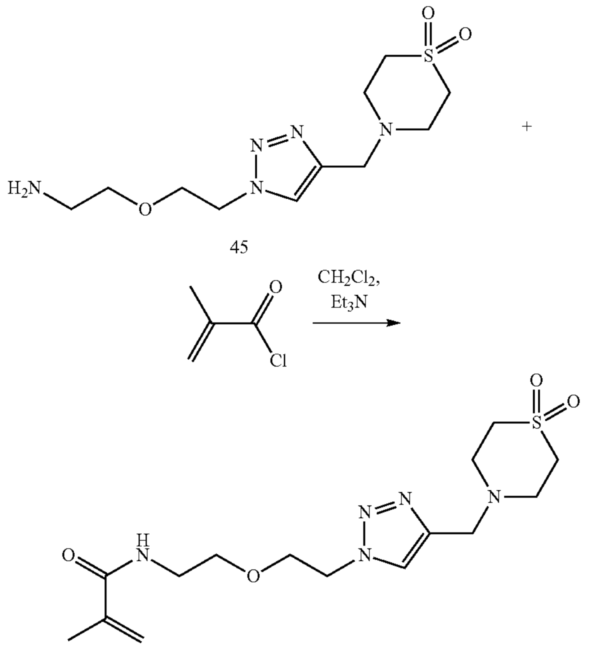

45

46

A solution of 4-((1-(2-(2-aminoethoxy)ethyl)-1H-1,2,3-triazol-4-yl)methyl)thiomorpholine 1,1-dioxide (45, 1.32 g, 4.35 mmol, 1.0 eq) and triethylamine (0.73 mL, 5.22 mmol, 1.2 eq) in $CH_2Cl_2$(100 mL) was cooled with an ice-bath under Nitrogen atmosphere. Methacryloyl chloride (0.47 mL, 4.8 mmol, 1.1 eq) was added in a dropwise fashion. The cooling bath was removed and the reaction mixture was stirred for 4 h at room temperature. 10 grams of Celite was added and the solvent was removed under reduced pressure. The residue was purified by silica gel chromatography (120 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 1.25% to afford N-(2-(2-(4-(1,1-dioxidothiomorpholino) methyl)-1H-1,2,3-triazol-1-l)ethoxy)ethyl)-methacrylamide (46, 0.90 g, 56% yield) as a colorless oil. LCMS m/z: $[M+H]^+$ Calcd for $C_{15}H_{25}N_5O_4S$ 372.17; Found 372.15.

Experimental Procedure for 4-((1-(2-(2-(2-aminoethoxy)ethoxy)ethyl)-1H-1,2,3-triazol-4-yl)methyl) thiomorpholine 1,1-dioxide (47)

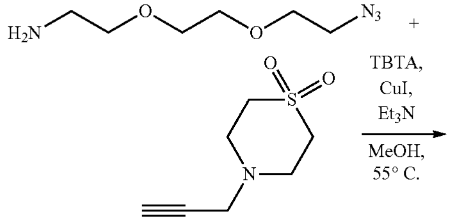

-continued

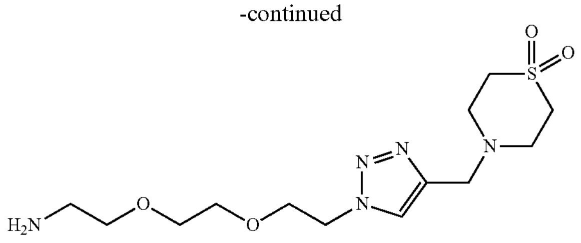

47

A mixture of 4-(prop-2-yn-1-yl)thiomorpholine 1,1-dioxide (4.6 g, 26.55 mmol, 1.0 eq), Tris[(1-benzyl-1H-1,2,3-triazol-4-yl)methyl]-amine (3.1 g, 5.84 mmol, 0.22 eq), Copper Iodide (506 mg, 2.66 mmol, 0.1 eq), and Triethylamine (0.93 mL, 6.64 mmol, 0.25 eq) in Methanol (80 mL) was cooled with an ice bath. 2-(2-(2-azidoethoxy)ethoxy)ethan-1-amine (5.00 g, 28.68 mmol, 1.08 eq) was added in a dropwise fashion, the cooling bath was removed and the mixture was stirred for 5 minutes. The reaction was warmed to 55° C. and stirred over night under Nitrogen atmosphere. The reaction mixture was cooled to room temperature, Celite was added, and concentrated under reduced pressure. The crude product was purified over silica gel (220 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 10% to afford for 4-((1-(2-(2-(2-aminoethoxy)ethoxy)ethyl)-1H-1,2,3-triazol-4-yl)methyl)thiomorpholine 1,1-dioxide (47, 5.26 g, 57%) as a yellowish oil. LCMS m/z: $[M+H]^+$ Calcd for $C_{13}H_{25}N_5O_4S$ 348.1700; Found 348.1700.

Experimental Procedure N-(2-(2-(2-(4-((1,1-dioxidothiomorpholino)methyl)-1H-1,2,3-triazol-1-yl)ethoxy)ethoxy)ethyl)methacrylamide (48)

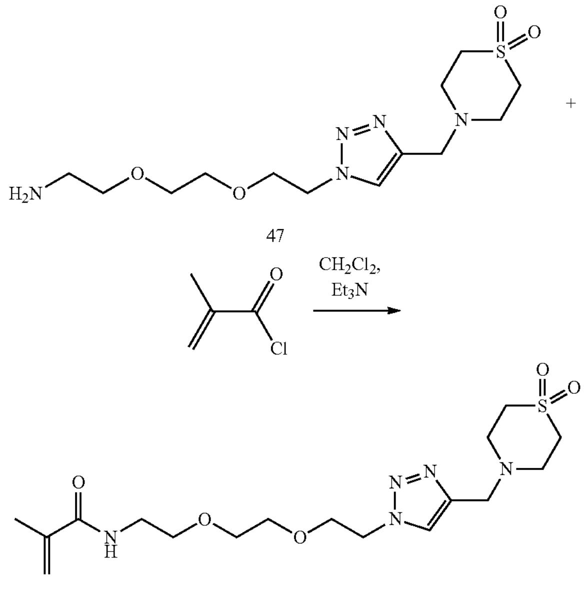

47

48

A solution of 4-((1-(2-(2-(2-aminoethoxy)ethoxy)ethyl)-1H-1,2,3-triazol-4-yl)methyl)thiomorpholine 1,1-dioxide (47, 1.49 g, 4.29 mmol, 1.0 eq) and triethylamine (0.72 mL, 5.15 mmol, 1.2 eq) in $CH_2Cl_2$(50 mL) was cooled with an ice-bath under Nitrogen atmosphere. Methacryloyl chloride (0.46 mL, 4.7 mmol, 1.1 eq) was added in a dropwise fashion. The cooling bath was removed and the reaction mixture was stirred for 4 h at room temperature. 10 grams of Celite was added and the solvent was removed under reduced pressure. The residue was purified by silica gel chromatography (80 g) using dichloromethane/methanol as mobile phase. The concentration of methanol was gradually increased from 0% to 5% to afford N-(2-(2-(2-(4-((1,1-dioxidothiomorpholino)methyl)-1H-1,2,3-triazol-1-yl)ethoxy)ethoxy)ethyl)-methacrylamide (48, 0.67 g, 38% yield) as a colorless oil. LCMS m/z: $[M+H]^+$ Calcd for $C_{17}H_{29}N_5O_5S$ 416.20; Found 416.20.

Experimental Procedure for 4-((1-(14-amino-3,6,9,12-tetraoxatetradecyl)-1H-1,2,3-triazol-4-yl)methyl)thiomorpholine 1,1-dioxide (49)

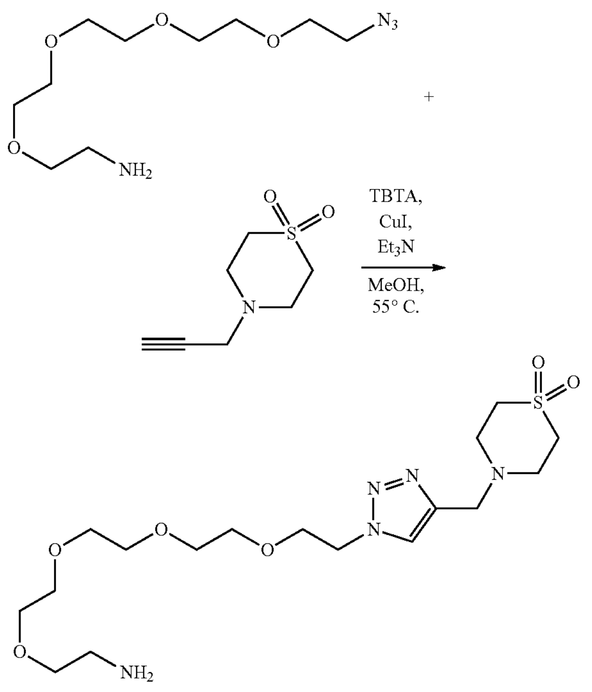

49

A mixture of 4-(prop-2-yn-1-yl)thiomorpholine 1,1-dioxide (5.0 g, 28.86 mmol, 1.0 eq), Tris[(1-benzyl-1H-1,2,3-triazol-4-yl)methyl]-amine (3.37 g, 6.35 mmol, 0.22 eq), Copper Iodide (550 mg, 2.89 mmol, 0.1 eq), and Triethylamine (1.01 mL, 7.22 mmol, 0.25 eq) in Methanol (90 mL) was cooled with an ice bath. 14-azido-3,6,9,12-tetraoxatetradecan-1-amine (8.86 g, 33.77 mmol, 1.17 eq) was added in a dropwise fashion, the cooling bath was removed and the mixture was stirred for 5 minutes. The reaction was warmed to 55° C. and stirred over night under Nitrogen atmosphere. The reaction mixture was cooled to room temperature, Celite (15 g) was added, and concentrated under reduced pressure. The crude product was purified over silica gel (220 g) using dichloromethane/(methanol containing 12% (v/v) aqueous ammonium hydroxide) as mobile phase. The concentration of (methanol containing 12% (v/v) aqueous ammonium hydroxide) was gradually increased from 0% to 10% to afford for 4-((1-(14-amino-3,6,9,12-tetraoxatetradecyl)-1H-1,2,3-triazol-4-yl)methyl)thiomorpholine 1,1-dioxide (49, 7.56 g, 60%) as an oil. LCMS m/z: $[M+H]^+$ Calcd for $C_{17}H_{33}N_5O_6S$ 436.2224; Found 436.2228.

Experimental Procedure N-(14-(4-((1,1-dioxidothiomorpholino)methyl)-1H-1,2,3-triazol-1-yl)-3,6,9,12-tetraoxatetradecyl)methacrylamide (50)

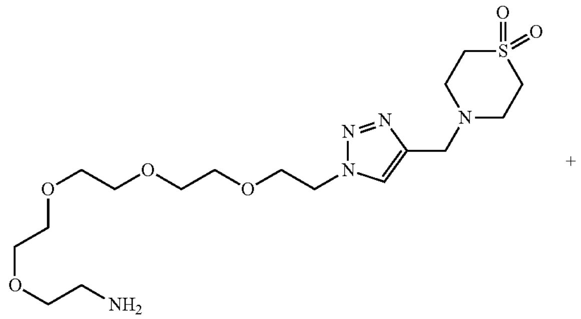

49

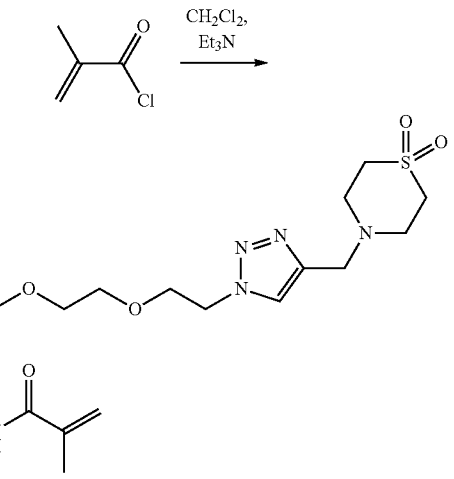

50

A solution of 4-((1-(14-amino-3,6,9,12-tetraoxatetradecyl)-1H-1,2,3-triazol-4-yl)methyl)thiomorpholine 1,1-dioxide (49, 1.95 g, 4.79 mmol, 1.0 eq) and triethylamine (0.80 mL, 5.74 mmol, 1.2 eq) in $CH_2Cl_2$(50 mL) was cooled with an ice-bath under Nitrogen atmosphere. Methacryloyl chloride (0.51 mL, 5.26 mmol, 1.1 eq) was added in a dropwise fashion. The cooling bath was removed and the reaction mixture was stirred for 4 h at room temperature. 10 grams of Celite was added and the solvent was removed under reduced pressure. The residue was purified by silica gel chromatography (80 g) using dichloromethane/methanol as mobile phase. The concentration of methanol was gradually increased from 0% to 5% to afford N-(14-(4-((1,1-dioxidothiomorpholino)methyl)-1H-1,2,3-triazol-1-yl)-3,6,9,12-tetraoxatetradecyl)methacrylamide (50, 0.76 g, 32% yield) as a colorless oil. LCMS m/z: $[M+H]^+$ Calcd for $C_{21}H_{37}N_5O_7S$ 504.25; Found 504.20.

Example 2: Conjugation of Exemplary Compounds to Polymers

Exemplary compounds may be attached to a polymer. In this example, compounds of the disclosure were conjugated to alginate, a polymer comprising reactive carboxylic acid groups. Any of the components capable of coupling to a carboxylic acid, such as an amine described herein, may be an appropriate partner for this coupling reaction.

Compounds 200-218 were conjugated to alginate using the method outlined herein. The alginate polymer was dissolved in water (30 mL/gram alginate) and treated with 2-chloro-4,6-dimethoxy-1,3,5-triazine (0.5 eq) and N-methylmorpholine (1 eq). The compound of interest (one of Compound 200-218) was then dissolved in acetonitrile (0.3M) and added to the alginate solution. The reaction was then warmed to 55° C. for 16 h, cooled to room temperature, concentrated via rotary evaporation, then dissolved in water. The mixture was then filtered through a bed of cyano-modified silica gel (Silicycle) and the filter cake was washed with water. The resulting solution was then dialyzed (10,000 MWCO membrane) against water for 24 hours, replacing the water twice. The resulting solution was concentrated via lyophilization to afford the functionalized alginate.

Example 3: Conjugation of Exemplary Compounds to NHS-Modified Plates

Exemplary compounds of the invention were prepared at a concentration of 0.1M in a 0.1M bicarbonate buffer (pH 8.2) containing 25% v/v dimethylsulfoxide (DMSO). Control solutions of 0.1M PEG750-amine and 0.01% fibronectin were prepared in 0.1M bicarbonate buffer (pH 8.2).

Each small molecule amine solution (100 μL) was pipetted into eight wells of an NHS-activated 96 well plate and incubated 2 hours at room temperature. Each plate consisted of two lanes containing the two control solutions and ten lanes containing the test molecule solutions. The test wells were rinsed once with 200 μL 0.1M bicarbonate buffer (pH 8.2) containing 25% v/v DMSO followed by three washes with 200 μL Hyclone™ water. The control wells were rinsed with 0.1M bicarbonate buffer (pH 8.2) followed by three 200 μL Hyclone™ water washes. Plates were dried at room temperature in a sterile hood and stored at 4-8° C. until use.

Example 4: Conjugation of Exemplary Compounds to Silicone Disks

Disks (5 mm) were cut from a medical grade silicone sheet (1 mm thick) using a biopsy punch. Disks were rinsed several times with HyClone water to remove particulates and then cleaned by sonication: 10 minutes each in 200 proof ethanol, acetone, and hexane. Cleaned disks were dried overnight under vacuum. Small molecule methacrylamides (e.g., compounds of Formula (I) described herein) were screened for their solubility at 0.2M in blends of DMSO and toluene. Fresh solutions of the appropriate DMSO/toluene blend (typically 5-15 v/v % DMSO) were prepared the day of the reaction and degassed with nitrogen prior to use. The methacrylamide was added and vortexed or sonicated to achieve a clear 0.2M working solution. The surface of clean PDMS disks were activated by air plasma treatment (<300 mtorr, 30W, 1 minute per side). After the second treatment, the disks were immediately removed from the reactor and transferred to the working solution for a one-hour reaction with mild agitation. Post-reaction, the disks were washed 3×10 minutes in methanol, 3×10 minutes in 200 proof ethanol, and then dried overnight under vacuum. Disks were sterilized by dipping into 70% ethanol and drying in sterile vials in a sterile hood. Disks were stored at room temperature prior to use.

Example 5: Conjugation of Exemplary Compounds onto a Surface Via Plasma Treatment The compounds described in this disclosure can be attached to surfaces with a variety of methods. In this example, an acrylate derivative is attached to a polymer surface via plasma treatment. The polymeric material or device may be treated with plasma for set time period (e.g., 1 minute of each side (Harrick Plasma Cleaner)) and immediately dropped into a solution of the compound (e.g., a compound of Formula (I)) in 5% DMSO in toluene (0.2M overall). The reaction can be stirred or shaken (as appropriate) for 1 h. The materials will be filtered out of the solution and washed with methanol (3×), ethanol (3×) and dried under vacuum.

Example 6. In Vitro Assay of Exemplary Compounds: Cathepsin Activity

Efficacy and/or toxicity of the compounds, materials, and devices disclosed herein, may be investigated using an in vitro cathepsin activity assay as described in Vegas et al (2016) *Nat Biotechnol* 34(3):666. Briefly, recombinant mouse Cathepsin B (rmCathepsin B, R&D System) may be diluted to 10 uM in activation buffer (25 mM MES, 5 mM DTT, pH 5.0), and incubated at rt for 15 minutes to activate, then diluted further in assay buffer (25 mM MES, pH 5.0) and transferred to the wells of a 96-well plate to a final concentration of 0.1 uM. The substrate (e.g., Prosense 750 Fast (PerkinElmer) and barium chloride) can be diluted in assay buffer and transferred into the wells of the plate containing the Cathepsin B, such that the final concentration of the substrate may be 0.5 uM and barium chloride 20 mM. Fluorescence measurements may then be recorded after a 2 hour incubation at rt using appropriate excitation and emission wavelengths of the substrate. Other cathepsins, such as Cathepsin L, may be used in this assay.

Example 7: In Vitro Assay of Exemplary Compounds: Macrophage Adhesion

Efficacy of the compounds, materials, and devices disclosed herein may be further investigated using an in vitro macrophage adhesion assay. Macrophage cell lines were plated onto 96 well plates, 50000 cells per well, and incubated at 37 degrees Celsius for one hour. Plates were then placed at a 45-degree angle and washed by applying fluid shear 5 times. Non-adherent and adherent cells were then separated and treated with a Cell titer-glo kit to quantify the number of live cells. Live cells were detected using luminescence-based plate reader measurements. The resulting cell adhesion values for each small molecule amine was averaged across the eight wells and standard deviations calculated. The average cell adhesion value for each small molecule was normalized relative to the averages for the two controls on each plate: PEG750=0, Fibronectin (FN)=100. Small molecule normalized value=(SM-PEG750)/(FN-PEG750). Results are expressed as a percentage of cells adhered on the plates. % Percent adherent cells 32 (Luminescence of adhered cells)/(Luminescence of adhered+non-adhered cells). Data represents mean+/− standard error of the mean and are not shown.

Example 8. In Vivo Assay of Exemplary Compounds: Cathepsin Activity

In order to determine the efficacy and/or toxicity of the compounds, materials, and devices disclosed herein, an in vivo fluorescent assay may be used as described in Vegas et al (2016) *Nat Biotechnol* 34(3):666. In general, young mice (e.g., 8-12 week old female SKH1 mice) will be administered, injected, or implanted with the compound, material, or device of interest. The mice may be fed an AIN-93G purified rodent diet to minimize fluorescent background after administration, injection, or implantation. Six days later, ProSense-680 (VisEn Medical, 2-5 nm) will be dissolved in sterile PBS and injected into the tail vein of each mouse. At day 7, the mice will be analyzed by fluorescence imaging to determine the level of cathepsin activity, which correlates to the modulation of the inflammatory response in the site of interest. The inflammatory response may also be assessed by detecting and measuring a suite of cytokines, such as TNF-α, IL-13, IL-6, G-CSF, GM-CSF, IL-4, CCL2, and CCL4, which are known mediators of the foreign body response and fibrosis.

Example 9. In Vivo Assay of Exemplary Compounds: Disk Implantation 5 mm silicone disks that were chemically modified as described in Example 4 were implanted into the intraperitoneal (IP) space of C57BL/6J mice according to the procedure below.

Preparation: Mice were prepared for surgery by being placed under anesthesia under a continuous flow of 1-4% isofluorane with oxygen at 0.5 L/min. Preoperatively, all mice received a 0.05-0.1 mg/kg of body weight dose of buprenorphine subcutaneously as a pre-surgical analgesic, along with 0.5 ml of 0.9% saline subcutaneously to prevent dehydration. A shaver with size #40 clipper blade was used to remove hair to reveal an area of about 2 cm×2 cm on ventral midline of the animal abdomen. The entire shaved area was aseptically prepared with a minimum of 3 cycles of scrubbing with povidine (in an outward centrifugal direction from the center of the incision site when possible), followed by rinsing with 70% alcohol. A final skin paint with povidine was also applied. The surgical site was draped with sterile disposable paper to exclude surrounding hair from touching the surgical site, after disinfection of table top surface with 70% ethanol. Personnel used proper PPE, gowning, surgical masks, and surgical gloves.

Surgical procedure: A sharp surgical blade or scissor was used to cut a 0.5-0.75 mm midline incision through the skin and the linea alba into the abdomen of the subject mice. The surgeon attempted to keep the incision as small as possible. Flat sterile forceps were used to transfer one silicone disk into the peritoneal cavity of each mouse. The abdominal muscle was closed by suturing with 5-0 Ethicon black silk or PDS-absorbable 5.0-6.0 monofilament absorbable thread, and the external skin layer was closed using wound clips. Blood and tissue debris were removed from the surgical instruments between procedures and the instruments were also re-sterilized between animal using a hot bead sterilizer. After the surgery, the animals were put back in the cage on a heat pad or under a heat lamp and monitored until they came out of anesthesia.

Intraoperative care: Animals were kept warm using Deltaphase isothermal pad. The animal's eyes were hydrated with sterile ophthalmic ointment during the period of surgery. Care was taken to avoid wetting the surgical site excessively to avoid hypothermia. Respiratory rate and character were monitored continuously. If vital signs are indicative of extreme pain and distress, the animal was euthanized in a carbon dioxide chamber followed by cervical dislocation.

Fourteen days post-implantation, the disks were retrieved and the number of disks containing adhered tissue was counted. The results of this assay are summarized in Table 3 below. In this table, "A" corresponds with a value of 0-1 disks containing adhered tissue; "B" corresponds with a value of 2-3 disks containing adhered tissue; and "C" corresponds with a value of 4-5 disks containing adhered tissue.

TABLE 3

| Compound Number | Assay Results |
|---|---|
| 100 | B |
| 101 | B |
| 102 | B |
| 103 | B |
| 104 | B |
| 105 | B |
| 107 | B |
| 108 | B |
| 109 | A |
| 110 | A |
| 111 | A |
| 112 | B |
| 113 | B |
| 117 | B |
| 118 | B |
| 114 | B |
| 115 | B |
| 116 | B |

EQUIVALENTS AND SCOPE

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, Figures, or Examples but rather is as set forth in the appended claims. Those of ordinary skill in the art will appreciate that various changes and modifications to this description may be made without departing from the spirit or scope of the present invention, as defined in the following claims.

The invention claimed is:

1. An alginate modified with a compound of Formula (II-b):

(II-b)

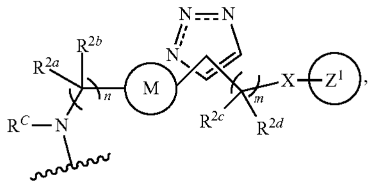

or a pharmaceutically acceptable salt thereof, wherein:

Ring $M^1$ is phenyl optionally substituted with one $R^3$;

Ring $Z^1$ is selected from

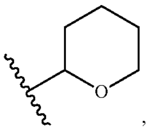,
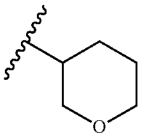,
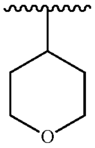, and
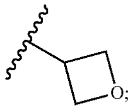

each of $R^{2a}$, $R^{2b}$, $R^{2c}$, and $R^{2d}$ is independently hydrogen or alkyl;

X is O;

$R^3$ is heteroalkyl, $R^C$ is hydrogen or alkyl;

n is 1;

m is 1 or 2; and,

"∿∿" refers to a connection to an attachment group or the alginate provided that the compound is not

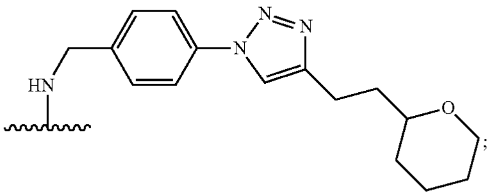 [SMILES: *NCc1ccc(-n2cc(CCC3CCCCO3)nn2)cc1];

and, when $Z^1$ is

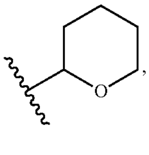 [SMILES: *C1CCCCO1], then one or more of following apply:

(i) the triazolyl ring is

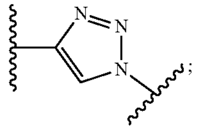 [SMILES: *c1cn(*)nn1]

(ii) one of $R^{2a}$ or $R^{2b}$ is not hydrogen; or (iii) Ring $M^1$ is substituted with 1 $R^3$.

2. The alginate of claim 1, wherein each of $R^{2a}$, $R^{2b}$, $R^{2c}$, and $R^{2d}$ is independently hydrogen.

3. The alginate of claim 1, wherein each of m and n is independently 1.

4. The alginate of claim 1, wherein the compound is selected from:

| Compound No. | Structure |
|---|---|
| 104 | 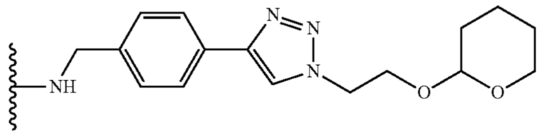 [SMILES: *NCc1ccc(-c2cn(CCOC3CCCCO3)nn2)cc1] |
| 105 | 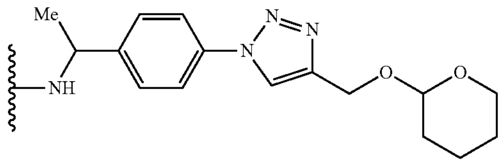 [SMILES: *NC(C)c1ccc(-n2cc(COC3CCCCO3)nn2)cc1] |
| 106 | 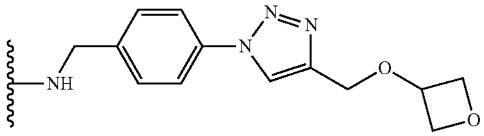 [SMILES: *NCc1ccc(-n2cc(COC3COC3)nn2)cc1] |
| 108 | 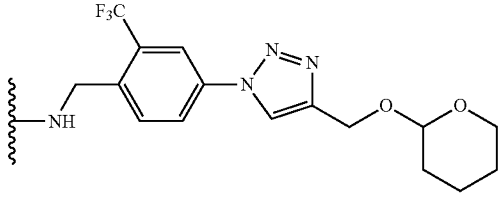 [SMILES: *NCc1ccc(-n2cc(COC3CCCCO3)nn2)cc1C(F)(F)F] |

or a pharmaceutically acceptable salt thereof.

5. The alginate of claim 1, the alginate is a high guluronic acid alginate or a high mannuronic acid alginate.

6. The alginate of claim 1, wherein the alginate comprises an increase in % N of 0.1 to 10% N by weight, where % N is determined by elemental analysis and corresponds to the amount of compound of Formula (II) in the modified alginate.

7. An alginate modified with a compound of Formula (II-b):

(II-b)

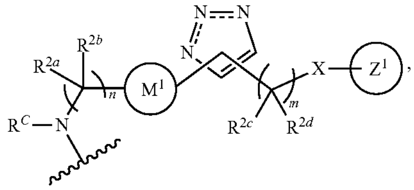

or a pharmaceutically acceptable salt thereof, wherein:

Ring $M^1$ is phenyl optionally substituted with one or more $R^3$;

Ring $Z^1$ is heterocyclyl optionally substituted with 1-5 $R^5$;

each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group;

X is absent;

each $R^3$ and $R^5$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with one or more halogen, oxo, cyano, cycloalkyl, or heterocyclyl; or two $R^5$ are taken together to form a 5-6 membered ring fused to Ring $Z^1$;

$R^C$ is hydrogen or alkyl;

each $R^{A1}$ and $R^{B1}$ is independently hydrogen, alkyl, or heteroalkyl;

m and n are each independently 1, 2, 3, 4, 5, or 6; and

“ ” refers to a connection to an attachment group or the alginate.

8. The alginate of claim 7, wherein the compound of Formula (II-b) is
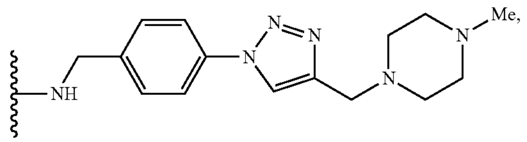 [SMILES: *NCc1ccc(-n2cc(CN3CCN(C)CC3)nn2)cc1]
or a pharmaceutically acceptable salt thereof.
* * * * *